(12) United States Patent
Vaterlaus

(10) Patent No.: US 11,529,074 B2
(45) Date of Patent: Dec. 20, 2022

(54) WELLNESS AND DISCOVERY SYSTEMS AND METHODS

(71) Applicant: adidas AG, Herzogenaurach (DE)

(72) Inventor: Amy Jones Vaterlaus, Portland, OR (US)

(73) Assignee: adidas AG, Herzogenaurach (DE)

( * ) Notice: Subject to any disclaimer, the term of this patent is extended or adjusted under 35 U.S.C. 154(b) by 614 days.

(21) Appl. No.: 15/456,272

(22) Filed: Mar. 10, 2017

(65) Prior Publication Data
US 2018/0256078 A1    Sep. 13, 2018

(51) Int. Cl.
| | |
|---|---|
| *A61B 5/11* | (2006.01) |
| *A61B 5/00* | (2006.01) |
| *A61B 5/16* | (2006.01) |
| *A61B 5/024* | (2006.01) |
| *A61B 5/026* | (2006.01) |
| *A61B 5/08* | (2006.01) |
| *A61B 5/01* | (2006.01) |

(Continued)

(52) U.S. Cl.
CPC ........... *A61B 5/1118* (2013.01); *A61B 5/1112* (2013.01); *A61B 5/7435* (2013.01); *A61B 5/0024* (2013.01); *A61B 5/01* (2013.01); *A61B 5/024* (2013.01); *A61B 5/026* (2013.01); *A61B 5/0816* (2013.01); *A61B 5/14542* (2013.01); *A61B 5/165* (2013.01); *A61B 5/486* (2013.01); *A61B 5/4815* (2013.01); *A61B 5/4848* (2013.01); *A61B 5/4866* (2013.01); *A61B 5/4875* (2013.01); *A61B 5/6801* (2013.01); *H04M 1/72412* (2021.01); *H04W 4/12* (2013.01)

(58) Field of Classification Search
CPC ....... A61B 5/1118; A61B 5/74; A61B 5/7435; G06F 19/3481; G06F 19/3475; G09B 19/0038; G09B 19/0092; G16H 20/00; G16H 20/30; G16H 20/60; A63B 24/0075
See application file for complete search history.

(56) References Cited

U.S. PATENT DOCUMENTS

| | | | |
|---|---|---|---|
| 8,956,290 B2* | 2/2015 | Gilley | G06Q 10/06 600/301 |
| 2014/0272846 A1* | 9/2014 | Richling | G09B 19/00 434/236 |

(Continued)

FOREIGN PATENT DOCUMENTS

WO    WO 02/067449 A2    8/2002

*Primary Examiner* — Devin B Henson
(74) *Attorney, Agent, or Firm* — Sterne, Kessler, Goldstein & Fox P.L.L.C.

(57) ABSTRACT

Devices, systems, and methods can be used to suggest a discovery to an individual related to their health and wellness, including receiving data about the individual from a user interface regarding a goal for the individual, querying the individual regarding their perception of the goal, determining, a likely state of the individual (e.g., readiness to change), and selecting a subset of discoveries to display to the individual from a database that correspond to both the goal for the individual and the likely state of the individual. Displaying information may include receiving motion data including duration of motion, classifying a type of activity the individual is engaged in based on the motion data and likely intensity of the activity, and displaying a graphical user interface including a color spectrum, depending on one of the type of activity, intensity of the activity, or duration of the activity.

15 Claims, 50 Drawing Sheets

(51) Int. Cl.
 *A61B 5/145* (2006.01)
 *H04W 4/12* (2009.01)
 *H04M 1/72412* (2021.01)

(56) References Cited

U.S. PATENT DOCUMENTS

2017/0132395 A1* 5/2017 Futch .................... G06Q 40/08
2018/0056130 A1* 3/2018 Bitran ................ G06F 19/3418

* cited by examiner

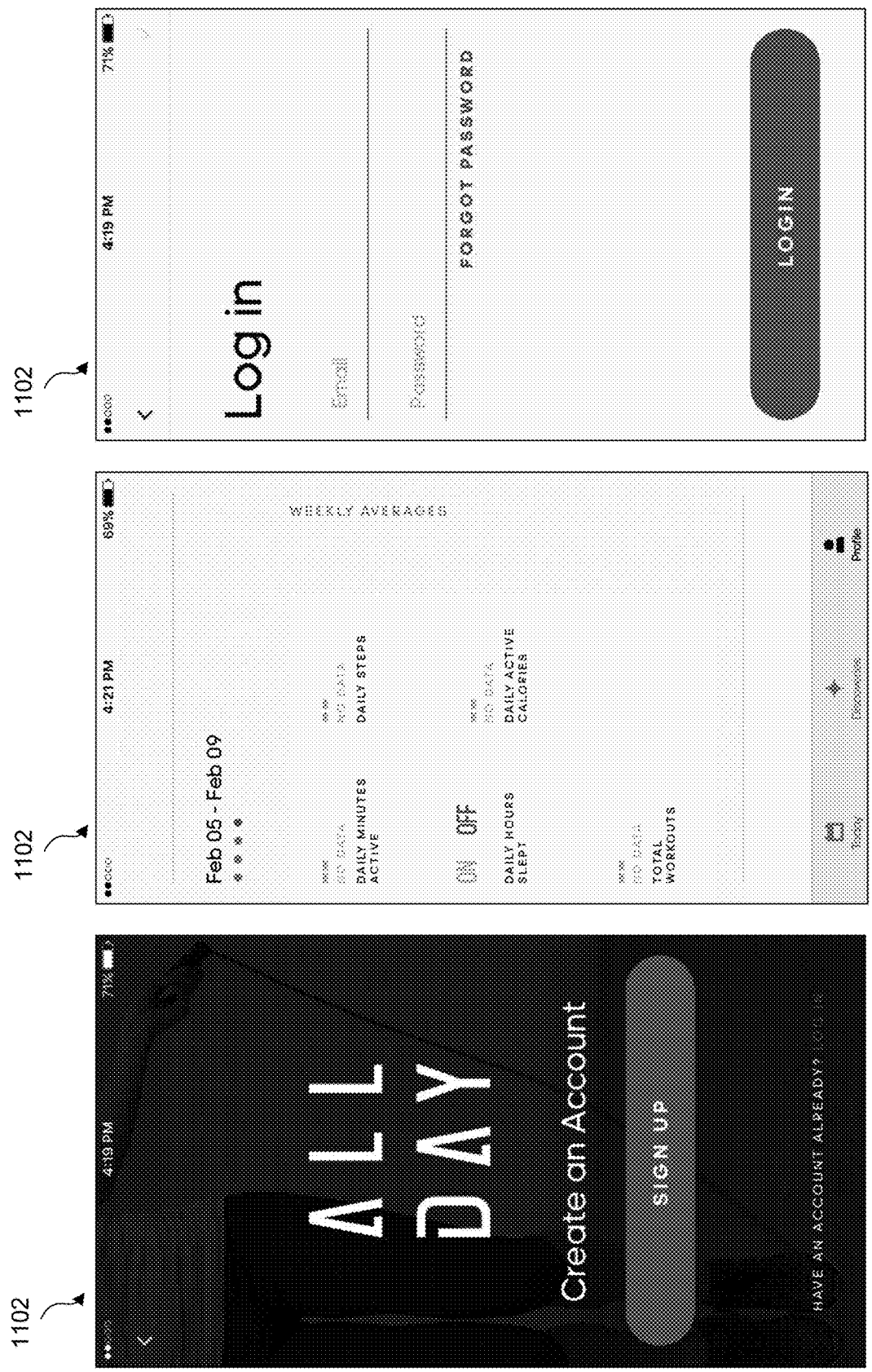

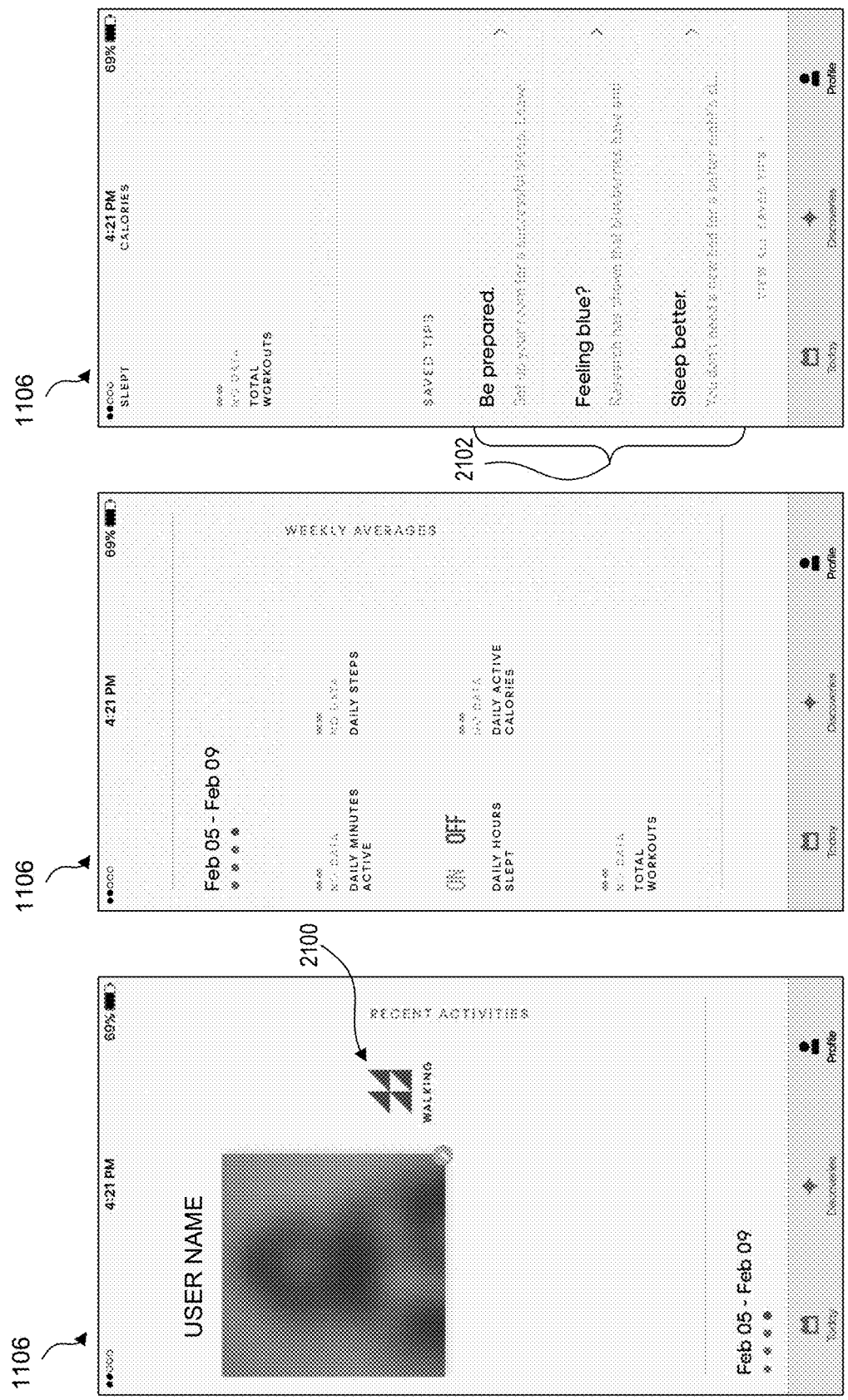

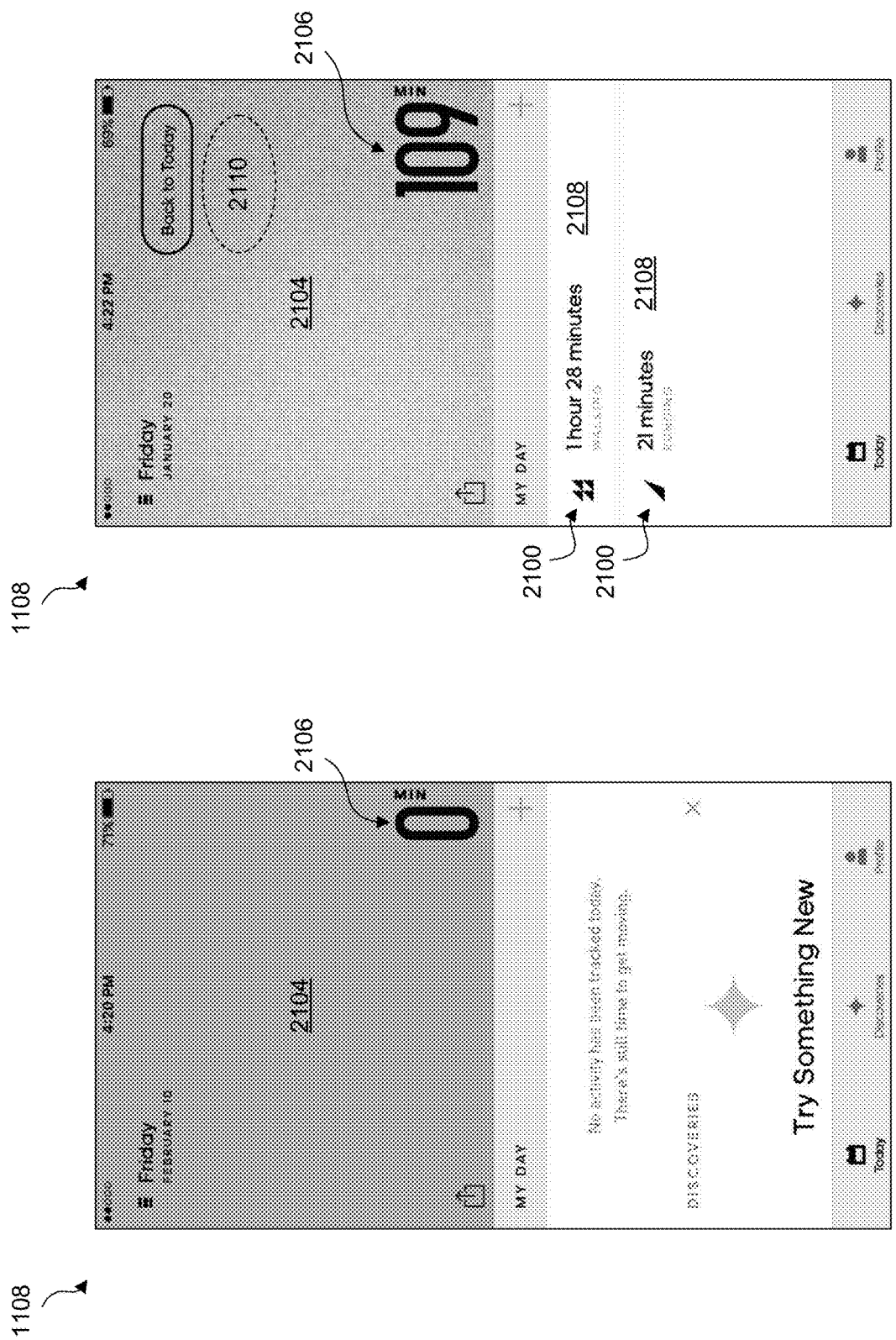

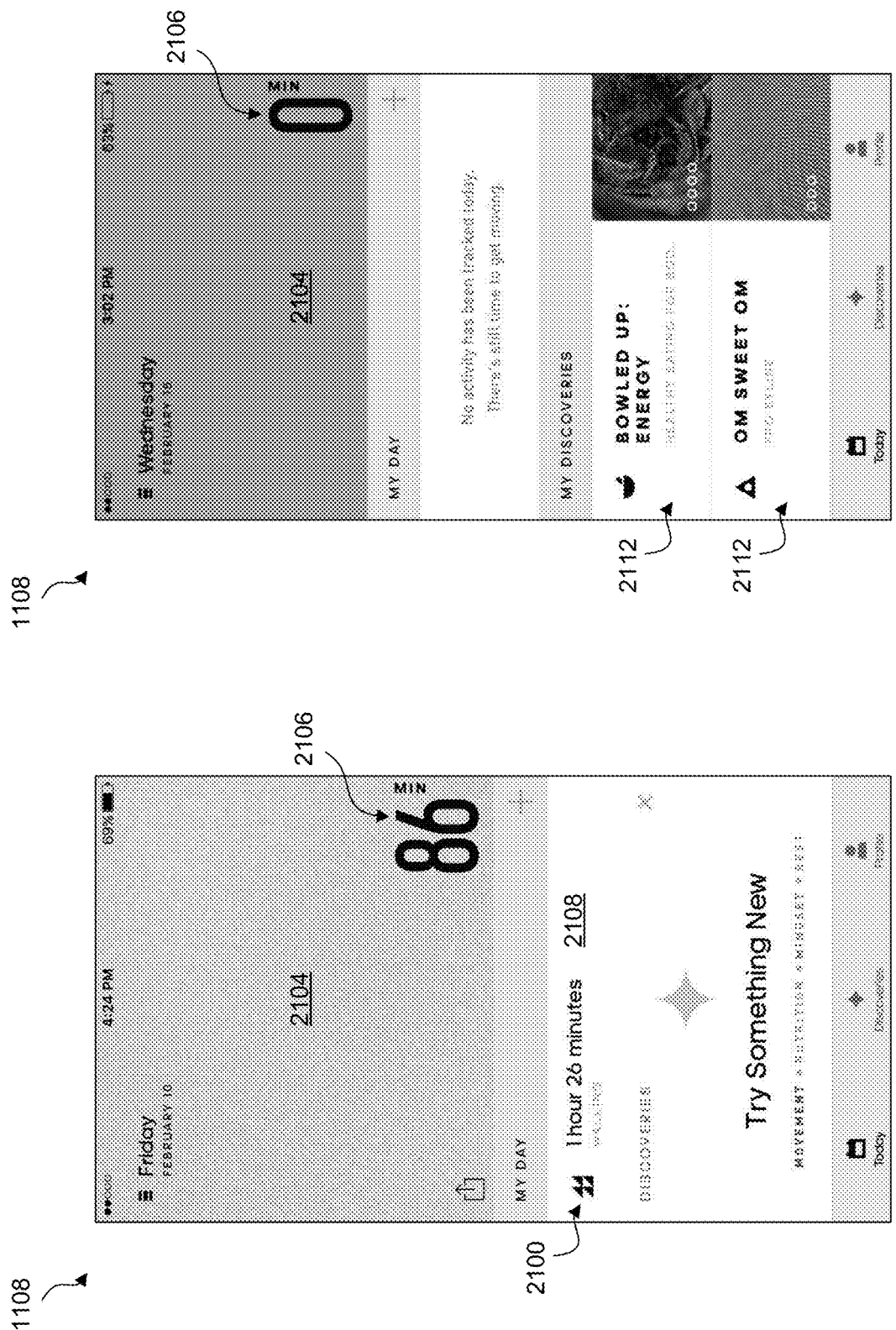

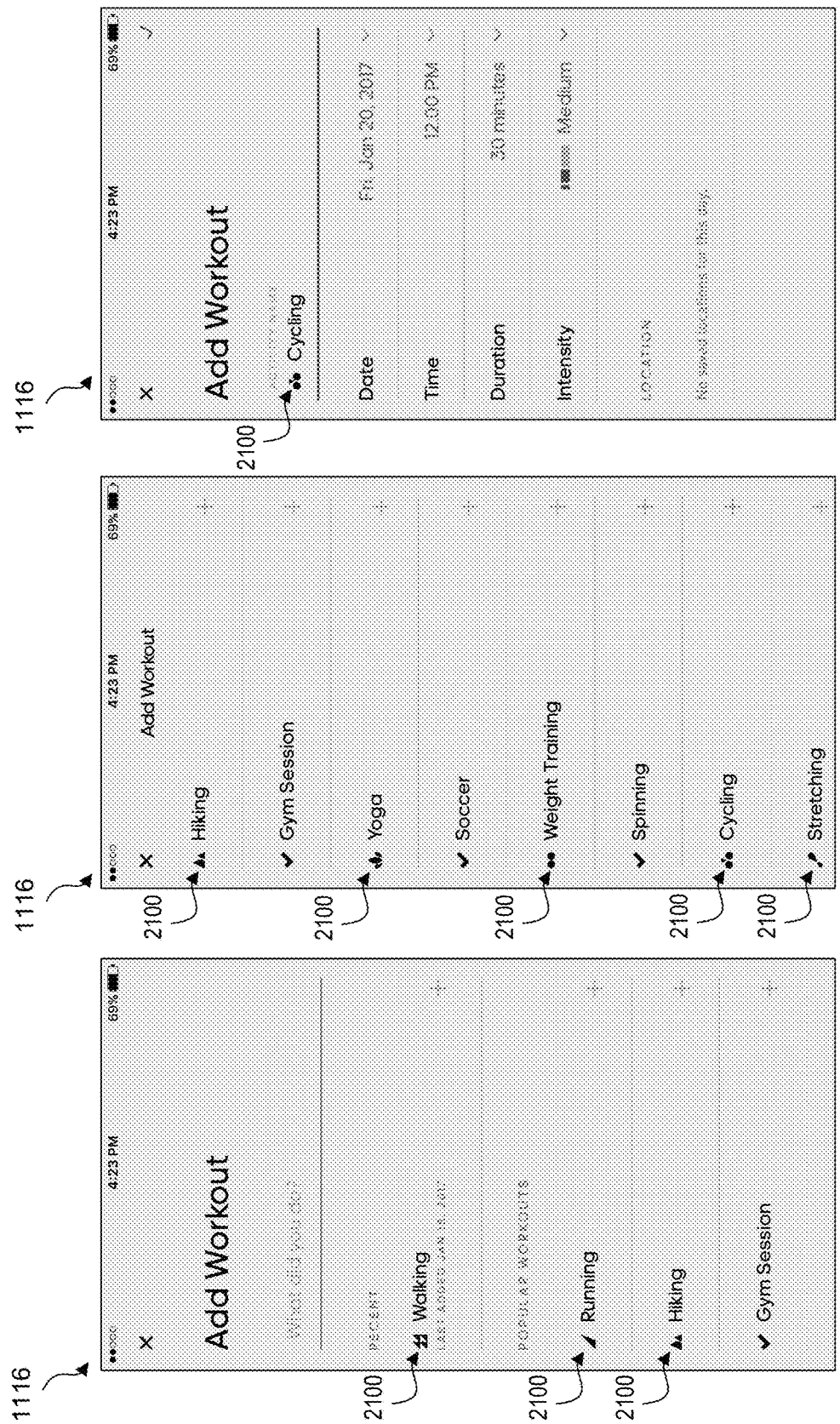

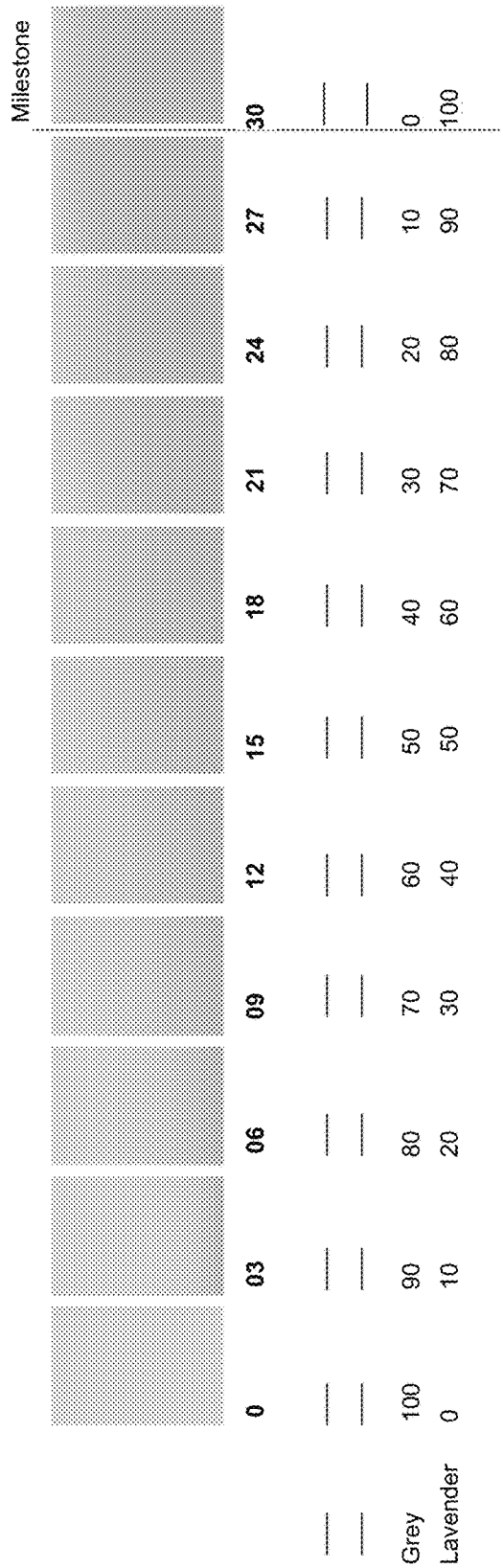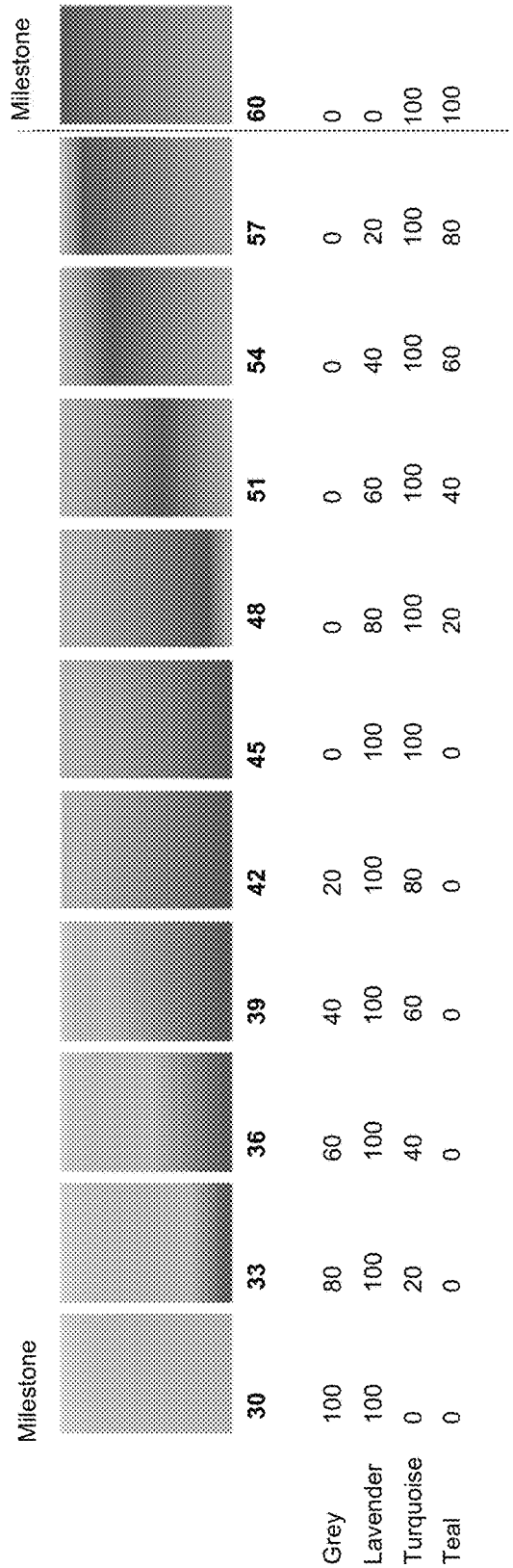
FIG. 28A

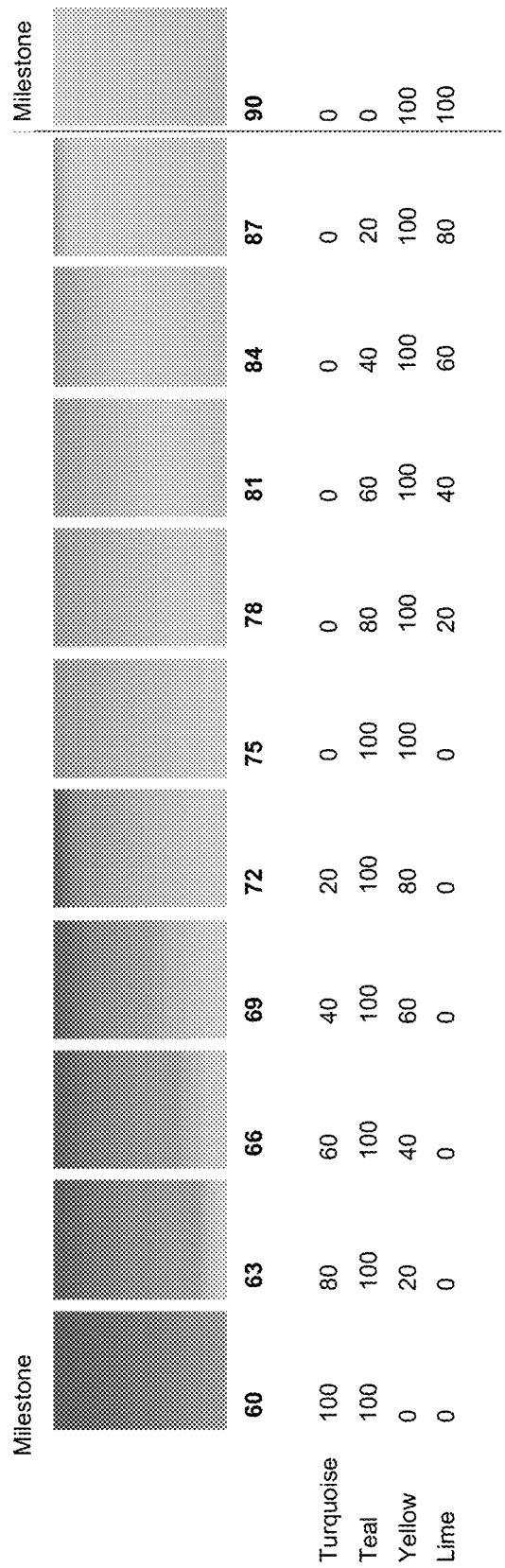
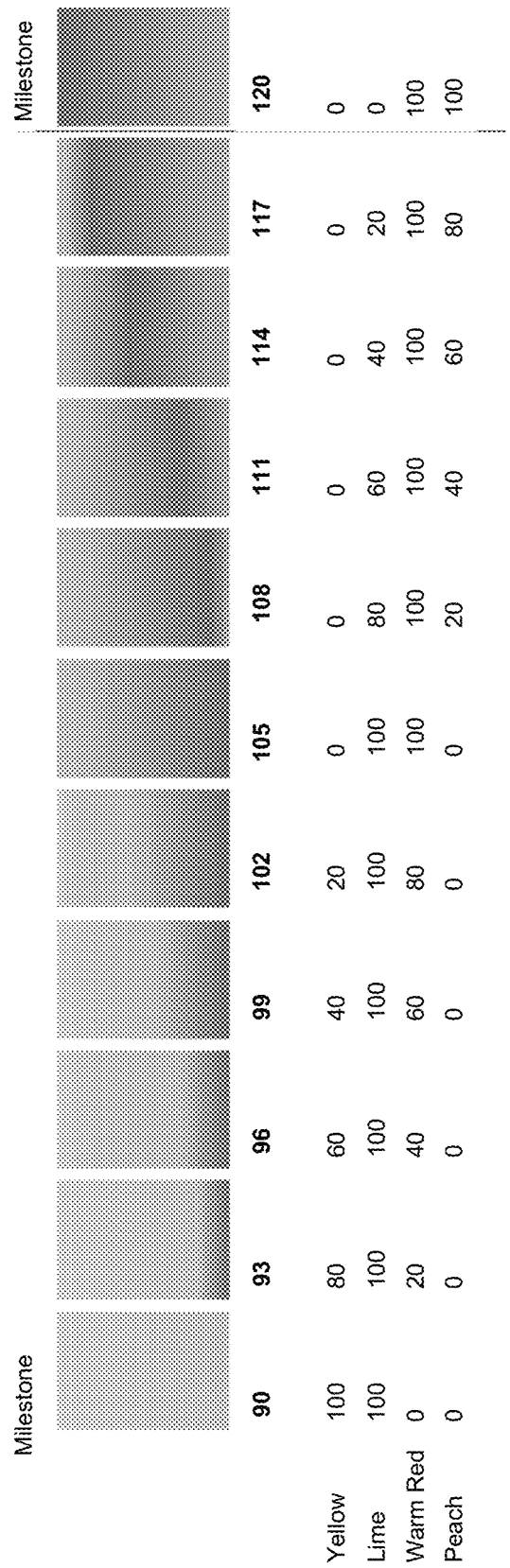
FIG. 28B

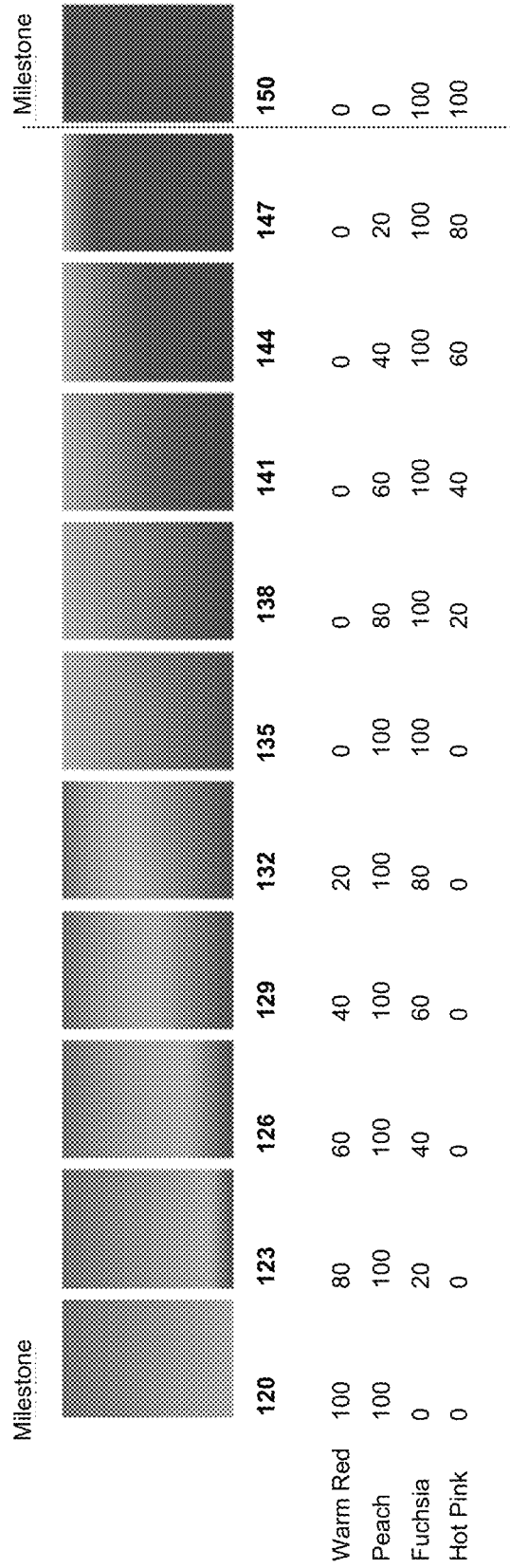
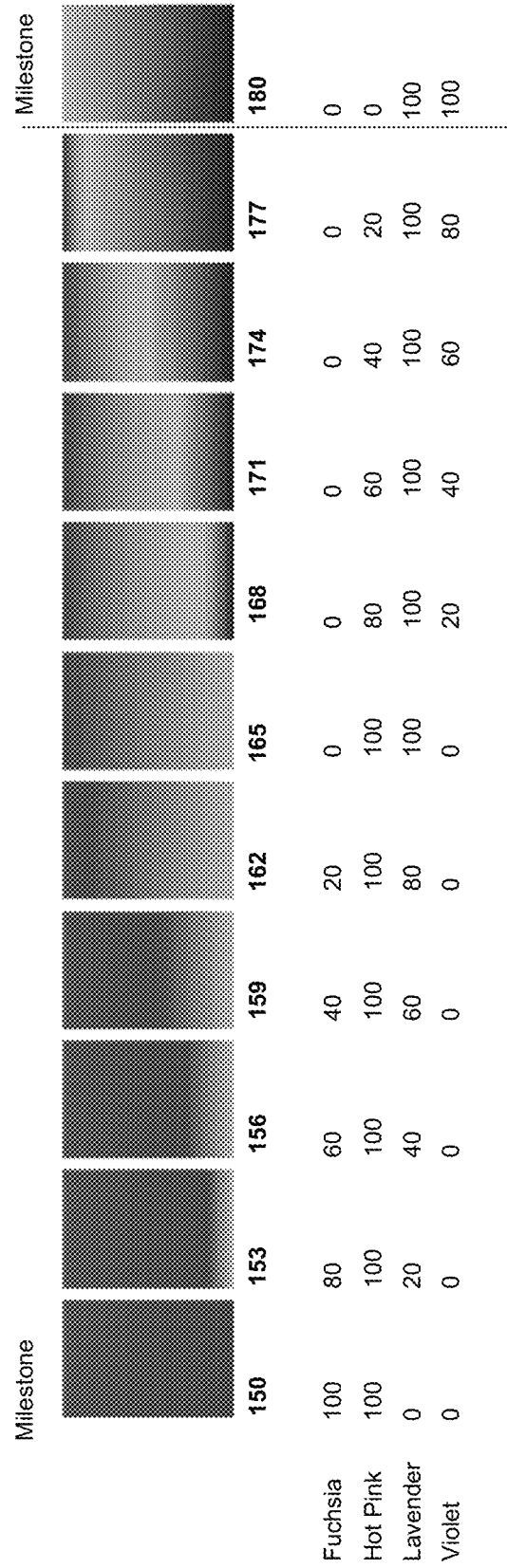
FIG. 28C

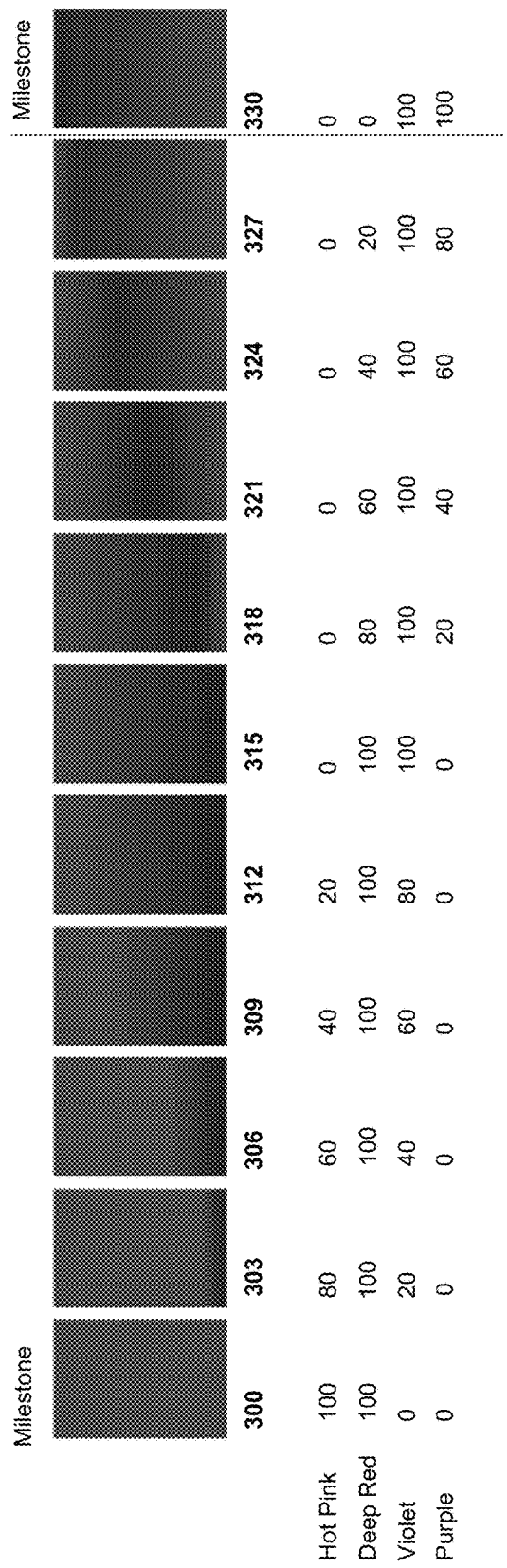
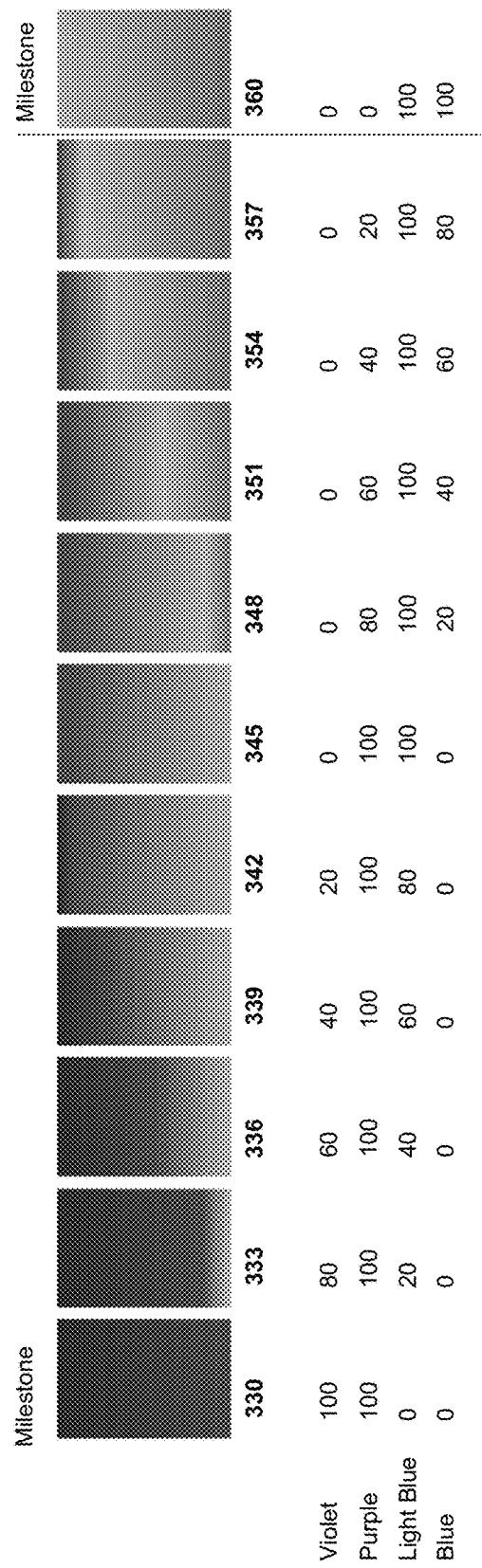
FIG. 28F

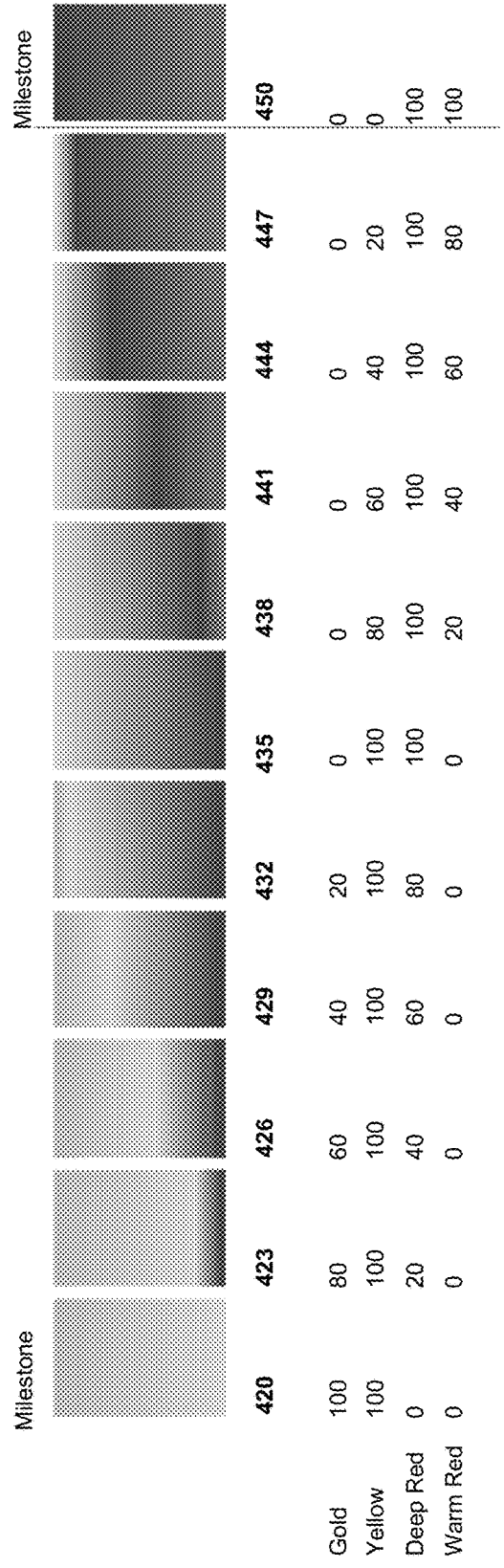
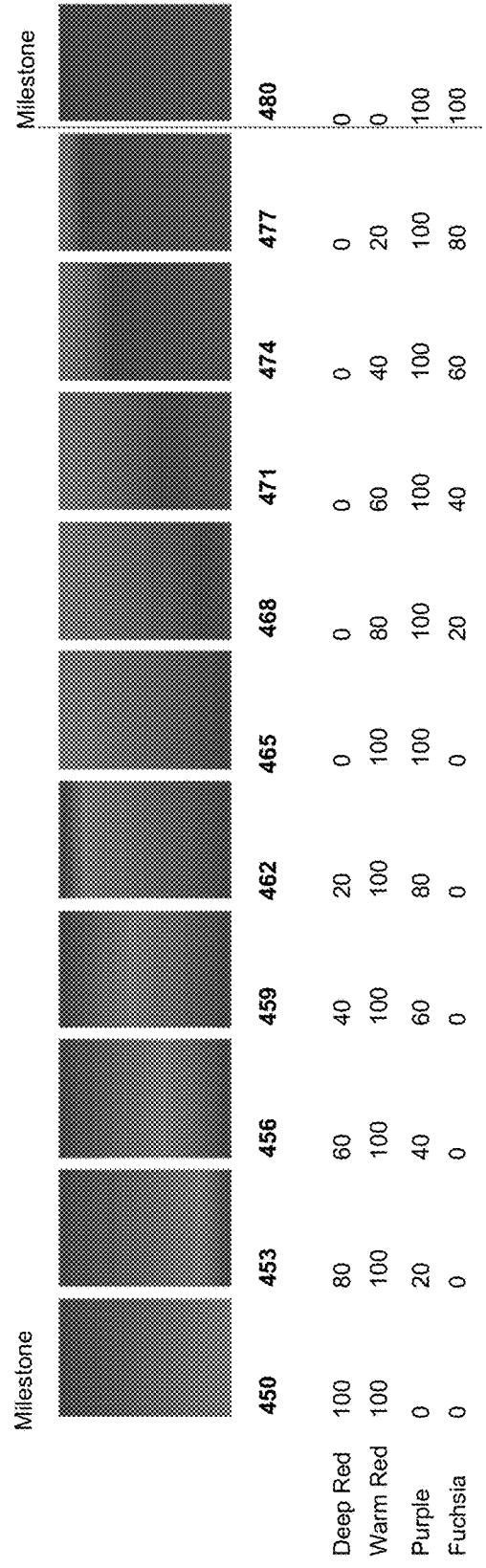
FIG. 28H

What makes up the community?
- The General System 10 Public
- System Created Clusters
- Sarah's Collective
- Sarah's Tribe(s)

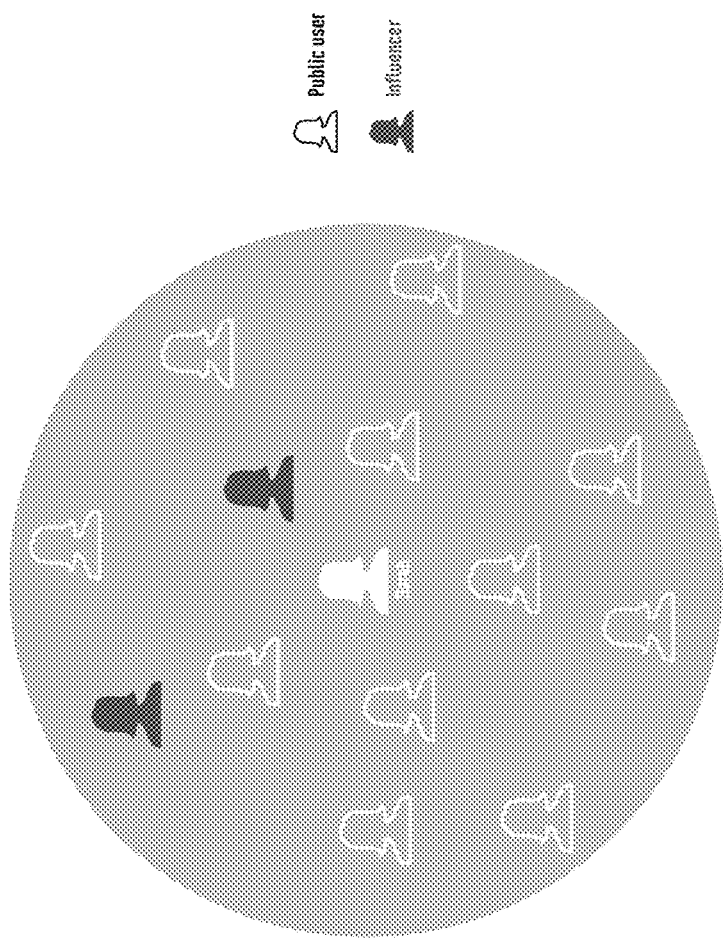

The public space

There is a public space that all users can access, view and contribute to.

- Influencers will play a big part in the public Space. They can algorithmically be given more prominence to have more visibility either through what information is shown in the Public Space or encouraging user to follow.
- System 10 users that have public profiles will also regularly contribute to the public feed.

FIG. 33

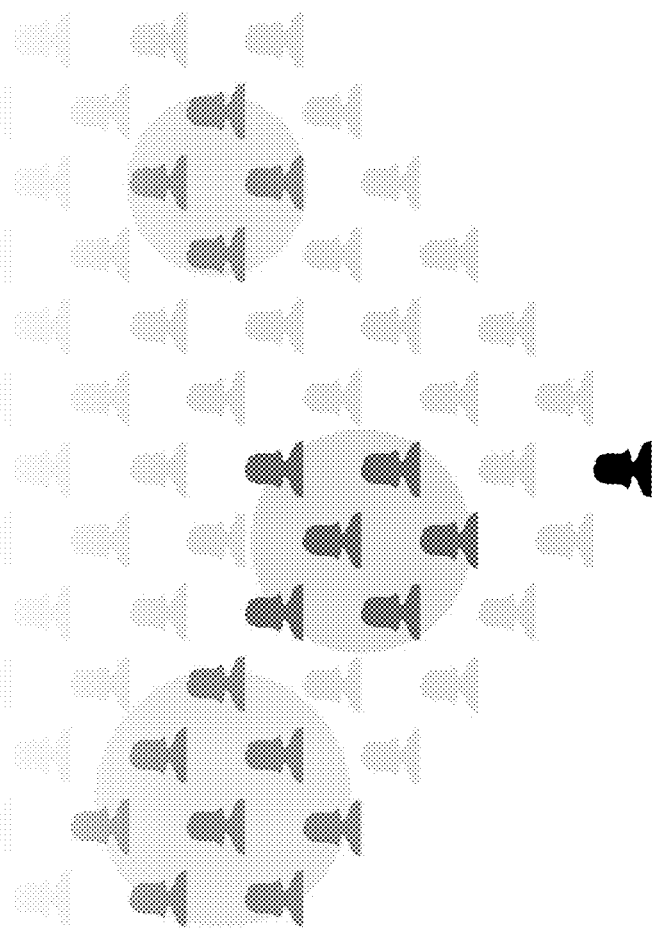

"We think you'd enjoy following Kim because..."

FIG. 34

System created clusters

These are groups created by the system and not visible to the user.

These clusters can be used as a way to identify items that show up in her public view of the feed, recommendations for discoveries, and recommendations for people Sarah may find interesting to follow.

Possible match criteria

- Age
- Gender
- Location
- Common Collectives
- Common activities
- Common Discoveries
- Common behaviour in the app (liking/articles read etc.)

Sarah's Collective

The Collective is the network of connections a user has curated. These could be friends a user has in the real world, total strangers or influencers.

Sarah chooses who to follow...
- to provide her inspiration
- for her to provide support Sarah has followers...
- to provide her support
- to celebrate and commiserate with her
- draw inspiration from Sarah Sarah's Tribes
- Tribes are user created groups
- Tribes are organized around a Discovery.
- Sarah can join multiple tribes to do Discoveries with different groups.

WELLNESS AND DISCOVERY SYSTEMS AND METHODS

FIELD OF THE INVENTION

Embodiments of the present invention generally relate to methods and systems related to health and wellness tracking. More particularly, embodiments of the present invention relate to methods and systems for tracking and encouraging behavior through participation in discoveries.

BACKGROUND OF THE INVENTION

Athletic activity and general wellness activity can take many forms—some individuals prefer to engage in team athletic activities such as, for example, soccer or basketball, while other individuals prefer to engage in individual athletic activities such as, for example, running or skiing. Some individuals enjoy guided meditation, yoga, or other mindfulness exercises. Regardless of whether the activity is a team or individual activity, it is becoming more and more common for individuals to actively track their performance, including with respect to nutrition, mindset, and rest.

In this respect, it is advantageous to provide systems and methods that will track and provide an individual with analytical, quantitative, and qualitative understanding of health and wellbeing. In some respects, activity tracking applications may be complex, including various features and information an individual does not wish to track. Additionally, individuals may wish to use a particular device to track everything, without needing multiple applications or devices. On the other hand, personal choice may contribute to an individual wishing to use a particular data source, for example, because they enjoy a particular device or application. A single application that may aggregate data and information from multiple sources is thus advantageous.

Additionally, individuals may benefit from different types of reinforcement for a desired behavior, depending in part on their readiness to change a behavior. In this respect, applications that may differentiate an individual's mindset and provide appropriate information at a particular time is advantageous.

BRIEF SUMMARY OF THE INVENTION

Embodiments of the present disclosure relate to devices, systems, and methods that can be used to track an individual's activity and health related data, provide feedback, encouragement, etc.

Some embodiments are directed to a health and fitness monitoring system, for example, for suggesting a discovery to an individual. In some embodiments, the system includes a database containing discovery content related to physiological monitoring. In some embodiments, the system includes an electronic device containing a software platform to interface with the database, such that an individual may input, through a user interface on the electronic device, data regarding a physiological goal for the individual, and that may automatically detect physiological data regarding the individual. In some embodiments, the software platform queries the individual regarding their perception of the goal, and determines, based on the query, a likely state of the individual corresponding to their readiness to change. In some embodiments, the software platform interfaces with the database and selects a subset of discoveries to display to the individual from the database that correspond to both the goal for the individual and the likely state of the individual corresponding to their readiness to change. In some embodiments, the database or software platform automatically adjusts the content of the subset of discoveries based on the likely state of the individual corresponding to their readiness to change.

Some embodiments are directed to a method for providing feedback to an individual related to a discovery, including displaying content regarding a discovery selected by the individual, receiving data corresponding to the discovery from the individual, displaying a message related to the individual's selected discovery based in part on the received data, displaying a message related to a discovery not selected by the individual.

In some embodiments, the discovery is related to a domain selected from movement, nutrition, mindset, and rest. In some embodiments, the method includes querying the individual regarding a baseline level of performance related to the selected domain. In some embodiments, the message related to the individual's selected discovery is dependent upon the individual's progress through the discovery. In some embodiments, the message related to the individual's selected discovery is independent upon the individual's progress through the discovery. In some embodiments, the data received includes motion data of the individual. In some embodiments, the method includes querying the individual regarding their perception of the discovery, and displaying content regarding the discovery depending on the perception of the discovery. In some embodiments, the method includes displaying a message related to the discovery based on the individual's location. In some embodiments, the method includes querying the individual regarding their perception of the discovery, determining, based on the query, a likely state of the individual corresponding to their readiness to change, and adjusting the tone of the message based on the likely state of the individual. In some embodiments, the likely state of the individual is categorized based on the transtheoretical model.

Some embodiments are directed to a method for suggesting a discovery to an individual, including receiving data about the individual from a user interface regarding a goal for the individual, querying the individual regarding their perception of the goal, determining, based on the query, a likely state of the individual corresponding to their readiness to change, selecting a subset of discoveries to display to the individual from a database that correspond to both the goal for the individual and the likely state of the individual corresponding to their readiness to change.

In some embodiments, a likely state of the individual is categorized based on the transtheoretical model. In some embodiments, the goal corresponds to a domain selected from movement, nutrition, mindset, and rest. In some embodiments, the method includes querying the individual regarding their progress through a previously selected discovery, and updating the selection of a subset of discoveries to display to the individual based on the query. In some embodiments, the querying the individual regarding their perception of the goal includes querying the individual regarding a baseline selected from movement, nutrition, mindset, and rest. In some embodiments, the method includes adjusting the content of a subset of discoveries based on the likely state of the individual corresponding to their readiness to change.

Some embodiments are directed to a method for displaying information to an individual, including receiving motion data about the individual, the motion data including duration of motion, classifying a type of activity the individual is engaged in based on the motion data and likely intensity of the activity, and displaying a graphical user interface including a color spectrum, wherein the color, color gradient, and color intensity of the color spectrum depends on one of the type of activity, intensity of the activity, or duration of the activity.

In some embodiments, the method includes receiving a second motion data about the individual, the second motion data including duration of motion, classifying a type of second activity the individual is engaged in based on the second motion data and likely intensity of the activity, adding the duration of the first and second activity, wherein the color, color gradient, and color intensity of the color spectrum depends on one of the type of first or second activity, intensity of the activities, or sum of the duration of the activities. In some embodiments, the method includes receiving data manually input from the individual regarding an activity, and adding the duration of the manually input activity to the previous total. In some embodiments, the method includes altering the color spectrum is further dependent upon an additional non-motion data source.

BRIEF DESCRIPTION OF THE DRAWINGS/FIGURES

The accompanying figures, which are incorporated herein, form part of the specification and illustrate embodiments of the present invention. Together with the description, the figures further serve to explain the principles of and to enable a person skilled in the relevant arts to make and use the invention.

FIGS. 5A-14 show various graphical user interfaces for a system according to various embodiments.

FIGS. 28A-28I show an example color progression according to an embodiment.

FIGS. 32-36 illustrate conceptual relationships useful in a social module according to an embodiment.

DETAILED DESCRIPTION OF THE INVENTION

Figure 1:
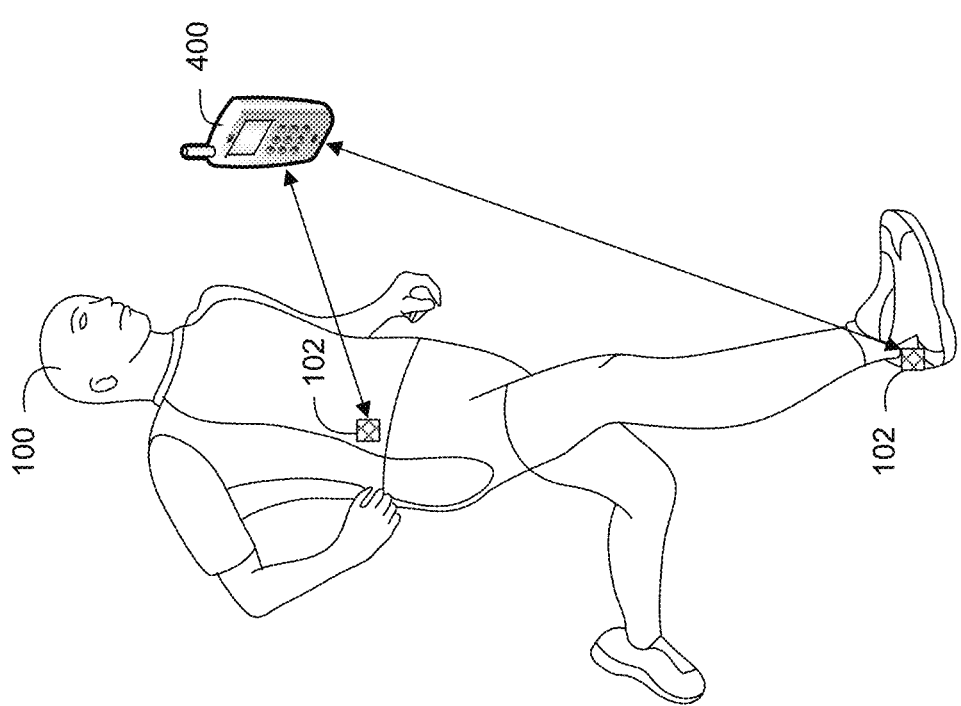
FIG. 1 is an illustration of a system using one or more sensor modules according to various embodiments.

The present invention will now be described in detail with reference to embodiments thereof as illustrated in the accompanying drawings. References to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, non-transitory tangible computer readable or computer usable storage media having instructions stored thereon, or a combination thereof, and may be implemented in one or more computer systems or other processing systems.

The present invention generally relates to methods and systems that collect, store, and communicate data to an individual related to an experience, such as a "discovery experience," or "discovery." Individuals may opt to participate in a "discovery" or "discovery experience". As used herein, discoveries may be time bound experiences, that an individual would like to participate in, for example to make progress towards a goal. Discoveries, may be activities that an individual can perform in order to see what works best to help them reach their goals. Discoveries may be configured such that it encourages the individual to try new things and learn how to build new habits. In some embodiments, discoveries may be related to domains such as movement (e.g., activity, athletics, flexibility, etc.), nutrition (e.g., healthy food, healthy hydration, weight goals, etc.), mindset (e.g., mindfulness, awareness, mental state, decreasing stress, etc.), and rest (e.g., healthy resting habits, balance in activity and rest, etc.).

For individuals seeking to progress towards a goal, generally, different phases progressing towards that goal may be defined in terms of their readiness to change, or other behavior models that focus on other behavioral aspects of decision making and habit forming, for example. Some examples of such models and theories include, for example, a transtheoretical model ("TTM"), Prospect theory of behavior, Social Cognitive theory, Theory of planned behavior, Information-Motivation-Behavioral Skills Model, etc. Although features of the disclosure are described in the context of TTM, models and theories listed herein are also contemplated for inclusion in various systems and methods described.

As an example, the systems and methods described herein may use the prospect theory and apply assumptions based on how individuals chose between probabilistic alternatives that involve risk, e.g., where the probabilities of the outcomes are known, and make use of the potential value of losses or gains evaluating using certain heuristics.

In another example, the systems and methods described herein may use Social cognitive theory ("SCT"), and apply that portions of an individual's knowledge acquisition can be directly related to observing others within the context of social interactions, experiences, and outside media influences. The theory states that when people observe a model performing a behavior and the consequences of that behavior, they remember the sequence of events and use this information to guide subsequent behaviors. Observing a model can also prompt the viewer to engage in behavior they already learned.

In another example, the systems and methods described herein may use the theory of planned behavior ("TPB"), and link beliefs and behavior. The systems and method may apply the relations among beliefs, attitudes, behavioral intentions and behaviors. The theory states that attitude toward behavior, subjective norms, and perceived behavioral control, together shape an individual's behavioral intentions and behaviors.

In another example, the systems and methods described herein may use the theory of Information-Motivation-Behavioral Skills Model ("IMB"). The systems and methods may utilize psychological determinants of the performance of behaviors that have the capacity to impair or to improve health status. The IMB model incorporates and addresses three components—information, motivation, and behavior. The 'information' component targets understanding of the concepts that lead to behavior change and the ways and means of achieving the behavior change. The 'motivation' aspect deals with individual affect and favorable attitude towards positive health behaviors and utilizing existing social support systems to reinforce motivation. Motivation may also be enhanced by recognizing the possible barriers and finding ways to overcome those limitations. The behavioral aspect of the IMB model reflects the psychomotor or 'action' component that allows learning of skills required to bring about change in behavior. Interrelationships among the three constructs of the IMB model as well a set of operations may be are used to translate the IMB model into actions in the systems and methods herein.

Figure 4:
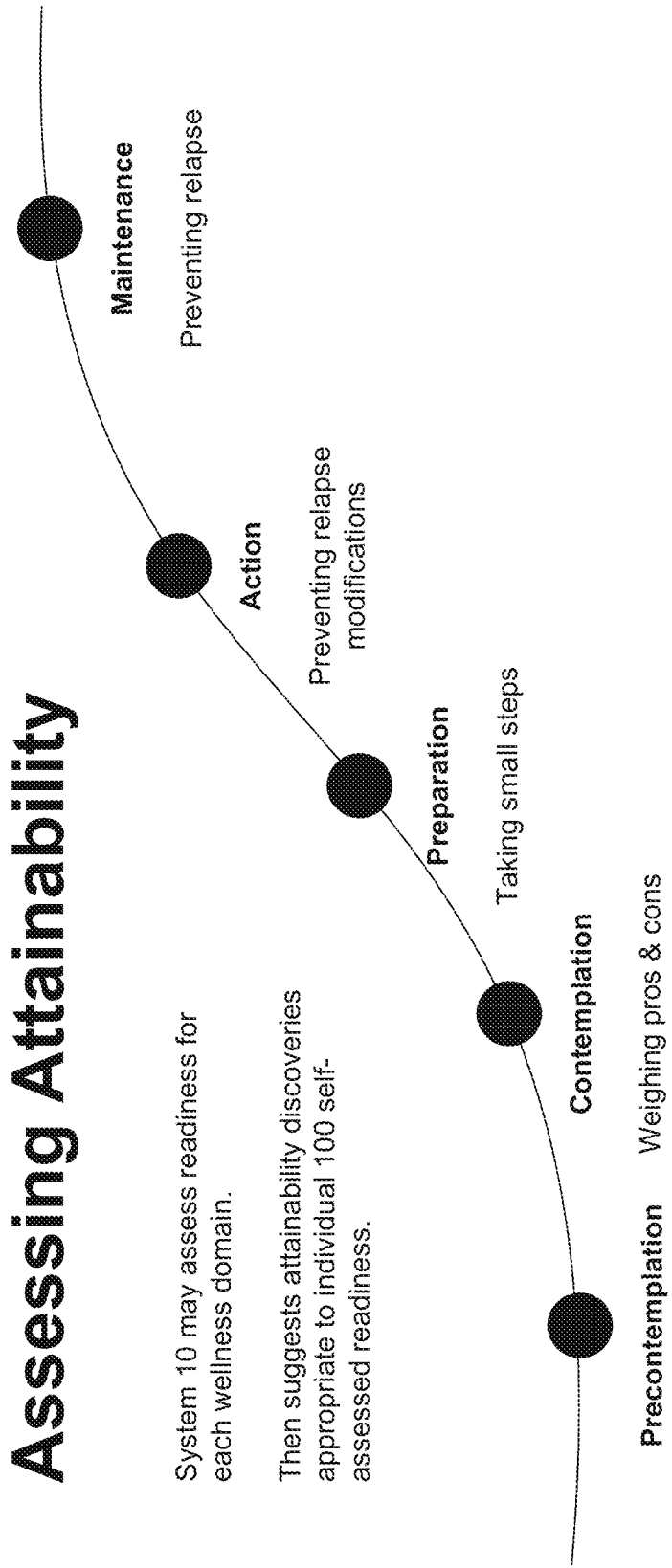
FIG. 4 is a diagram showing transtheoretical model state progression according to various embodiments.

General phases of the TTM are illustrated in FIG. 4, represented by an S-curve showing progress towards a goal. For example, individuals in a pre-contemplation stage do not intend to take action toward a goal in the foreseeable future. In some instances, being uninformed or under informed about the consequences of one's behavior may cause a person to be in the pre-contemplation stage. For some individuals, multiple unsuccessful attempts at change can lead to demoralization about the ability to change. Individuals in the pre-contemplation stage are often may be resistant, unmotivated, or unready for help. Goal categories, may include, for example: eat healthier, increase focus, manage stress, improve mood, sleep better, maintain physical activity, be more active, increase my energy, lose weight, gain weight, look fit, etc.

The TTM stage after pre-contemplation may be deemed the contemplation stage. Contemplation is the stage in which people intend to change in the next six months. They are more aware of the positive aspects of changing a particular behavior, but are also acutely aware of the negatives. This weighting between the costs and benefits of changing can produce profound ambivalence that can cause people to remain in this stage for long periods of time. This phenomenon is often characterized as chronic contemplation or behavioral procrastination. Individuals in the contemplation stage are not ready for traditional action-oriented programs that expect participants to act immediately.

After the contemplation stage, individuals may enter the preparation stage of TTM. Preparation is the stage in which people intend to take action in the immediate future, usually measured as the next month. Typically, they have already taken some significant action in the past year. These individuals have a plan of action, such as joining a gym, consulting a counselor, talking to their physician, or relying on a self-change approach. These individuals may respond to action-oriented programs.

Action is the next sequential TTM stage in which people have made specific overt modifications in their lifestyles within the past six months. Because action is observable, the overall process of behavior change often has been equated with action, however, in some instances, not all modifications of behavior count as action in TTM. In most applications, people must to attain a criterion that scientists and professionals agree is sufficient, e.g., to reduce risk of disease, to increase health or wellness, etc.

Maintenance is the TTM stage in which people have made specific overt modifications in their lifestyles and are working to prevent relapse. In some instances, however, they do not apply change processes as frequently as do individuals in the action TTM stage. While in the maintenance stage, people are less tempted to relapse and grow increasingly more confident that they can continue their changes. Based on self-efficacy data, researchers have estimated that maintenance lasts from six months to about five years.

Within the TTM, if it is known what state an individual is in along the TTM curve (shown in FIG. 4), messaging may be tailored to the individual, and may be further tailored according to an individual's goal or category of goal. Embodiments of the present invention leverage TTM concepts in order to track, monitor, and aid individuals in experiencing growth in areas such as movement (e.g., activity, athletics, flexibility, etc.), nutrition (e.g., healthy food, healthy hydration, weight goals, etc.), mindset (e.g., mindfulness, awareness, mental state, decreasing stress, etc.), and rest (e.g., healthy resting habits, balance in activity and rest, etc.) Embodiments relate to aiding individuals in finding personal balance through a holistic view of health and well-being. In this regard, the systems and methods may track several types of information, and capture everything an individual may do to impact her wellness, aid her in discovering what works for her, offer personally relevant insights, and stay interesting to the individual over a long period of time. To achieve this, principles are applied such that an individual may have a unique experience, does not require tracking of information she is not interested in, is flexible to shifting priorities. Other models described above may also be applied to the features described herein.

Additionally, in some instances, a social element may aid in behavioral change. In some instances, limiting the number of individuals in the social sharing circle may increase likelihood of behavioral change. For example, if a small group of real people are connected to motivate behavior change, this may be more successful than sharing on large social media platform. "Social Physics" science may show that being part of a community reinforces behavioural change, even if others within your network aren't known on a personal level. In some instances, studies have shown that rates of behaviour change achieved with social networks were approximately 4 times higher than rate achieved with individual "nudging".

FIG. 1 illustrates an exemplary system 10 that uses sensor modules 102 and electronic device 400, such as a mobile phone, which may include a sensor module 102. While not specifically shown here, sensor modules could also be embedded in items of apparel (e.g., headbands, hats, wristbands, gloves, jackets, wetsuits, swimsuits, and vests, to name a few non-limiting examples). According to various embodiments, sensor modules 102 may be embedded either removably or permanently in an article of apparel (e.g., clothing or shoes) or in an accessory or piece of athletic equipment (e.g., balls, bats, pads, racquets, clubs, bags, belts, headbands, and wristbands, to name a few non-limiting examples). For instance, in some embodiments sensor devices may be embedded or affixed to an item via, e.g., sewing, gluing, a pocket, integration during manufacturing, to name a few non-limiting examples. Embodiments additionally include use of sensor modules 102 to monitor sleep. In such embodiments, the sensor modules 102 may be attached to, or integrated with sleep garments such as pajamas or sleeping pants with the sensor devices located, for instance, in a waist area or chest area of the sleep garment. For sleep monitoring, sensor modules 102 could be configured to measure night movements, heart rate, and breathing and this data could be processed and used to generate a sleep quality indication.

Suitable portable fitness or activity monitoring software applications may include, for example, the features of those disclosed in commonly owned U.S. Pat. No. 9,392,941, which is incorporated herein by reference in its entirety.

The systems and methods may be effected through software platform 1000 (which may be included in system 10, sensor module 102, electronic device 400, etc.), containing software modules, for example. In some embodiments, fewer modules may be included, or additional modules may be included. In some embodiments, modules may be removed or added, for example through a network connection. Programming data may include software platform, and include various modules. Each of the components in sensor module 102, for example, or electronic device 400, may feed the modules data that the modules use to formulate a response. In other embodiments, the systems and methods may be effected through software platform 1000 in an electronic device 400 in addition to or instead of in system 10.

Figure 2:
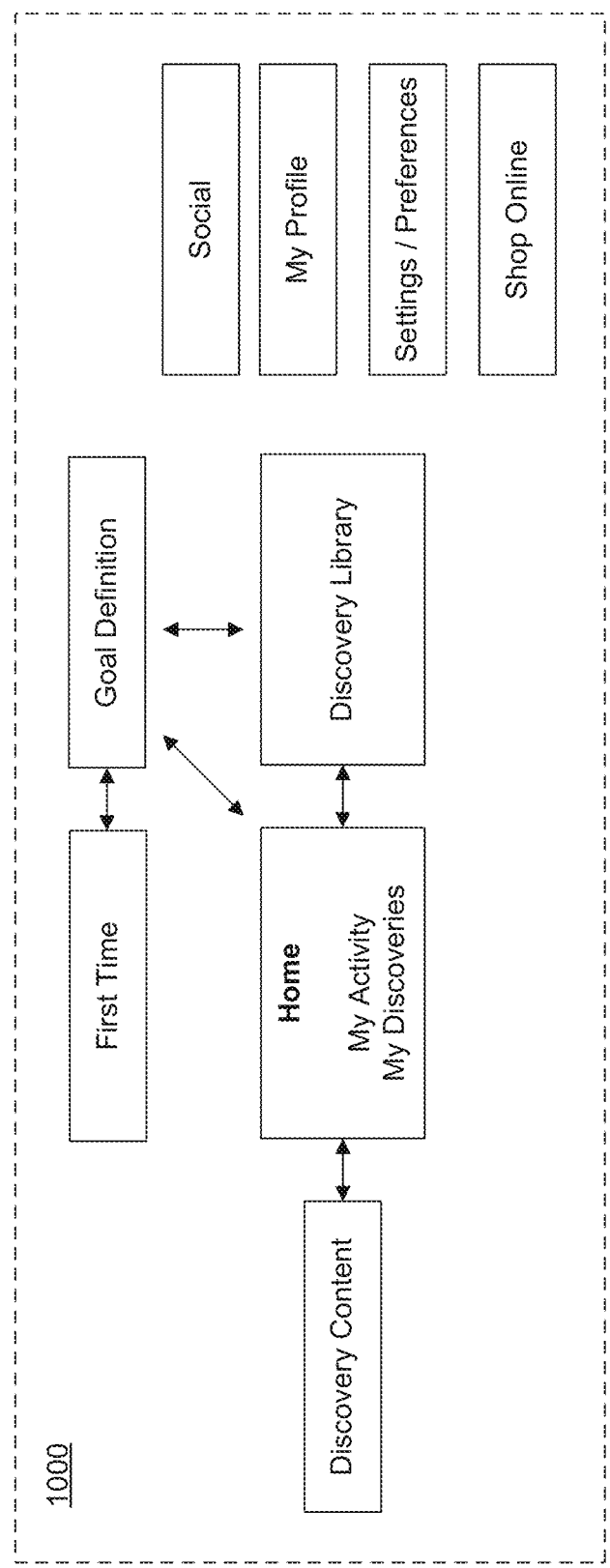
FIG. 2 is a conceptual relationship illustration of a software platform according to an example embodiment.

As shown in FIG. 2, software platform may be generally structured to link functions, such as first time use, goal definitions, discovery library, home, discovery content, etc. Additionally, software platform 1000 may include a profile, settings/preferences, and a link to an online shopping application, and social applications, for example.

Figure 3:
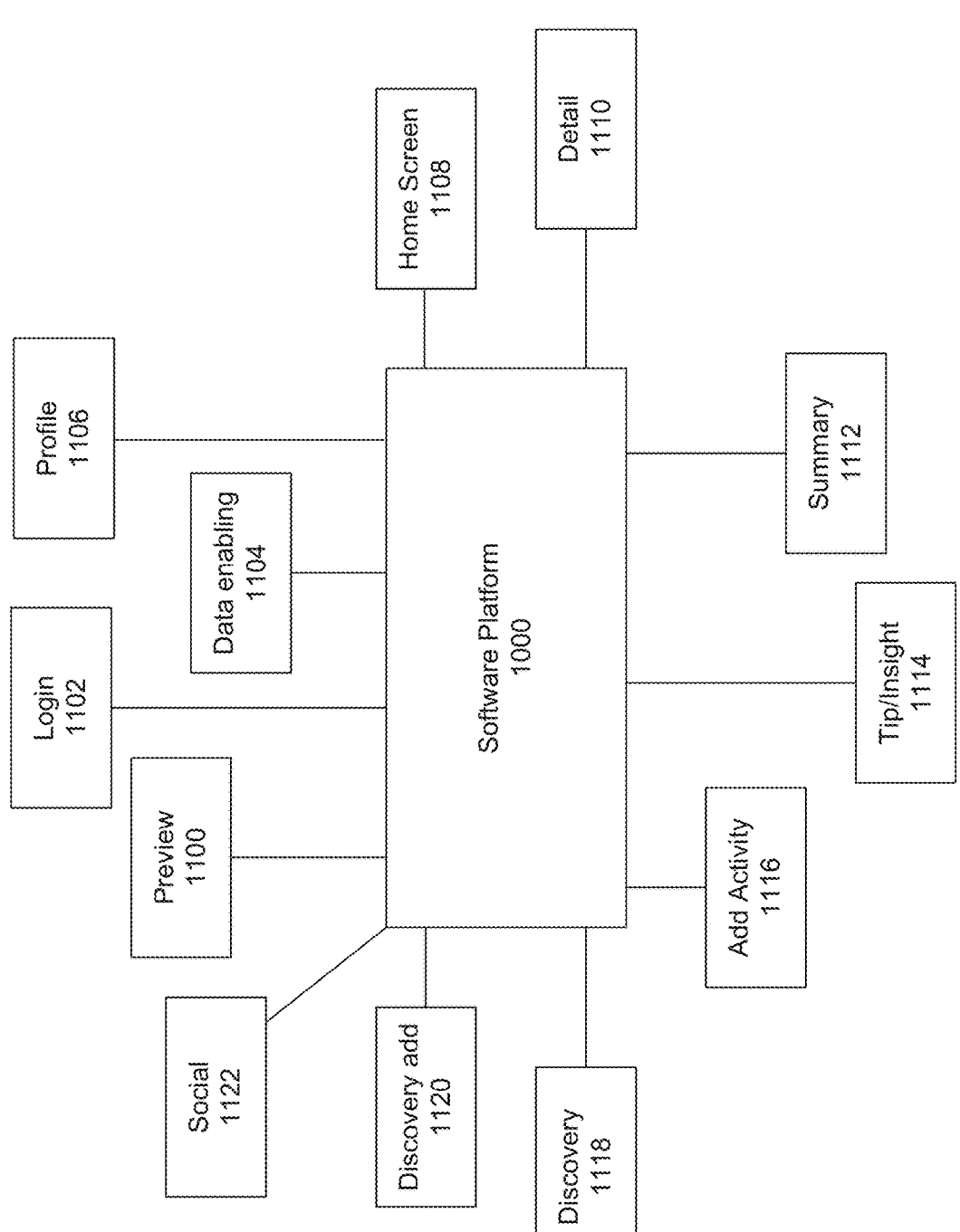
FIG. 3 is a conceptual illustration of a software platform including various software modules according to an example embodiment.

As shown in FIG. 3, software platform 1000 may include several modules, such as preview module 1100, login module 1102, data enabling module 1104, profile module 1106, home screen module 1108, detail module 1110, summary module 1112, tip module 1114, add workout module 1116, discovery module 1118, discovery module 1120, social module 1122, etc.

Various software modules of the present invention may support graphical user interfaces (GUIs) through which an individual 100 can interact with the system 10. A GUI may offer, for example, graphical elements, visual indicators, and/or text to represent information and actions available to the individual 100. The individual 100 may use a physical input device, such as keyboard or scroll ball to interact with the GUI of the electronic device 400. Alternatively, the individual 100 may use a touch screen to interact directly with what is displayed. Various touch screens such as, for example, resistive or capacitive touch screens, may be employed. Those skilled in the art will appreciate that alternative or additional software modules and sub-modules may be implemented in order to provide or extend the described or additional functionalities to the individual 100 using the electronic device 400. For example, the software configuration of software stored on an electronic device 400 may include a device operating system, which may be one of the commercially available mobile phone operating systems such as, for example, BlackBerry OS, iPhone OS, Windows Mobile, Symbian, LINUX, WebOS, or Android. The device operating system may also have an associated application programming interface through which middleware and application programs may access the services of the operating system.

The various modules of the system 10 of the present invention may support GUIs through which an individual 100 can interact with the system 10 using the electronic device 400 just prior to and/or during an activity. As will be appreciated by those of skill in the art, in one embodiment the GUIs may be supported by a mobile device application being run on the electronic device 400. In another embodiment, the GUIs may appear as web pages provided by the server via a website that may be accessible to the individual 100 over the network using a web browser on their electronic device 400. The GUIs may be considered to be part of the methods or systems of the present invention.

In order to access the features of embodiments of the present invention just prior to or during a physical activity, the individual 100 using the electronic device 400 may power on their electronic device 400 if it is not already in a powered up state. In some embodiments, it may be necessary for the individual 100 to manipulate user input controls to enter system 10 mode to access the application software.

In some embodiments, the software app running on the electronic device 400 may also include "hidden" features that cannot be accessed unless unlocked in standard operation of the app without an additional step. In one embodiment, the additional step may include the selection or purchase of a particular health or fitness goal or workout plan, attaining particular personal performance metrics, or activating the app during a specified time period (e.g. on a holiday or particular day of the week) or when the electronic device 400 is being used in a specified geographical location (e.g. in a specific city, park, etc.). In some embodiments, features may be controlled through a "Guest Mode," where information may be saved but a guest individual can only view a limited time history, e.g., one week. In some embodiments, once they create an account, an entire history may become available. In some embodiments, the Guest Mode may restrict the number of discovery experiences that may be active.

After launching the application software, the individual 100 may cause different GUI pages to be provided by different modules by selecting their corresponding icons using user input controls. Additional icons corresponding to sub-modules or program wizards associated with a particular module may pop up or otherwise be displayed to the individual 100 if the individual 100 selects, swipes, or hovers over a module icon with a cursor. All modules may have one or more sub-modules which may be navigated to and from by clicking, swiping, etc. All modules may have one or more sub-modules which may be navigated to and from by clicking, swiping, etc. In some embodiments, the system may allow the individual 100 one of upload photos, videos, medical records, and the like for incorporation into the system.

In some embodiments, there may be an introduction animation for first time use of the system 10. There may also be a setup and tutorial for first time use by the individual 100. Additionally there may be a walkthrough section that may include step-by-step instructions explaining the process of the system and corresponding application. In some embodiments, the system 10 may automatically select the language and localization of the electronic device 400 characteristics, IP address, GPS location, or the like. The system 10 may also allow for default language preferences to be changed in a settings menu.

Figure 5B:
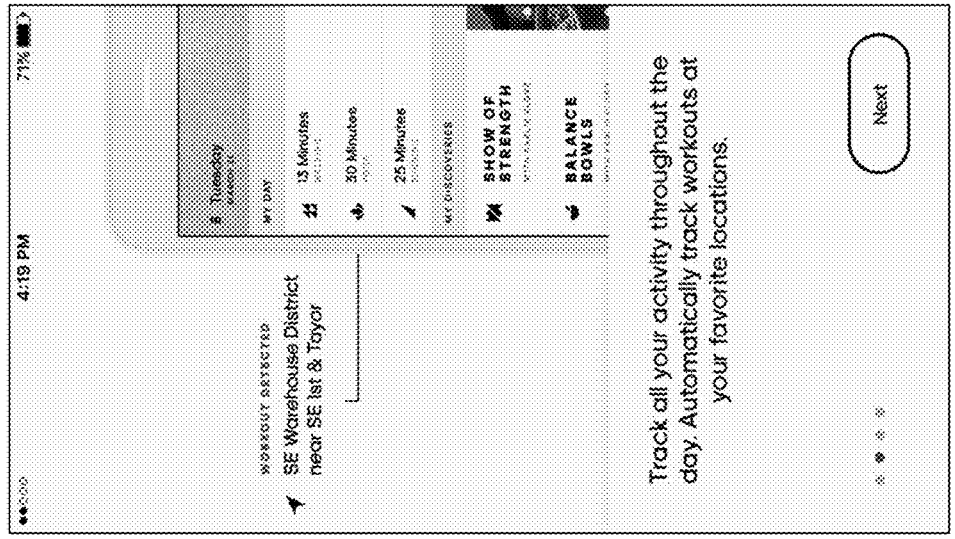
Figure 5A:
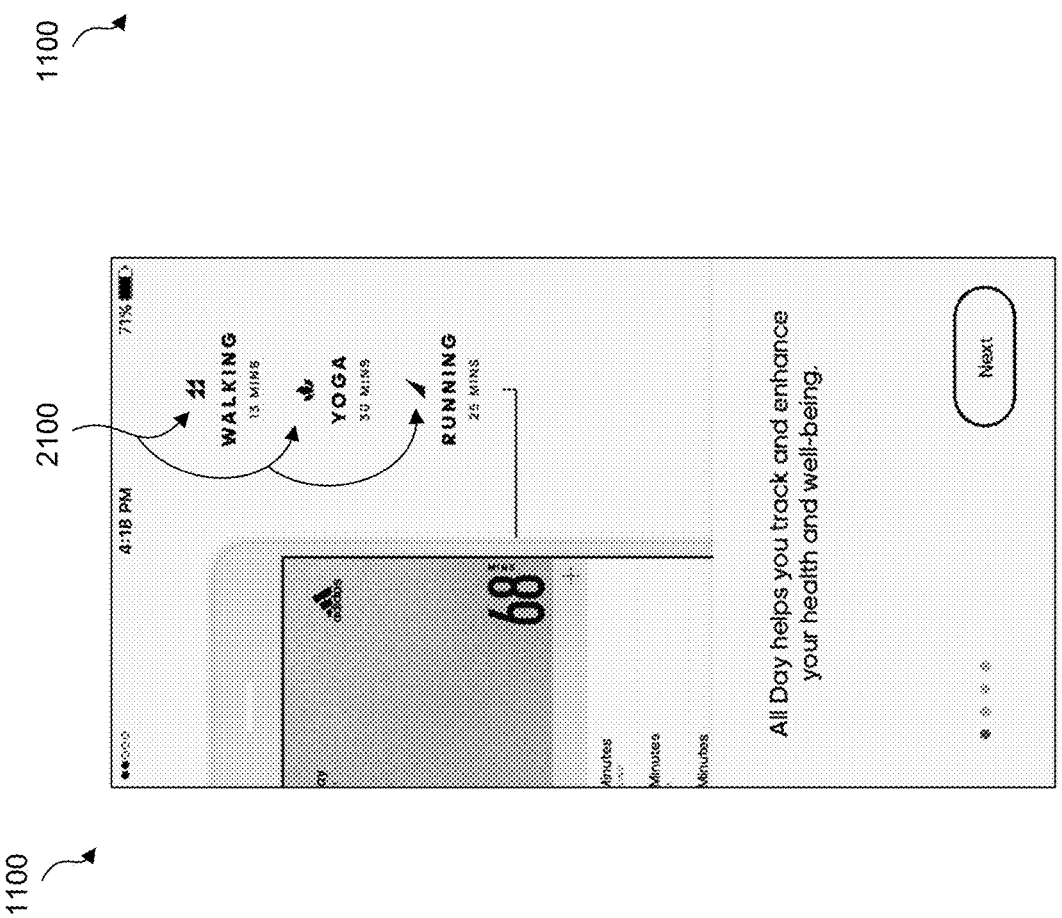
Figure 5D:
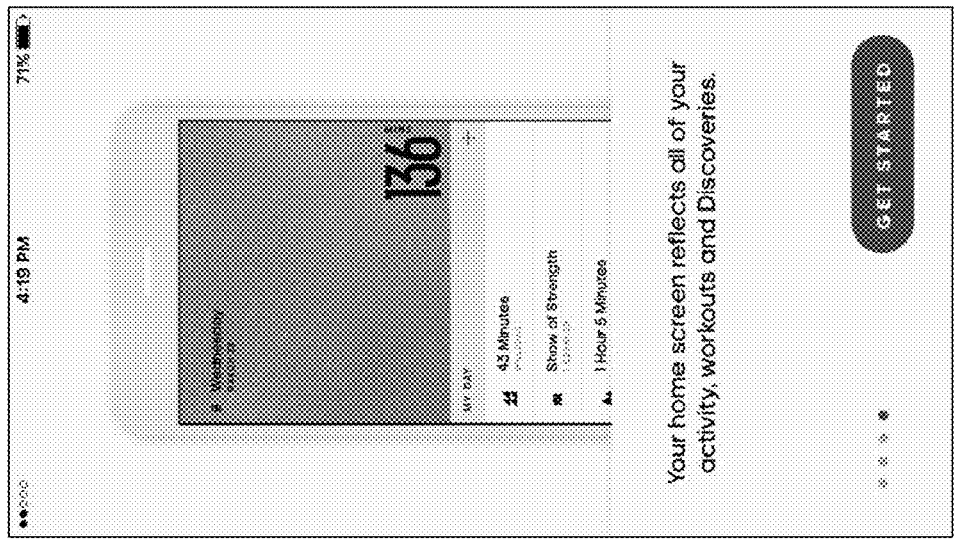
Figure 5C:
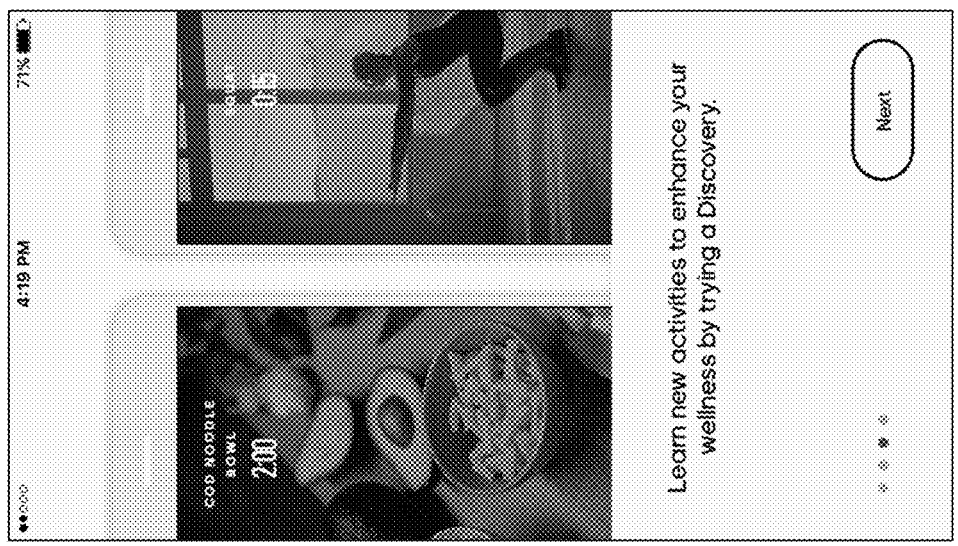

As illustrated in FIGS. 5A-5D, the first time the system application is launched, a preview module 1100 may display general information and representative graphical user interfaces ("GUI") within the software platform. Information as to what the individual may expect, and explanations of representative GUI modules, may be displayed. As illustrated in FIG. 5A, preview module 1100 may show a message to the individual 1100 that the software platform is designed to help track and enhance health and well-being. Representative activity icons 2100 may be displayed, explaining their significance, and suggesting that a feature of the application may combine activities in a summation. As illustrated in FIGS. 5B-5D, other features of the application may be previewed for individual 100, such as workout detection features, discovery features, benefits of learning new activities through discoveries, and the home screen.

FIGS. 6A-6C are exemplary GUI windows that may be provided by the login module 1102. Login module may prompt the individual 100 to, for example, select a preferred language, enter a user name or password to proceed, create an account, retrieve a password, link their electronic device 400 to a web account previously set up via a server. The start module 1102 may have a new user icon which users may select to enter their information. The start module 1102 may present various sub-modules, as illustrated in the FIGS. 6A-63. During subsequent launches of the software application, different modules or sub-modules may be presented to the individual 100 immediately upon launch.

Figure 7B:
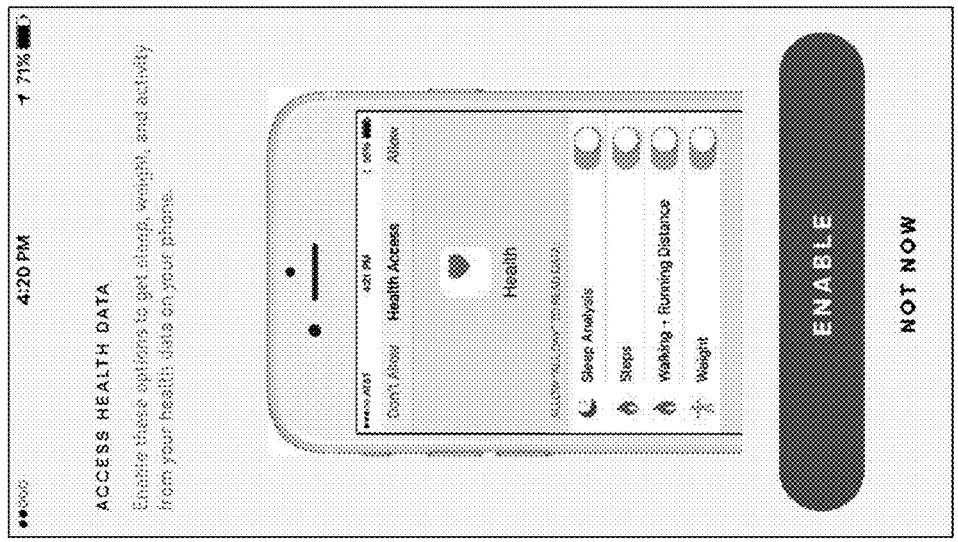
Figure 7A:
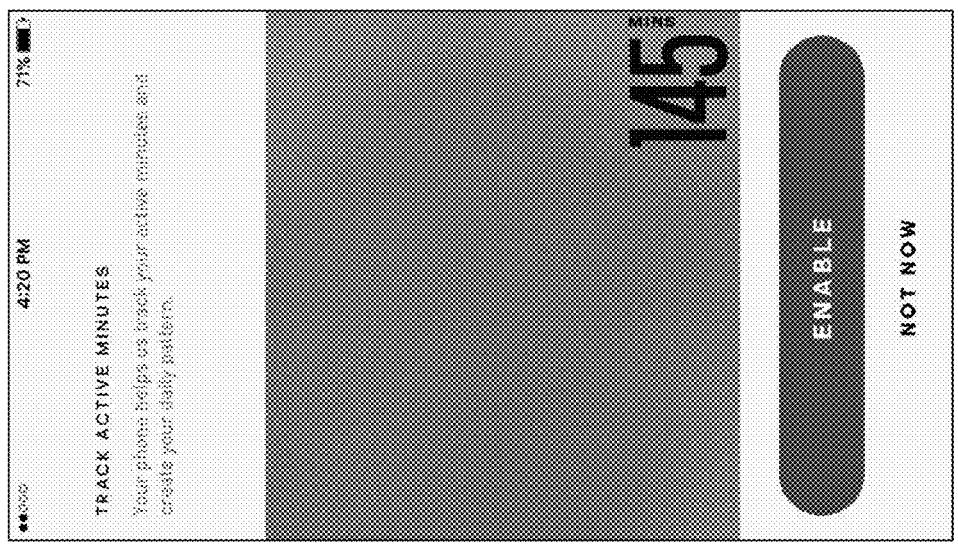

FIGS. 7A-7B are exemplary GUI windows that may be provided by the data enabling module 1104. Data enabling module 1104 may be a sub-module of login module 1102, for example, and appear during a first use of the application. As shown in the figure, data enabling module may suggest to individual 100 to enable tracking of active minutes, which may be achieved directly through electronic device 400, sensor module 102, or the like. As shown in FIG. 7B, data enabling module 1104 may include a sub-module to allow access to additional data, for example, data sources particular to a mobile device operating system, or third party data sources. As shown, these sources may enable data sources such as sleep data, step data, walking/running distance, weight data, and other data for analysis by system 10. In some embodiments, enablement module 1104 may include access to data measured by electronic device 400 (e.g., a mobile phone carried by individual 100). In some embodiments, data may include number of steps, distance walked, active calories (e.g., based on active minutes and workout intensities), location data, weight, nutrition data, hydration data, sleep data (e.g., "asleep data," "in bed" data, etc.), $3^{rd}$ party data from additional devices or applications, etc. In some embodiments, individual 100 may sync software platform 1000 with third party data or devices during on-boarding (e.g., first time startup), or at a later time within the settings of software platform 1000, for example, or the electronic device's 400 settings.

Once individual 100 enables data enabling on software platform 1000, the system 10 may be configured to automatically perform actions related to data collection. In some embodiments, system 10 will then be configured to automatically track or log workouts or athletic activities that individual 100 performs. In some embodiments, system 10 may automatically determine when individual 100 begins a long walk, a run, a bike ride, bike commute, etc. In some embodiments, workouts may include the time it takes individual 100 to walk to and from the workout. In some embodiments, workouts may omit exactly when individual 100 starts or finishes just the running part of a workout, for example. In some embodiments, the workout duration is the start to finish duration, and could include time for breaks, walking, running, cycling, and the like.

In some embodiments, system 10 may automatically log a workout if individual 100 is in a particular location (e.g., a gym, track, arena, athletic complex, etc.) for a prolonged period of time (e.g., about 20-30 minutes). In some embodiments, individual 100 may enable this feature of system 10 by tagging a location while manually adding a workout for the first time. In some embodiments, when individual 100 manually adds a workout, individual 100 will be able to specify that the same workout should be logged when individual 100 visit the same location. In some embodiments, individual 100 may have the option to customize the minimum amount of time for an activity to be logged as a workout. In some embodiments, system 10 may set a default time, e.g., 10 minutes, but individual 100 may alter this threshold.

In some embodiments, system 10 may default to automatically tracking workouts after a period of time, e.g., 10 minutes, which may be altered by individual 100. In some embodiments, system 10 may automatically stop counting a workout if individual 100 takes a break for a predetermined duration. In some embodiments, individual 100 may configure which data source tracks a specific metric, or exclude certain data sources from tracking certain metrics. In some embodiments, additional individual 100 specific settings may be available. For example, individual may be able to set units for length, weight, etc. In some embodiments, individual 100 may be able to configure and enable notifications system 10 will send, e.g., "push notifications" to individual 100 electronic device 400. These notifications may remind individual 100 of important events. These notifications may include tips, insights, workout summaries, new recommended discovery experiences, discovery experience reminders, etc. In some embodiments, individual 100 may configure system 10 permissions to access data such as location, motion, camera, and photo library data. In some embodiments, individual 100 may specify whether downloads (video, audio, photo) happen over cellular data and WiFi or just WiFi.

FIGS. 8A-8C are exemplary GUI windows that may be provided by the profile module 1106. The profile module 1106 may include several icons or indicia corresponding to settings or help features, etc. In some embodiments, individuals may be identified by icons, which may include a gender icon, or a photo of the individual. The icon may also include customer specific info such as how long an individual has been participating in the application, name, and the like. The individual 100 may also be prompted to enter information such as, for example, preferred unit preferences, personal information such as the individual's 100 age, height, weight, gender, sex, contact information, birthday, and/or the individual's 100 desired voice training options. As shown in AA2, the profile module 1106 may include information related to recent activities, and corresponding metrics and icons. Profile module 1106 may include information related to a particular time period, along with data such as daily active minutes, daily steps, daily time slept (e.g., hours), daily active calories, workout data, etc. In some embodiments, profile module 1104 may display weekly averages of one or more of these information types. Profile module 1104 may include a saved tip region 2102. Saved tip region 2102 may include snapshots of previous tips that individual 100 has saved, e.g., for later reference. In some embodiments, GUI windows provided by profile module 1106 may be a single GUI, such that an individual 100 may scroll on a screen to view the various information provided by the GUI. In some embodiments, the information provided by the profile module 1106 may include separate submodules for detailed information. In some embodiments, the system 10 may archive customer information in an acceptable way to allow for more storage room on the electronic device 400 or sensor module 102. Archival may include hard drive storage on site, cloud based storage, server storage, or any other acceptable storage medium.

In some embodiments, profile module 1106 may include an option to delete content, e.g., discovery experience content. In some embodiments, this action deletes discovery media in order to free space on individual's 100 electronic device 400. In some embodiments, this action will not delete the record of the individual's participation in any discoveries. In some embodiments, profile module 1106 may display recent activities, with corresponding icons. In some embodiments, the system 10 may display the top three activities in which individual 100 has been most active over the last four weeks, for example. In some embodiments, the activity with the greatest activity may be displayed at the top of the list. In some embodiments, profile module 1106 may display, for example, the three most recently bookmarked tips, and may include a preview of the text of the tip. In some embodiments, individual 100 may be able to select a tip, and be taken to a display where all of their saved tips may be displayed. Tips may also be deleted by individual 100, or system, for example after an expiration date Profile module 1106, along with other modules, may display a type of athletic activity icon 2100 set that may be used to convey various pieces of information to the individual 100, and from which the individual 100 can select types of activity they will participate in or have participated in. In some embodiments, there may be selection icons for the types of surfaces that the activity will take place on (e.g. road/sidewalk, treadmill, trail, and everywhere). In either case, individuals may be able to select multiple icons to denote intended environment and use. In some embodiments, modules may provide for goal definition, for example athletic goals such as training for a race, or other sporting event, improving individual fitness, simply enjoy running, or the like. Frequency intervals may include for example about 1-2 times per week, about 3-4 times per week, about 5-7 times per week, or the individual doesn't know. Length intervals may include for example about less than about 5 miles per week, about 5-10 miles per week, about 10-20 miles per week, greater than about 20 miles per week, or the individual doesn't know. Examples of intended athletic terrain environments may include roads, track, treadmill, trail, gym, or particular athletic fields designed for a specific sport. In some embodiments, system 10 may allow the individual 100 to select a location of any prior injuries within a certain period of time. The system 10 may include selection icons corresponding to particular body parts. In some embodiments, the system may display a graphical representation of an individual or avatar, and allow the individual 100 to directly select the particular area with a previous injury on the graphical representation. In some embodiments, the system may allow the individual 100 to one of upload photos, videos, medical records, and the like for incorporation into the system and methods.

FIGS. 9A-9D are exemplary GUI windows that may be provided by the home screen module 1108. Home screen module may include a color region 2104. Home screen module may also include links to other modules, such as the profile module 1106, etc. As shown in the FIGS., home screen module 1106 may include data related to active minutes, shown in active minute region 2106. In some embodiments, home screen module 1106 may default to display data related to the current day. In some embodiments, individual 100 may navigate through past days home screens, to see prior days data, including prior days color region 2104. In some embodiments, home screen module includes activity detail regions 2108. Activity detail regions 2108 may show a category of activity for activity minutes. For example, as shown in FIG. 9B, active minutes are shown to be 109 minutes, and activity detail regions 2108 include a 1 hour and 28 minute walking region, and a 21 minute running region, which adds to 109 minutes (the total shown in active minute region 2106. In some embodiments, individual 100 may navigate to a further detail screen upon interacting with activity detail region 2108 within home screen module 1108. In some embodiments, active minutes may be shown as a default, and individual 100 may toggle through various metrics, for example, by tapping the region of the GUI showing the metric. Advantageously, color region 2104 increases individual's 100 interest, as compared to traditional graph forms of metrics.

In some embodiments, when individual 100 completes a discovery session, logs an activity, adds a workout, etc., an icon may appear that represents the corresponding activity. In some embodiments, the icons will populate chronologically as individual 100 perform them throughout the day.

As discussed briefly above, system 10 may track activity details. In some embodiments, active minutes may be tracked by system 10. Active minutes may include a measure of the time individual 100 is active in any way. In some embodiments, walking, running, and cycling are all considered active, regardless of the intensity, for example. In some embodiments, workouts may be added, and considered active, regardless of the intensity. In some embodiments, this may encourage individual simply to be active, no matter what the method, and may contribute positively to behavior change. In some embodiments, active calories may be determined by system 10. For example, activities like an aerobics class, that are harder and more intense burn more calories per minute than activities like walking that are less intense. Active calories may account for intensity, convolved with active minutes, to further inform individual 100. In some embodiments, system 10 may track trends, e.g., such as a active week followed by a low week. In some embodiments, based on the type of activity, a subset of active minutes may be assigned Metabolic Equivalent of Task (MET). In some embodiments, METS are then multiplied by individual's data, such as weight and time of activity to calculate active calories. In some embodiments, system 10 may add in calories as measured from external workouts, third party applications, etc. In some embodiments, calories may include more detailed intensity data like speed, power, or heart rate.

As shown in FIG. 9B, color region 2104 may include a color sub-region 2110. In some embodiments, color sub-region may be a different shade, hue, contrast, brightness, intensity, spectrum, etc. (e.g., color properties) than other portions of color region 2104. In some embodiments, the color properties of color sub-region may vary automatically. For example, if an individual has a single activity counted, the color properties of color sub-region 2110 may be the same as color region 2104. If an individual has multiple activities counted, the color properties of color sub-region 2110 may change, based on type of activities, intensity of activities, duration of activities, whether the individual has participated in a discovery or discovery session, to name a few non-limiting examples. In some embodiments, the color region may serve as a reward or encouragement for individual 100.

In some embodiments, color region is a uniquely deterministic image generation, e.g., for a given user for a given day it serves as a type of "fingerprint". In some embodiments, color region represents the level of physical activity and discovery sessions individual 100 has taken part in that day. In some embodiments, color region may include an animation, such that metrics, color properties, etc. may animate to reflect current totals since individual 100 has reviewed the home screen module 1108. In some embodiments, home screen module 1108 may include a history icon to view data and color regions from past days. In some embodiments, individual 100 can share color regions to various applications (e.g., email, text, social media, etc.) In some embodiments, individual 100 may customize the pattern, color, accent color, etc. used in color region or the system 10 in general.

Figure 27:
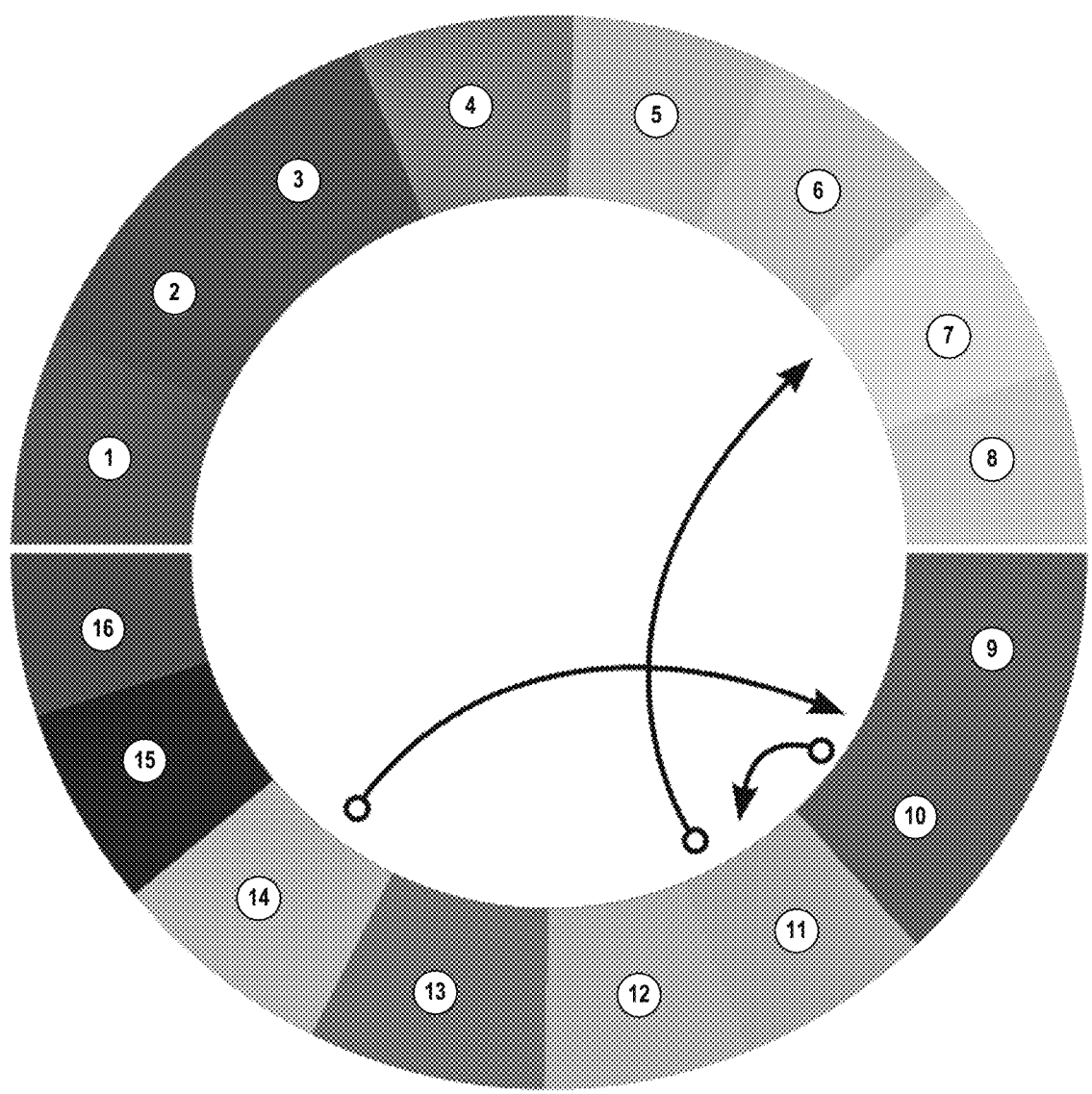
FIG. 27 is an example color wheel according to an embodiment, showing a color progression.
Figure 28D:
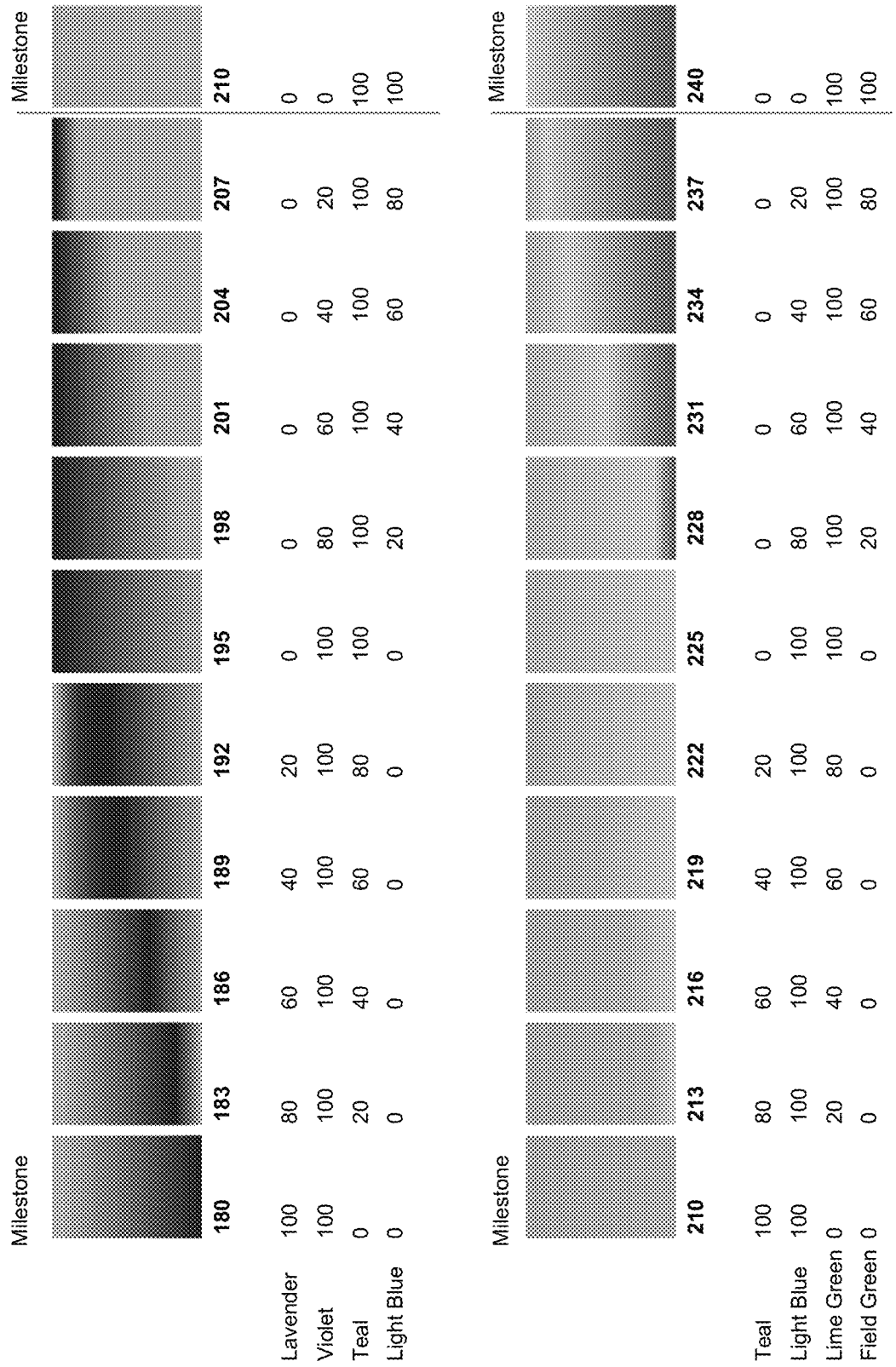
Figure 28E:
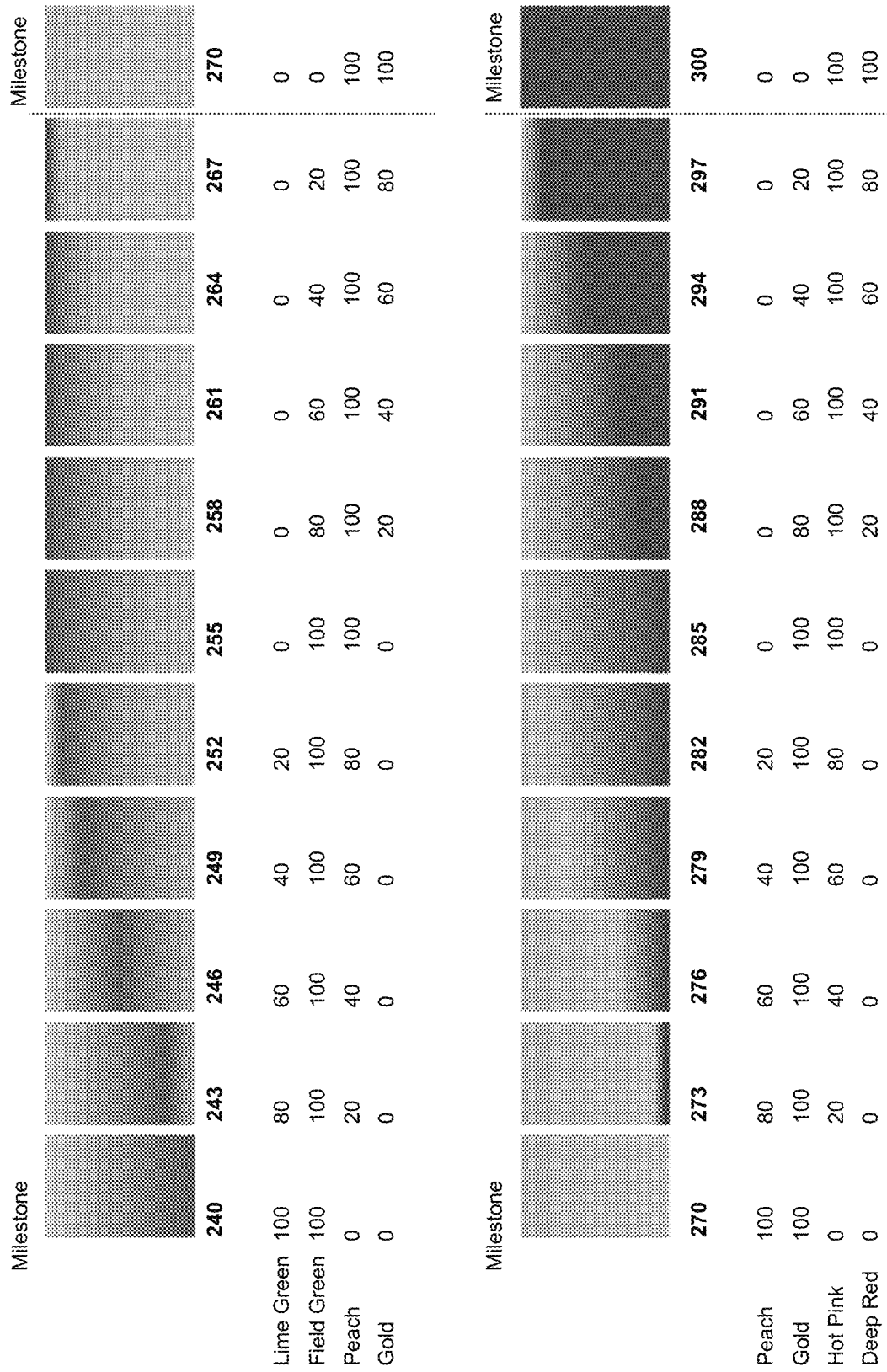
Figure 28G:
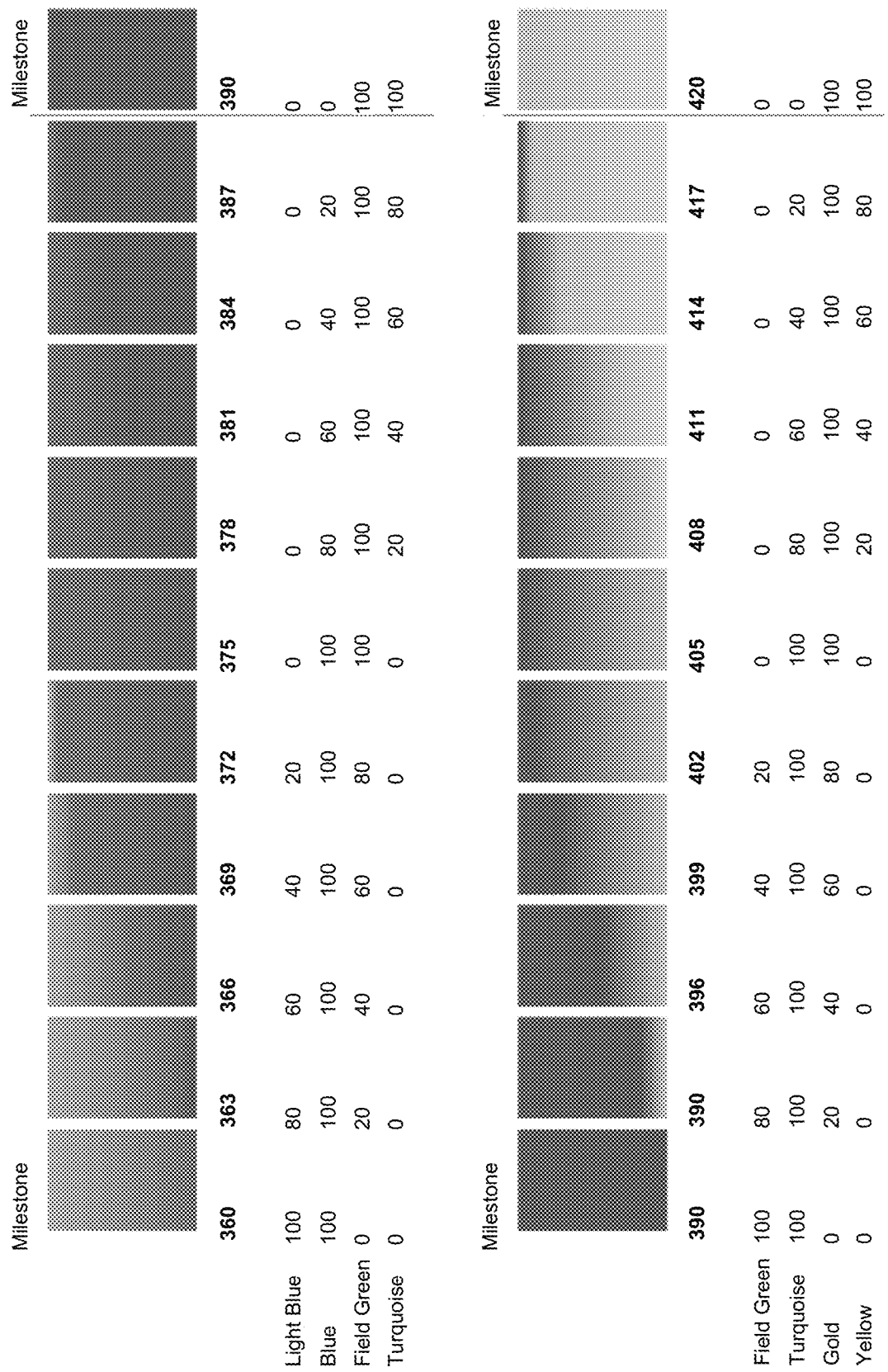
Figure 28I:
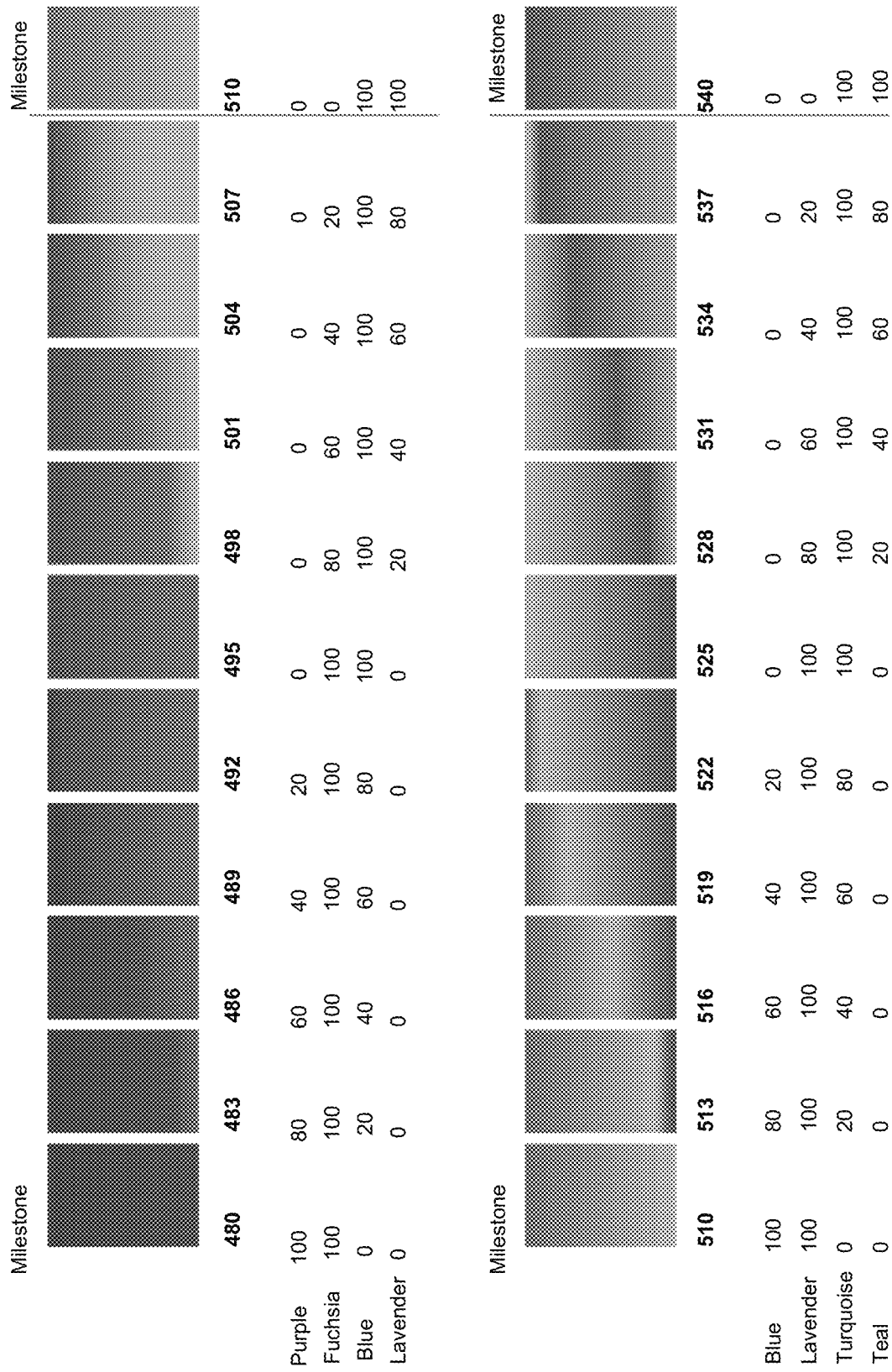

As shown in FIG. 27, color region 2104 or color sub-region 2110 may vary based on a particular color palette or color wheel such as a particular company or brand's palette. In some embodiments, the color region 2104 may vary through a triad-based color progression. In some embodiments, other color palette selections may be included, such as monochromatic colors; complementary colors; split-complementary; achromatic colors; analogous colors; accented analogous colors; tetradic colors; rectangle schemes; square schemes; polychromatic schemes; etc.

In this regard, color region 2104 may have a base starting color, for example a single color such as gray. System 10 may be configured to select the first transition color for the color properties of color region 2104. As color region 2104 changes from the first color to the first transition color based on certain criteria, system 10 may select a second transition color. In some embodiments, the second transition color may be selected, for example, by moving around a color wheel, for example counterclockwise four spots, for example (as shown in FIG. 27). In some embodiments, system 10 may select a third transition color, for example, by moving around a color wheel in the opposite direction, e.g., clockwise a different number of spots, such as one spot clockwise. In some embodiments, system 10 may select a fourth transition color, for example, in the same manner as the selection of the second transition color.

In some embodiments, color region 2104 may display one or more of the base starting color, or transition colors. In some embodiments, color region 2104 is limited to displaying three colors at the most, with different saturation, brightness, gradation, etc., for example displayed in color sub-region 1110.

FIGS. 28A-28I shows example transition colors according to some embodiments. As shown, in some embodiments, the first transition color of color region 2104 may be lavender, and may progress, for example, based on active minutes. As shown, the transitions may be determined by intervals, e.g., every 3 active minutes the color region 2104 may change. As shown, at a time set to "zero", color region 2104 may be 100% gray. At 3 minutes (e.g., active minutes), color region 2104 may be 90% gray, and 10% lavender. These patterns may repeat, e.g., as shown in FIGS. 28A-28I. In some embodiments, the transition points may be different, e.g., a different number of minutes, or be non-time based.

In some embodiments, the color change may increase in acceleration over time, for example a more rapid change in color region 2104 at higher active minute levels. In some embodiments, when a solid color is displayed within color region 2104, this may indicate to individual 100 a milestone has been achieved.

In some embodiments, color sub-region 2110 may correspond to a transition color. In some embodiments, there may be a plurality of color sub-regions 2110 corresponding to transition colors. In some embodiments, color sub-region 2110 may be stationary in color region 2104. In some embodiments, color sub-region 2110 may move within color region 2104, for example within an animation or throughout the day in static color regions 2104.

In some embodiments different individuals 100 may have a different starting color, or color property of color region 2104 depending on a unique customer identifier in the form of a seed, which may be embedded in software platform 1000 at downloading, for example. In this regard, each individual 100 may have a unique deterministic color region change per day in the generation of the color region 2104. This unique color region change may be random or pseudorandom. In some embodiments, the randomization may be repeatable. In some embodiments, color region 2104 may change color properties depending on individual's 100 active minutes over the day.

In some embodiments, the change in color region 2104 may be viewable through an animation, showing color properties changing within color region 2104 throughout a day. In some embodiments, active minutes may be calculated by system 10, and converted to color properties of color region 2104. In some embodiments, additional active minutes may be added for a discovery session completion, and incorporated into the conversion of color properties of color region 2104.

In some embodiments, color properties and color transition of color region 2104 may depend in part on active minutes. For example, for an activity domain discovery, individual 100 may participate in an activity for a given number of minutes. In this regard, system 10 may add these minutes to the active minutes, in order to convert to color properties of color region 2104. In other domains, for example nutrition, rest, and mindset domains, a predetermined additional number of active minutes may be added to the individual's active minutes for converting to color properties of color region 2104, without actually adding any active minutes to the individual's total active minutes for the day (e.g., the addition is solely for the conversion to color properties of color region 2104).

In some embodiments, color properties and color transition of color region 2104 may depend in part on type of discovery, e.g., type of domain such as activity, nutrition, mindfulness, and rest. For example, activity domain discoveries may alter color properties to a particular color or gradient, while a different domain such as nutrition may alter color properties to a different color or gradient (e.g., within color region 2104).

In some embodiments, the additional minutes for discovery sessions or completions may vary based on session or discovery type, for example. In some embodiments, additional minutes for discovery sessions may be uniform, for example, 30 minutes per session or discovery completion. In some embodiments, after a time threshold, e.g., an initial 30 minutes, color region 2104 may include a combination of 2 or 3 colors. In some embodiments, these unique combinations may continue progression throughout a color spectrum or color wheel, and may not repeat for a predetermined number of minutes, e.g., 540 minutes. In some embodiments, after a predetermined number of minutes, the spectrum may begin again with the repeating transition color patterns described above. In some embodiments, the transition colors may be varied based on certain inputs.

In some embodiments, color region 2104 may include different patterns, rather than just color properties, e.g., stripes, checkerboard, polkadots, etc. In some embodiments, color region 2104 may include user defined content, such as a picture or avatar, for example. In some embodiments, individual 100 may customize color region 2104, such as selecting a starting color, color transitions, color palette, or thresholds for changing color region 2104.

In some embodiments, the systems and methods related to the color region 2104 contemplate physical alteration of code or components, such as transforming code or components such that the system or method is physically altered (e.g., creating a new data file, for example). Advantageously, the solutions provided herein are rooted in technology, e.g., computer technology, and overcome problems related to physiological monitoring for example and color spectrum generation, for example. These solutions are unique to technological realms such as data processing, e.g., image or color spectrum processing and display. The systems and methods described herein additionally may contemplate additional elements beyond data relationships, such that the solutions tie process advantages to a particular device and increase performance of such a device (e.g., increasing processing efficiency, resolution for location based features, etc.).

As shown in FIG. 9D, in some embodiments, home screen module 1108 may include discovery tile 2112. In some embodiments, the tiles 2112 may indicate an action for individual 100 to take or an event individual 100 should be aware of. In some embodiments, the tiles 2112 may include discovery experiences that individual 100 is enrolled in. In some embodiments, tiles are organized vertically, for example, by level of importance and time of enrollment. In some embodiments, tiles 2112 may be interacted with by individual 100, for example to add to a "favorites" list, obtain more information, begin a discovery experience session, download content for a discovery, etc. In some embodiments, home screen module 1108 may include discovery navigation element, which may be configured to display a general suggestion of a discovery to individual 100. In some embodiments, discovery navigation element may display discovery experiences the individual 100 is currently participating in, with content related to the discovery experiences, or a navigation function to navigate to a particular discovery experience. In some embodiments, discoveries may be limited to a number of sessions, or a period of time, for example. In some embodiments, discovery ending may be user defined, e.g., whether a user is happy with the result or progress through a discovery, or reaches a predetermined level of a metric the discovery is designed to affect.

Figure 10A:
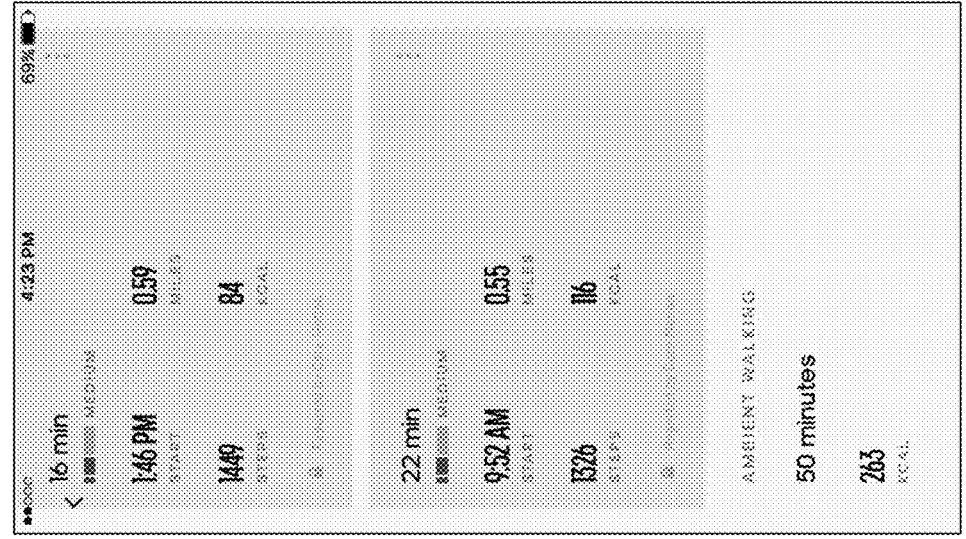
Figure 10B:
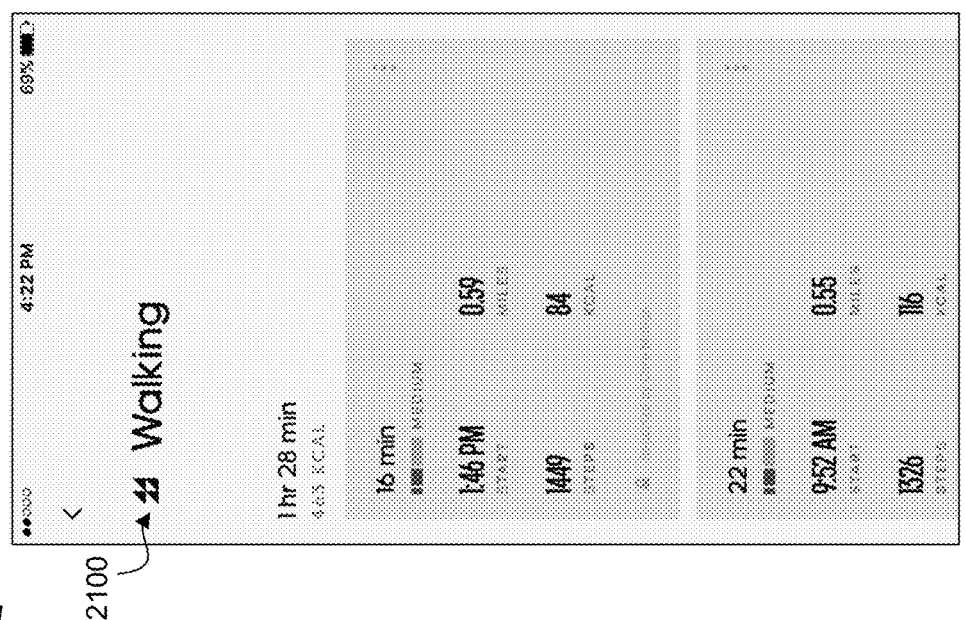

In some embodiments, home screen module 1106 may be interacted with to navigate to detail module 1110, as shown in FIGS. 10A and 10B. In some embodiments, individual 100 can interact with a displayed activity (tap the icon 2100 or description, for example), and the specific activity will be shown on a respective detail module or sub-module. In some embodiments, detail module 1110 may display all workouts detected for the specific activity. In some embodiments, detail module 1110 will include additional information, such as total duration, session duration, intensity level, activity start or end time, distance, calories, total calories, step count, etc. In some embodiments, workout durations include a majority of the activity, but may also include time for breaks, or other activities. In some embodiments, "Ambient" Walking or Running minutes are shown within the Walking and Running detail screens. "Ambient" minutes include walking or running minutes that have not been included within a workout, e.g., the walking and running that individual 100 does in small amounts throughout a day.

Figure 11:
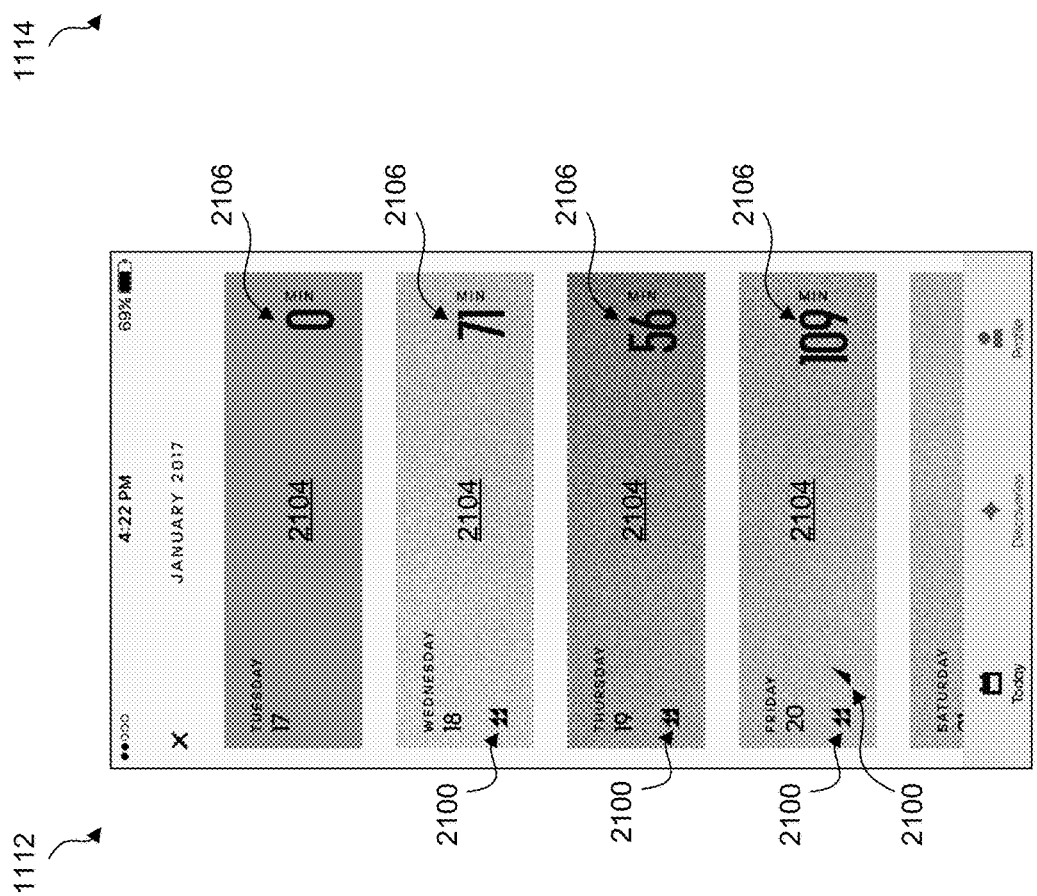

In some embodiments, system 10 may include a summary module 1112. As shown in FIG. 11, summary module 1112 may show a summary of color regions 2104, or information related to prior days activity. As shown, a smaller representative version of color region may be displayed, along with active minutes. In some embodiments, summary module 1112 may also include icons representative of certain activities individual 100 participated in on that day.

Figure 12:
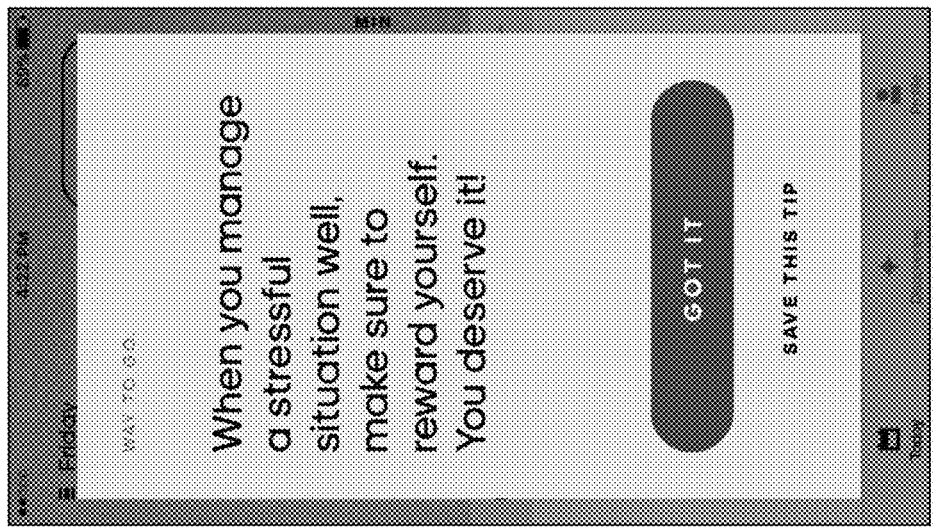

Turning to FIG. 12, an exemplary GUI window of a home screen module 1108, with a tip or insight module 1114 GUI overlaid in a pop-up manner is shown. In some embodiments, tip module 1114 may be a sub-module, or a standalone module. In some embodiments, individual 100 may interact with the GUI to save the tip for later review.

In some embodiments, system 10 may include an add activity/add workout module 1116, with exemplary GUI windows as shown in FIGS. 13A-13C. As shown, add workout module 1116 may be navigated to from home screen module 1108. Add workout module 1116 may include, for example, recent activities added, or popular workouts for an individual to select. As shown, certain activities may include icons representative of the activity, e.g., a simplified mountain icon for a hiking activity, a flower icon for yoga activity, a simplified bicycle for cycling, etc. As shown, add workout module 1116 may be used to select a type of workout, name of workout, date of activity, time of activity, duration of activity, intensity of activity, location of activity, etc. In some embodiments, individual 100 may be able to search for particular workouts, e.g., through a network, or internet, for example. In some embodiments, intensity of activity may specify a general intensity for the whole workout, such as "Low", "Medium", "High". In some embodiments, these intensities will be used to help system 10 daily calories, or daily active calories. In some embodiments, the intensities may be used to track difficult and easy days. In some embodiments, the activities may be editable, such as through swiping or tapping on the representative GUI, and may edit the content described. In some embodiments, an individual 100 may not be able to edit activities that are auto-tracked via system 10.

Figure 14:
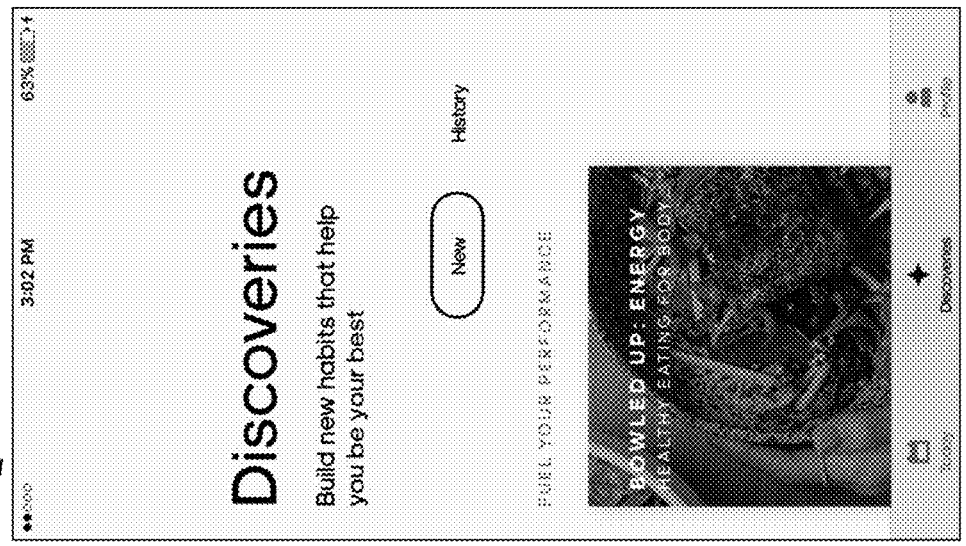

FIG. 14 shows an exemplary GUI window of a discovery module 1118. In some embodiments, software platform 1000 may include a discovery module 1118. Individual 100 may opt to participate in a "discovery" or "discovery experience". As used herein, discoveries may be time bound experiences, that an individual 100 would like to participate in, for example to make progress towards a goal. Discoveries, as used in system 10, may be activities that individual 100 can perform in order to see what works best to help individual 100 reach their goals. Discoveries may be configured such that it encourages individual 100 to try new things and learn how to build new habits. In some embodiments, discoveries may be related to domains such as movement (e.g., activity, athletics, flexibility, etc.), nutrition (e.g., healthy food, healthy hydration, weight goals, etc.), mindset (e.g., mindfulness, awareness, mental state, decreasing stress, etc.), and rest (e.g., healthy resting habits, balance in activity and rest, etc.).

Figure 15:
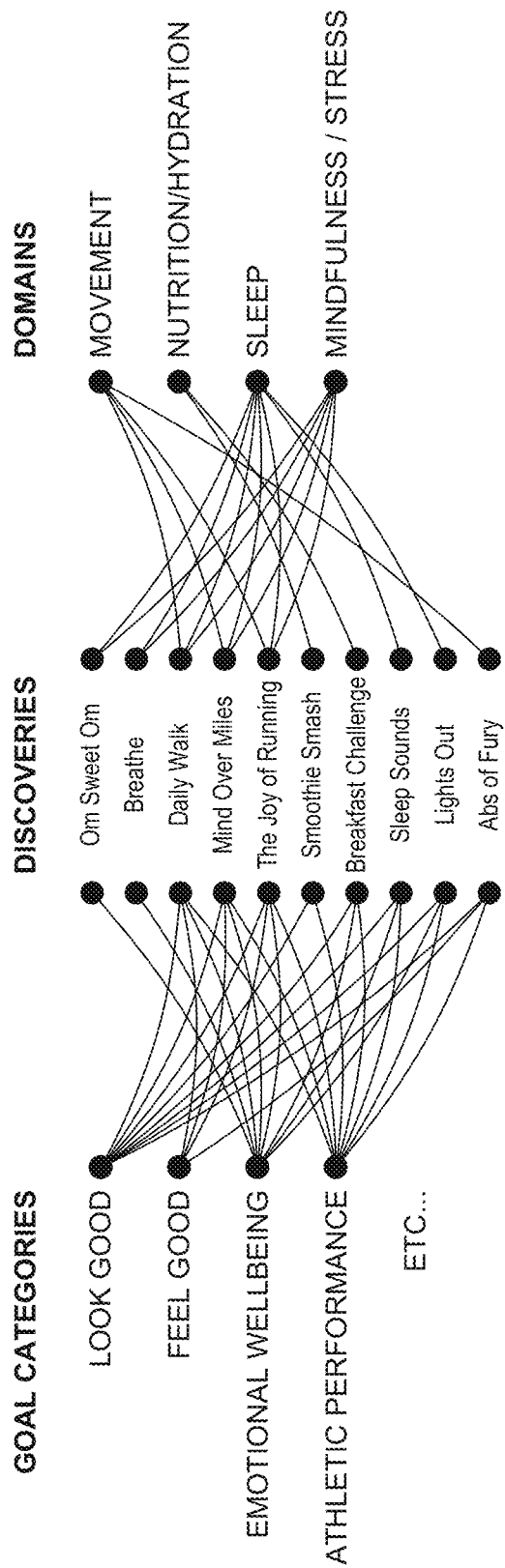
FIG. 15 shows a conceptual relationship illustrating mapping of discoveries to domains and/or goal categories according to an embodiment.

As shown in FIG. 15, system 10 may include rules or algorithms for suggesting or selecting discoveries. For example, discoveries may be mapped to goal categories (e.g., look good, feel good, emotional wellbeing, athletic performance), categories of domains such as movement (e.g., activity, athletics, flexibility, etc.), nutrition (e.g., healthy food, healthy hydration, weight goals, etc.), mindset (e.g., mindfulness, awareness, mental state, decreasing stress, etc.), and rest (e.g., healthy resting habits, balance in activity and rest, etc.), TTM states, etc. In some embodiments, discoveries may be stored in a database, such that discoveries may be looked up according to one or more matching category maps. Example discoveries mapped with appropriate domains or goal categories, along with descriptions of representative sessions follow.

For example, for an activity domain discovery directed towards strength, system 10 may define sessions of beginner, intermediate, and advanced sessions, with corresponding strength exercises for each sessions. In some embodiments, system 10 may include public relations or media integration with social media influencers to encourage strength training.

As another example, for an activity domain discovery, system 10 may define High Impact Interval Training (HIIT) sessions. In some embodiments, the discovery may include sessions related to measuring and tracking body fat; practicing movements and techniques to prepare for HIIT sessions; and daily sessions of HIIT. In some embodiments, system 10 may provide additional tips and advice regarding HIIT, due to the nature of HIIT requiring specific rest cycles. In some embodiments, electronic device 400 may provide physiological feedback during interval sessions.

As another example, for an activity domain discovery, system 10 may include a discovery related to how or why specific yoga poses can increase energy at different times during the day. For example, system 10 may include sessions related to morning poses, which may be designed with gradual exercises that ease a user into the day from sleep; afternoon poses, which may be designed to stimulate the brain, increase alertness, and reduce drowsiness; and weekly rhythms, which may be designed to help a user optimize effectiveness of a yoga routine by performing yoga at different times of the week.

As another example, for an activity domain discovery, system 10 may include a discovery related to how incorporating yoga into training can improve running ability. For example, system 10 may include a session on how yoga can boost a running exercise by elongating muscles, aiding in recovery from injury, and preventing injury. For example, system 10 may include sessions related to breathing, including practicing diaphragmatic breathing to improve aerobic endurance to increase running distances; warm up, including active yoga poses, including crescent lunge, warrior, and squats; and cool down, including passive stretches, such as half splits, supine four, and forward folds. In some embodiments, electronic device 400 may provide feedback on proper form, breathing, etc., through various physiological sensors described herein.

As another example, for an activity domain discovery, system 10 may include a discovery related to how to effectively link new and healthy habits into existing routines. For example, system 10 may include sessions related to stacking categories, which can help a user learn about common life categories to pair habits from. Examples of categories to stack may include for example, productivity, relationship, finances, and leisure. The system 10 may include sessions related to providing concrete examples from each category to identify linking habits that can be performed in a short amount of time, e.g., about two minutes or less. The system 10 may include sessions related to the exploring popular habits that others have used to create lasting behavior change, integrating a social platform or communication platform, for example through electronic device 400. The system 10 may include sessions related to customizing stacking categories.

As another example, for an mindfulness domain discovery, system 10 may include a discovery related to how traditional meditation techniques can change physiology and brain waves, increase cognitive abilities, and altering mood and emotions. For example, the system 10 may include sessions related to focusing attention by providing methods for bringing a single object into a user's awareness. For example, the system 10 may include sessions related to open monitoring and processing of a user's ongoing emotional and cognitive state without manipulating or controlling the user's emotional or cognitive state. For example, the system may include sessions related to calming and restorative exercises. In some embodiments, physiological sensors may be added to the discovery, e.g., to measure brainwaves, respiratory or cardiac parameters, etc., to provide additional feedback (e.g., through electronic device 400).

As another example, for a mindfulness domain discovery, system 10 may include a discovery related to how doing small or impromptu favors and treating others with more compassions can improve individual's 100 self-regard. For example, the system 10 may include sessions related to altering dialogue or reaction in ambiguous, stressful, or confrontational situations. For example, the system 10 may include a session related to changing driving habits to reduce stress or confrontational driving habits, such as allowing people in the crosswalk to pass, allowing another driver to merge, and not using the horn. For example, the system 10 may include a session related to doing kind favors for others, such as paying public transportation fare for someone else, holding the door for a predetermined number of people each day, letting someone pass you in line, and complimenting a predetermined number of people each day. In some embodiments, this discovery may make use of particular tips or insights, e.g., location-aware tips if individual 100 is in a populous area.

As another example, for a mindfulness domain discovery, system 10 may include a discovery related to how self-affirmation may be a powerful tool for managing future emotions and self-regard. For example, the system 10 may include a session related to picturing oneself in desirable situations and providing confidence and inspiration for achieving those situations. For example, the system 10 may include a session related to growing personal characteristics upon which self-affirmation is based. For example, the system 10 may include a session related to outlining how to activate positive self-affirmation before stressful or high intensity situations. The system 10 may include affirmations delivered by others to provide a sample of how self-affirmation is achieved. In some embodiments, this discovery may include physiological or biometric feedback sensors, e.g., within electronic device 400. For example, device 400 may include a heart rate sensor to determine when individual 100 may be experiencing stress, and provide a tip or insight based on this determination.

As another example, for a mindfulness domain discovery, system 10 may include a discovery related to how to incorporate silence into a routine to improve focus, creativity, and energy, and prevent disease. For example, the system 10 may include a session related to challenging a user to find a short amount of time, e.g., 2 minutes to sit in absolute silence, and during those 2 minutes to listen deeply and count every type of sound heard. For example, the system 10 may include a session related to finding a comfortable location where the user will close his or her eyes and process and appreciate the unique sounds of the environment at that location. For example, the system 10 may include a session related to challenging a user to work toward a personal record for length of silence. In some embodiments, sensors may be used to monitor individual 100 through the mindfulness exercise, and provide tips or feedback based on the sensed data.

As another example, for a nutrition domain discovery, system 10 may include a discovery related to exploring food options from various regions, diets, or preparation methods. For example, the system 10 may include a session related to trying different types of food in the form of a meal prepared in a bowl, such as macro bowls that focus on adding fermented foods; or vegetarian or vegan bowls that focus on fruits, vegetables, grains, and other toppings. For example, the system 10 may include a session related to pairing various food options with third party vendors at locations along popular exercise and fitness routes and locations. In some embodiments, electronic device 400 may utilize location based features to provide tips at particular locations, e.g., notifying individual 100 that a particular vendor is close by and that offers a food item related to the discovery.

As another example, for a nutrition domain discovery, system 10 may include a discovery related to how utilizing a coloring system to explore and add new, nutrient rich foods to a daily diet. For example, the system 10 may include a session related to providing a different color of food to each day. For example, one day of the week may include red foods, such as strawberries and beets. For example, another day of the week may include green foods, which are low in calories and carbohydrates. For example, another day of the week may include yellow foods, such as lemons, plantains, pineapple, star fruit, yellow winter and summer squash, which can aid digestion, skin health, and bone and teeth health. For example, another day of the week may include brown foods, such as whole grains, unbleached rice, flour, bread, and other grains that provide strong disease prevention. For example, another day of the week may include blue or purple foods, such as eggplant, cabbage, endive, and asparagus, which my aid immune system function and support eye and vision quality. For example, the system 10 may include a session related to partnering with various third parties, such as grocery stores or food markets, to provide various colors of food throughout a week. In some embodiments, electronic device 400 may utilize location based features to provide tips at particular locations, e.g., notifying individual 100 that a particular vendor is close by and that offers a food item related to the discovery.

As another example, for a nutrition domain discovery, system 10 may include a discovery related to how increasing water consumption may improve physiological parameters, such as metabolism, sleep, and mood. For example, the system 10 may include a session related to assessing target water intake. For example, the system 10 may include a session related to how warm water may be easier for the body to absorb. For example, the system 10 may include a session related to how more water intake may flush toxins and improve skin quality. For example, the system 10 may include a session related to adding different fruits to basic water drinks to add healthy flavors to drinks. In some embodiments, electronic device 400 may provide feedback, such as a fluid level in a vessel with a fluid sensor, and may provide tips or insights to individual 100 based on the level of fluid in the vessel.

As another example, for a nutrition domain discovery, system 10 may include a discovery related to examining habits that a user may enjoy but which are unhealthy, such as overeating, drinking, smoking, or remaining sedentary or inactive, and providing a method to take control of those habits. For example, the system 10 may include a session related to listing unhealthy habits and describing what impact those unhealthy habits have on other aspects of behavior or health. For example, the system 10 may include a session related to tracking unhealthy habits to understand the frequency and context of those unhealthy habits. For example, the system 10 may include a session related to creating a consequence for the unhealthy habit, for example, performing a specific exercise each time the unhealthy habit occurs, or exchanging the unhealthy habit for a more healthy option. In some embodiments, electronic device 400 may provide feedback, e.g., location based feedback if it is determined that individual 100 is in a location likely to be engaging in an unhealthy activity, e.g., a smoking area. In some embodiments, electronic device 400 may be a wearable device, and may detect motions associated with an unhealthy activity, e.g., smoking. Tips or feedback may be provided to individual 100 based on these detections.

As another example, for a nutrition domain discovery, system 10 may include a discovery related to building breakfast into a daily routine. For example, the system 10 may include a session related to prompting a user to incorporate a simple food, such as a banana, orange, or other fruit. For example, the system 10 may include a session related to providing a timer or audio track that reminds a user to slow down a morning routine to include eating breakfast, and providing a healthy breakfast recipe with the timer or audio track. For example, the system 10 may include a session related to providing quizzes that test a user's knowledge of breakfast foods and help a user learn to make healthy options.

As another example, for a rest domain discovery, system 10 may include a discovery related to how good sounds can affect sleep quality and in turn affect a person's health and well-being. For example, the system 10 may include a session related to providing information about how background sounds can affect sleep quality and how white noise can mask distracting sounds. For example, the system 10 may include a session related to providing various audio tracks that help minimize distracting noises and aid in relaxation to improve sleep quality. In some embodiments, electronic device 400 may monitor sleep patterns or quality of individual 100 and provide tips or insights based on the detected data.

As another example, for a rest domain discovery, system 10 may include a discovery related to how environmental factors can affect conditions for falling asleep and staying asleep, including providing information on how a body prepares for sleep and behaves during sleep. For example, the system 10 may include a session related to creating a bedtime routine in order to prompt the body to start preparing for sleep. For example, the system 10 may include a session related to providing a reminder to reduce the room temperature to a maximum predetermine temperature, for example 65 degrees Fahrenheit. For example, the system 10 may include a session related to taking a warm bath 3 times per week before bed to help the body cool more quickly. For example, the system 10 may include a session related to reducing or eliminating caffeine after a specific time of day, for example 2:00 pm. In some embodiments, electronic device 400 may monitor sleep patterns or quality of individual 100 and provide tips or insights based on the detected data.

As another example, for an activity or rest domain discovery, system 10 may include a discovery related to how a pre-sleep yoga routine can aid in falling asleep and overall sleep quality. For example, the system 10 may include a session related to beginner level poses that focus on poses with relatively short durations, such as Child's Pose (Balasana), Corpse Pose (Savasana) and Reclining Butterfly (Supta Baddha Konasana). For example, the system 10 may include a session related to intermediate level poses that increase variations and pose durations, such as Legs Up The Wall Pose (Viparita Karani) and Left Nostril Breathing (Surya Bhedana). For example, the system 10 may include a session related to advanced level poses such as Plow Pose (Halasana) and Big Toe Pose (Padangustiasan). In some embodiments, if individual 100 is enrolled in multiple discoveries related to a similar subject (e.g., yoga), system 10 may leverage feedback and progress from one discovery, and apply data or techniques to the other discovery. In some embodiments, tips or insights may be provided for a plurality of discoveries at the same time.

As another example, for an activity domain discovery, system 10 may include a discovery related to how treadmill workouts can improve indoor exercise routines. For example, the system 10 may include a session related to a treadmill workout from a celebrity trainer. For example, the system 10 may include a session related to a 45-minute fat burning interval workout. For example, the system 10 may include a session related to a 25 to 50 minute session modeled after outdoor routes and hills. In some embodiments, system 10 may communicate with an exercise machine, e.g., a treadmill, to retrieve data directly from the treadmill to use within the system 10.

As another example, for an activity domain discovery, system 10 may include a discovery related to providing a Barre workout experience. For example, the system 10 may include a session related to an at-home Barre workout experience that can be performed without equipment or a gym membership. For example, the system 10 may include a session related to explaining common mistakes people make when first attempting a Barre workout experience. In some embodiments, electronic device 400 may utilize location based features to provide tips at particular locations, e.g., notifying individual 100 that a particular vendor is close by and that offers a class, activity, or equipment, related to the discovery. Other particular workout experiences may be provided, e.g., a Pilates workout experience; a spinning or cycling workout experience.

As another example, for an activity domain discovery, system 10 may include a discovery related to incorporating stretching into a fitness routine to improve range of movement and compliment other fitness goals. For example, the system 10 may include a session related to providing daily stretching goals to help a user achieve various stretching goals, such as touching toes. For example, the system 10 may include a session related to prompting a user to stretch during various breaks, such as commercial breaks. For example, the system 10 may include a session related to creating a stretching routine using household items, such as a broom stick, to aid in stretching. For example, the system 10 may include a session related to creating stretches that can be discreetly incorporated into normal activities. In some embodiments, electronic device 400 may utilize location based features to provide tips at particular locations, e.g., notifying individual 100 that a particular location is good for particular types of stretches, or encouraging a user to take a photo of themselves stretching in a particular location. In some embodiments, if individual 100 is enrolled in multiple discoveries related to a similar subject (e.g., stretching, yoga, etc.), system 10 may leverage feedback and progress from one discovery, and apply data or techniques to the other discovery. In some embodiments, tips or insights may be provided for a plurality of discoveries at the same time.

As another example, for an activity domain discovery, system 10 may include a discovery related to providing an audio session to guide a running exercise that prompts a runner to maintain an effective mix of activity and rest during the running exercise. For example, the system 10 may include a session related to providing an audio track that prompts a user run, stop, and take timed walks, during the running exercise. For example, the system 10 may include a session related to providing an audio track that mixes the style, pace, and duration of various components of a running exercise. The system 10 may provide downloadable playlists from third parties or other users. In some embodiments, electronic device 400 may utilize location based features to provide tips at particular locations, e.g., notifying individual 100 that a particular location is good for a particular running exercise, or encouraging a user to take a photo of themselves running in a particular location.

As another example, for an activity domain discovery, system 10 may include a discovery related to providing a social workout experience. For example, the system 10 may include a session related to a trainer providing guidance throughout a workout. For example, the system 10 may include a session related to a real-time global workout in which trainers lead scaled session synced with music from a remote live performance. For example, the system 10 may provide workout parties tied to various social locations or events, e.g. through location based features within electronic device 400.

As another example, for an activity domain discovery, system 10 may include a discovery related to integrating daily activities into weekly exercise goals, such as shopping or commuting. For example, the system 10 may include a session related to biking, running, or walking to work, e.g., 3 times per week. In some embodiments, the system 10 may include a session related to walking, biking, or running to a location instead of driving, e.g., 2 times per week. For example, the system 10 may include a session related to allocating a lunch break, or other break from work to walking or exercising. For example, the system 10 may integrate these sessions into various localized places or events, such as city-based bike share programs. In some embodiments, electronic device 400 may utilize location based features to provide tips at particular locations, e.g., notifying individual 100 that a particular route is close to bike share programs, or a nearby park to take a walk.

As another example, for an activity domain discovery, system 10 may include a discovery related to integrating household chores into weekly exercise goals, such as gardening or cleaning. For example, the system 10 may include a session related to pulling weeds for, e.g., 15 minutes, 3 times per week; sweeping for 15 minutes, 3 times per week; planting something, including digging a hole; composting, including turning the compost 3 times per week; mulching or raking grass and leaves. In some embodiments, individuals 100 may be prompted to take a photo of themselves engaging in the activity, to integrate a social aspect of the discovery.

As another example, for an activity domain discovery, system 10 may include a discovery related to integrating child care into weekly exercise goals. For example, the system 10 may include a session related to carrying a child for, e.g., 30 minutes per day, 3 times per week; lifting a child 15 times per day; biking with a child a carrier 2 times per week; or push a child 50 times on a swing, 2 times per week.

As another example, for an activity domain discovery, system 10 may include a discovery related to integrating social activities into weekly exercise goals. For example, the system 10 may include a session related to dancing for 30 minutes, 2 times per week. For example, the system 10 may include a session related to varying dancing styles or music tempo. In some embodiments, individuals 100 may be prompted to take a photo of themselves engaging in the activity, to integrate a social aspect of the discovery.

As another example, for an activity domain discovery, system 10 may include a discovery related to integrating pet care into weekly exercise goals. For example, the system 10 may include a session related to taking a dog for a longer walk in the mornings; following a different route while walking a dog every third day; and walking the perimeter of a dog park 3 times each visit. For example, the system 10 may include partnerships with third parties, such as local humane societies, e.g., through location based features of electronic device 400. In some embodiments, individuals 100 may be prompted to take a photo of themselves engaging in the activity, to integrate a social aspect of the discovery.

As another example, for an activity domain discovery, system 10 may include a discovery related to increasing standing time to improve long term health. For example, the system 10 may include a session related to providing alternative habits at work to increase standing time, such as visiting a restroom on a different floor or using a copy machine that is farthest away on the floor. For example, the system 10 may include a session related to providing alternative habits at home to increase standing time, such as standing and completing a simple activity during television commercial breaks. For example, the system 10 may include partnerships with third parties, such as organizations involved in cardiac care.

As another example, for an activity domain discovery, system 10 may include a discovery related to leg strengthening and flexibility to help a user achieve a split. For example, the system 10 may include a session related to warming up the lower body, preparing the lower body by stretching and/or strengthening, holding a max split for 10 seconds longer than the previous max split. For example, the system 10 may include education related to nontraditional models, which can be more accessible and encouraging. As another example, for an activity domain discovery, system 10 may include a discovery related to encouraging a user to engage in an activity that is perceived as difficult or impossible. For example, the system 10 may include a session related to encouraging the user to engage in hand stands, hula, or cartwheels.

As another example, for an activity domain discovery, system 10 may include a discovery related to building a personal marathon or race by using local elevation and terrain that mimics world-famous runs and races. For example, the system 10 may include a session related to exploring characteristics of world-famous marathon courses and aligning the course with a user's abilities. For example, the system 10 may include a session related to approximating running the number of corners in a user-selected marathon in two running sessions. For example, the system 10 may include a session related to providing audio cues to punctuate key milestones along a marathon route. In some embodiments, electronic device 400 may be integrated to prompt individual 100 on a particular route, with visual or audio cues along the route.

As another example, for a mindfulness domain discovery, system 10 may include a discovery related to how breath can affect what emotions are felt and how intensely those emotions are felt. For example, the system 10 may include a session related to exercises that orient a user to the fundamentals of breath rhythm and texture, including inhalation and exhalation. For example, the system 10 may include a session related to providing mental visualizations that help control breathing. For example, the system 10 may include a session related to teaching how pauses in breathing cycles can affect breathing patterns. For example, the system 10 may include a session related to how nostril breathing can affect breathing patterns. For example, the system 10 may be linked to sensors, such as brain wave sensors or biometric equipment, or make use of electronic device 400.

As another example, for a mindfulness domain discovery, system 10 may include a discovery related to how reducing background noise can improve routine activities or fitness activities. For example, the system 10 may include a session related to turning off the radio or music for, e.g., 10 minutes of a normal daily activity, such as a commute, and eventually increasing the time to 20 minutes. For example, the system 10 may include a session related to turning of the radio or music for 10 minutes at a time during an exercise or work out. For example, the system 10 may include a session related to muting commercials during a television program. In some embodiments, electronic device 400 may automatically alter the noise or audio properties for a given system, e.g., a radio or television or computing device.

As another example, for a mindfulness domain discovery, system 10 may include a discovery related to the effect of gestures of acceptance, appreciation, and affection on self-image, self-regard, and overall health and fitness. For example, the system 10 may include a session related to how giving or getting a hug can relax muscles, increase self-esteem, release hormones that improve feelings, and rebalance the nervous system. For example, the system 10 may include a session related to hugging family members, close friends, children, and siblings at least 5 times per day. For example, the system 10 may include a session related to showing affection to a pet 2 times per day, for 5 to 10 minutes each time. For example, the system 10 may include a session related to how simple physical contact with people outside of a user's normal emotional life can affect relationships. In some embodiments, system 10 may be linked to sensors, such as brain wave sensors, respiratory sensors, cardiac sensors, or biometric equipment, or make use of electronic device 400 to provide particular tips or insights within the discovery.

As another example, for a mindfulness domain discovery, system 10 may include a discovery related to how circadian rhythms can affect mental and physical abilities. For example, the system 10 may include a session related to sexual activity at a time when hormone levels are high, such as mid-morning or late night. System 10 may include a session related to performing activities that require significant mental focus at a time when mental performance is at a peak, such as late morning. In some embodiments, system 10 may include a session related to performing physical activities at a time when physical performance is at a peak, such as mid- to late-afternoon. For example, the system 10 may include a session related to eliminating activities that require high levels of attention and reaction at a time when the body is normally asleep, such as early morning hours. In some embodiments, electronic device 400 may track a circadian rhythm of individual 100.

As another example, for a nutrition domain discovery, system 10 may include a discovery related to exploring healthy recipes by virtually visiting cities around the world and creating a meal from each city. For example, the system 10 may include a session related to providing a recipes that include local ingredients and cooking tips to prepare meals that help restore and enhance gastrointestinal health and wellbeing. For example, the system 10 may include a session related to recipes from London, England; Marrakesh, Morocco; Perth, Australia; New Delhi, India; and Beijing, China. For example, the system 10 may include partnerships with cooking classes. In some embodiments, electronic device 400 may utilize location based features to provide tips at particular locations, e.g., notifying individual 100 that a particular vendor is close by and that offers food item or beverage related to the discovery.

As another example, for a nutrition domain discovery, system 10 may include a discovery related to how to shop for and prepare food to improve nutrition and avoid unhealthy food. For example, the system 10 may include a session related to providing a scavenger hunt at the grocery store to search for specific, healthy food options. For example, the system 10 may include a session related to superfoods, including providing new recipe ideas and infusing superfoods into popular or common recipes. In some embodiments, electronic device 400 may utilize location based features to provide tips at particular locations, e.g., notifying individual 100 that a particular vendor is close by and that offers food item or beverage related to the discovery.

As another example, for a rest domain discovery, system 10 may include a discovery related to how sound therapy can improve sleep habits and ensure a good night's sleep. For example, the system 10 may include a session related to providing a lullaby with multiple audio tracks that help ease a user into sleep. In some embodiments, system 10 may be linked to sensors, such as brain wave sensors, respiratory sensors, cardiac sensors, or biometric equipment, or make use of electronic device 400 to provide particular tips or insights within the discovery.

As another example, for a rest domain discovery, system 10 may include a discovery related to how and why the body reacts to different kinds of light and how modifying use of screens before bed helps improve sleep habits. For example, the system 10 may include a session related to orienting a user to different light temperatures and exploring how different light temperatures send different signals to the body. For example, the system 10 may include a session related to providing alternative activities to help prepare for bed, including pre-sleep routines such as books, magazines, audio tracks, etc. For example, the system 10 may include a session related to turning off the television 30 minutes before bed. For example, the system 10 may include a session related to turning off phones or tablets 10 minutes before bed and slowly increase that time to, for example, 20 minutes, 30 minutes, or 45 minutes.

As another example, for a rest domain discovery, system 10 may include a discovery related to how going to bed and waking up at consistent times promotes a natural sleep and wake rhythm. For example, the system 10 may include a session related to how a natural wake up in the morning is easier on the body and has a positive effect on the rest of the day. For example, the system 10 may include a session related to setting the alarm clock for 10 minutes earlier than normal and going to bed at a consistent time each night. For example, the system 10 may include a session related to setting the alarm forward 10 minutes but waking up before the alarm goes off. For example, the system 10 may include a session related to waking up without setting an alarm. In some embodiments, system 10 may automatically control an alarm set by electronic device 400, for example.

Figure 16B:
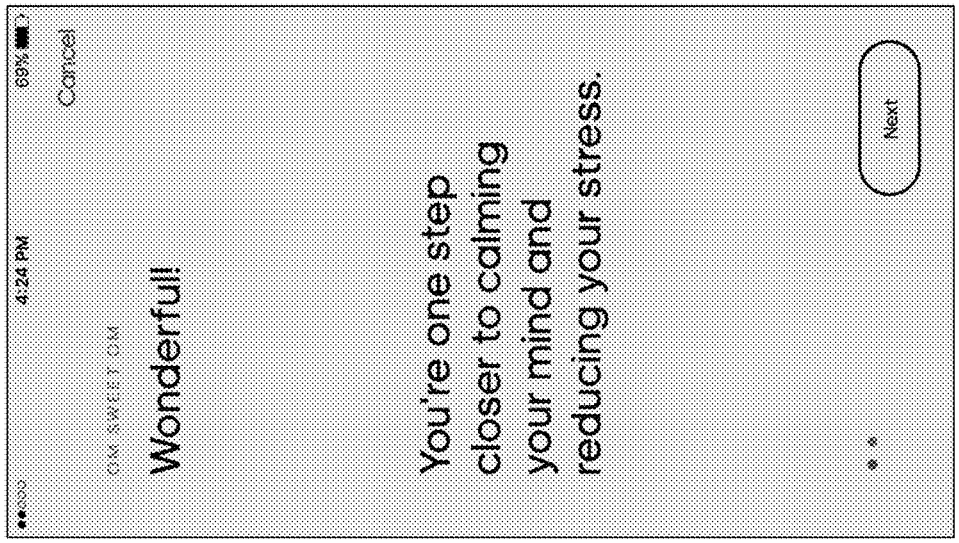
FIGS. 16A-17 show various graphical user interfaces for a system according to an embodiment.
Figure 16A:
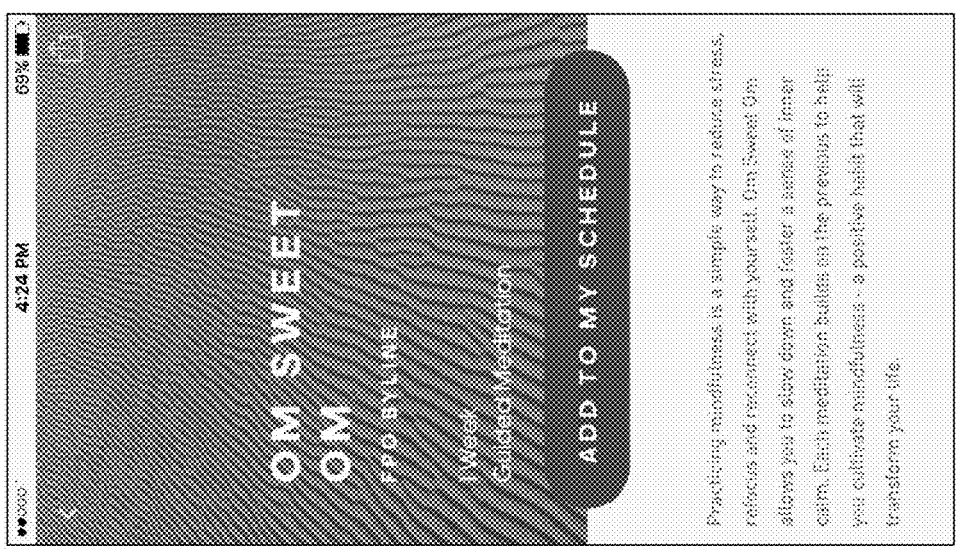
Figure 16D:
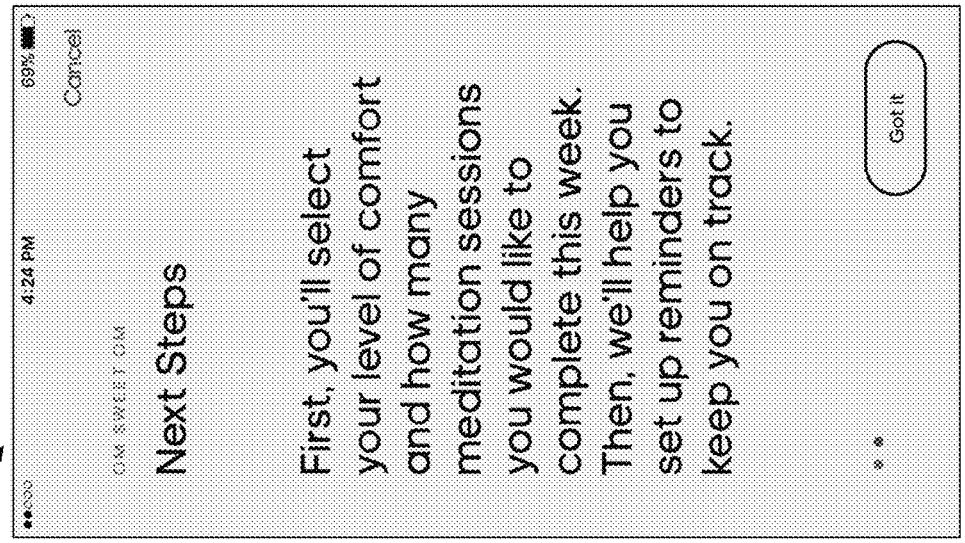
Figure 16C:
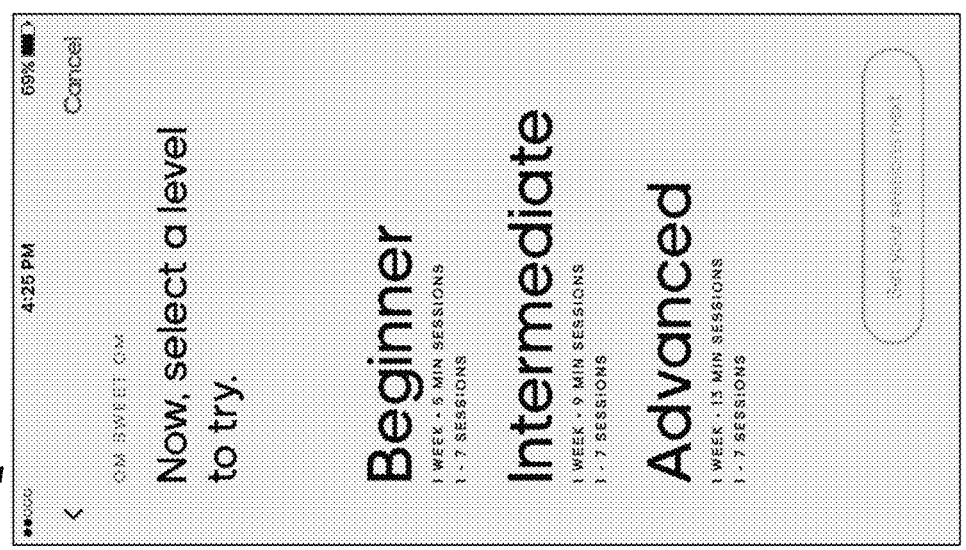
Figure 16F:
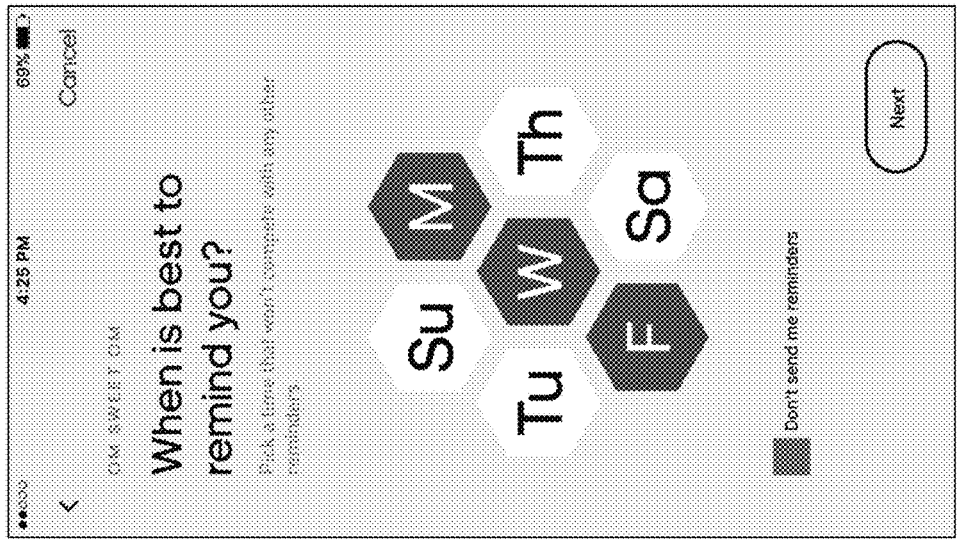
Figure 16E:
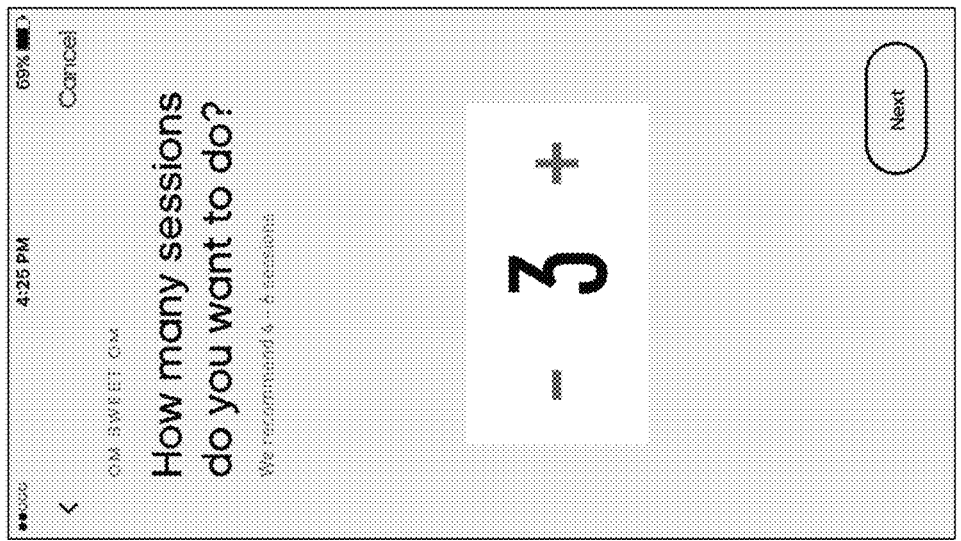
Figure 16H:
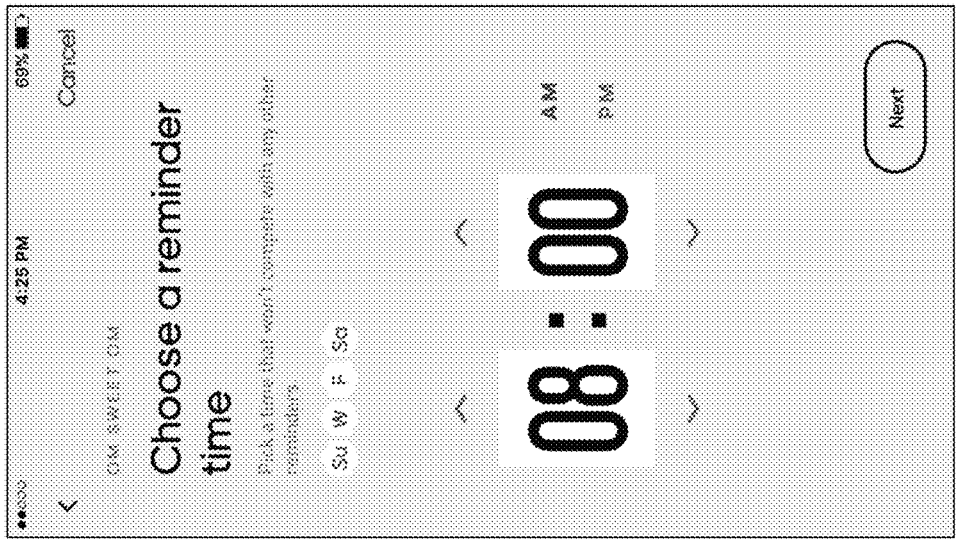
Figure 16G:
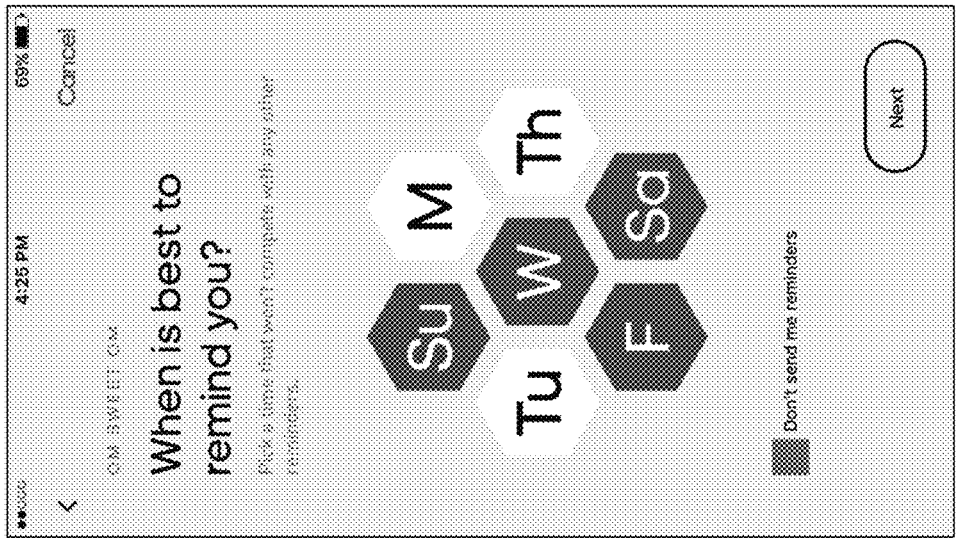
Figure 17:
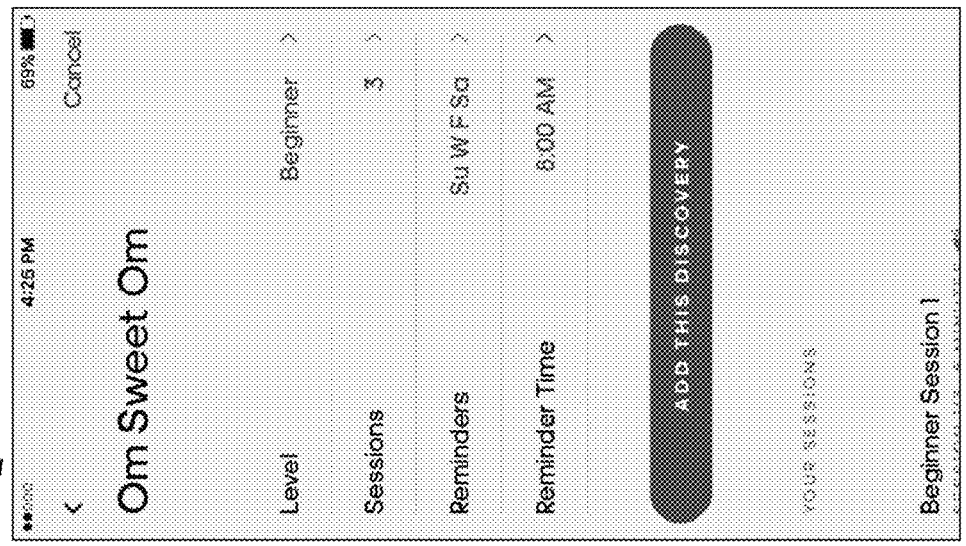

As shown in FIGS. 16A-17, system 10 may include representative GUI windows of a discovery add module 1120. As shown in FIG. 14A, discovery module or discovery add module may display icons or images related to a particular discovery. For example, a discovery related to nutrition may display a message related to healthy eating, or a picture of a healthy meal. Once an individual 100 selects to enroll in a discovery, discovery add module may include sub-modules to tailor the discovery to the specific needs of individual 100.

Software platform 1000 may additionally include social module 1122. In some embodiments, a social element may aid in behavioral change, and thus including social module 1122 is advantageous. In some instances, limiting the number of individuals in the social sharing circle may increase likelihood of behavioral change. For example, if a small group of real people are connected to motivate behavior change, this may be more successful than sharing on large social media platform. Social module 1122 may integrate several social media platforms, for example, or be a private social module standing alone. In some embodiments, social module 1122 may include a feed (e.g., from celebrities or social media influencers, friends, brands, companies, filtered content, etc.). In some embodiments, social module 1122 may include a messaging platform, or the ability for an individual to comment on various feed elements. In some embodiments, as described below, social features may be integrated within a discovery. In some embodiments, social module 1122 may enable an individual 100 to create a "buddy system" to keep the individual on track with their goals and engaged in their progress or activities, such as discoveries, for example. In some embodiments, social module 1122 may enable the individual 100 to create a story around their goals to gain support and celebrate progress, for example.

In some embodiments, social module 1122 may communicate with a retail module, e.g., an online store, or physical store. In some embodiments, social module 1122 may aggregate an individual's behavior through social module 1122, for example to suggest particular clothing, equipment, athletic apparel, footwear, etc., based on social module 1122 actions individual 100 may take. In some embodiments, social module 1122 may curate an intra-network messaging feature, and apply behavior rules to increase individual adoption, reach, and retention, for example. In some embodiments, social module 1122 may utilize suggestions of other individuals, (e.g., in the form of clustered lattice-networks) and apply behavior rules to increase individual adoption, reach, and retention, for example.

In some embodiments, social module 1122 may include, for example, a following/follower mechanism such that individuals may follow each other's progress. In some embodiments, social module 1122 includes a suggestion of relevant people to follow. In some embodiments, social module 1122 may include inspiration or recommendations from "others like you," as determined by system 10, for example. In some embodiments, social module 1122 includes a feed from people you are following and other content sources, and may include information such as participation numbers in each discovery available. In some embodiments, social module 1122 may utilize virtual or augmented reality features, for example to participate in a discovery with other individuals in remote locations. In some embodiments, social module 1122 may include a live video feature, such that influencers or individuals may show a live video feed of an activity, e.g., tied to a discovery.

In some embodiments, social module 1122 may include an invitation to join system 10, such as a text message or email communication. In some embodiments, individuals may request to follow other users, or accept following request (e.g., if individual has a private account in system 10, for example). In some embodiments, individuals may "follow back" an individual. In some embodiments, individual's may view other's public profiles. In some embodiments, social module 1122 may include a feature to find users using system 10 (e.g., from contacts, other social platforms, etc.), search for users using system 10 (e.g., through email/name/handle or nickname, etc.), suggest users using system 10 that an individual may enjoy following, or find inspiring (e.g., active users, influencers, common location/interests/goals, etc.).

In some embodiments, social module 1122 may include a feature to recommend a discovery to an individual using system 10, or an individual not using system 10 currently.

In some embodiments, social module 1122 may include a feature to share activities, e.g., workouts, photo or video related to a shared activity, mood while participating in the activity, information related to who else participated in the activity with the individual, tips or insights related to the activity, personal or physiological data, e.g., heart rate or pace, time based activity (e.g., daily, weekly, or monthly summary or detailed information), goals or milestones achieved, started a discovery, completed day X or session x of a discovery, or suggest a discovery to another user (e.g., private to another user, not in the feed), for example. In some embodiments, social module 1122 may include a template for posting or sharing information, e.g., categorized by domain or type of activity, that an individual may populate prior to posting. In some embodiments, social module 1122 may aggregate content, e.g., blog posts, events, or influencer content. In some embodiments, social module 1122 may include information as to sources for the feed, e.g., the individual's feed, feed of people the individual follows, a public feed, curated content, etc. In some embodiments, the feed may be filtered or aggregated, e.g., self-learning. In some embodiments, the feed may be adjusted based on factors such as different user behaviors, location, culture, aging, etc.).

In some embodiments, social module 1122 may integrate with a discovery library, for example displaying an aggregate of an individual's collective or tribe, or others with similar goals, others participating in similar activities, the entire system 10, anyone participating in a specific discovery, etc. In some embodiments, social module 1122 may enable an individual to "tag" a discovery in a message or comment, such that an individual selecting the tag may be able to participate in the discovery.

In some embodiments, social module 1122 may include measuring social activity and engagement, and may create and display a social graph, for example showing connections and interactions. In some embodiments, social module 1122 may include trending topics/activities/discoveries, etc., from an individual's collective or tribe. In some embodiments, social module 1122, may include trending individuals. In some embodiments, social module 1122 may determine patterns, such as engagement patterns, user growth patterns, sharing behavior, device type or ownership as compared to usage, etc. In some embodiments, some features of social module 1122 may be accessible only to a content partner, or brand that provides system 10, or access to system 10.

In some embodiments, social module 1122 includes smaller groups of individuals engaged in social features. In this regard, social module 1122 may include a smaller private group to enable doing a discovery together, such that it may facilitate conversation and cheering on through a private feed. In some embodiments, social module 1122 may communicate with electronic device 400, which may be a dedicated electronic device. In some embodiments, social module 1122 may utilize electronic device 400 to provide alerts or information from system 10, for example, and not provide alerts from other sources.

In some embodiments, social module 1122 may be integrated with, or may communicate with, additional social platforms or social channels that may be standalone social platforms or social channels, or social platforms or social channels within other applications.

In some embodiments, social module 1122 may divide or group individuals 100 into one or more categories, such as the public using system 10, clusters created by system 10, an individual's "collective," and an individual's "tribe(s)". FIGS. 32-36 illustrate conceptual relationships useful in a social module according to an embodiment, and are described briefly below. In the figures, "Sarah" is representative of an individual 100 using system 10. As shown in the FIGS., the varied shaded areas represent different groups or division in an individual's social module 1122. In some embodiments, social module 1122 includes social media influencers. In some embodiments, influencers may algorithmically be given more prominence to have more visibility either through what information is shown in the Public Space or encouraging users to follow. In some embodiments, individuals that are not influencers, but that have public profiles may also contribute to the public feed.

In some embodiments, social module 1122 may include clusters created by system 10. In some embodiments, clusters are groups created by system 10 and not visible to the individual. These clusters can be used as a way to identify items that show up in an individual's public view of the feed, recommendations for discoveries, and recommendations for people the individual may find interesting to follow, for example. In some embodiments, clusters may be matched based on information such as age, gender, location, common collectives, common activities, common discoveries, or common behavior within system 10 (e.g., liking various things, reading types of articles, etc.), for example.

In some embodiments, social module 1122 may include collective groups or divisions. In some embodiments, an individual's collective is the network of connections a user has curated. These could be friends a user has in the real world, total strangers or influencers. In some embodiments, individual 100 may choose to follow individuals to provide inspiration and support for example.

In some embodiments, social module 1122 may include tribe groups or divisions. In some embodiments, an individual's tribe may be organized around a discovery. In some embodiments, an individual may create multiple tribes. In some embodiments, system 10 may create tribes. In some embodiments, tribes are user created groups. In some embodiments, tribes may be created outside of particular discoveries, e.g., as part of a group workout, group activities and events, scheduling, reminders, etc.

In some embodiments, social module 1122 may be integrated with location based features, e.g., recognizing a location and associated activity and notifying an individual's collective or tribe what activity individual 100 may be engaged in. In some embodiments, social module 1122 may include real-time feedback to individual 1122 from her tribe or collective, for example. In some embodiments, feedback from an individual's 100 tribe, collective, etc., may be textual, audio, video, or haptic, for example, and may be delivered through electronic device 400 for example. In some embodiments, individual 100 may manually select which individuals, tribes, collective members, influencers, public, etc., to receive notifications or updates from. In some embodiments, individual 100 may manually select the type of feedback, category of feedback or notifications, or mode of notification such as visual, audio, haptic, etc. In some embodiments, communication through social module 1122 may include features only accessible to individuals 100 that have a particular type of electronic device 400, for example, a dedicated electronic device. In some embodiments, tips or insights may include content from an individual's tribe or collective. For example, if a member of an individual's tribe had good results with a particular discovery, an insight may be provided to the individual that the particular member had good result with a particular discovery and suggest that the individual participate in the discovery themselves. In some embodiments, the insight may be annonymized, such that the individual that first participated in the discovery remains anonymous.

As shown, for example, for a discovery involving guided meditation (designed to improve individual's mindset, for example), sub-module may include information related to the discovery, as shown in FIGS. 16A-16C. Content related to what the individual 100 will experience through the discovery may be displayed, or information related to benefits of a particular discovery. In some embodiments, as shown in FIG. 16D, individual will specify a level of discovery to enroll in, e.g., beginner, intermediate, advanced. In some embodiments, individual 100 may be queried as to a baseline level of a particular goal or domain, such as current level of stress, desired level of stress, current athletic activity, current eating habits, etc. In some embodiments, individual 100 may be queried regarding their TTM state in order to determine a readiness to change. These queries may affect the discovery. Other theories and/or models may be utilized, as referenced herein. As shown in FIG. 16E, in some embodiments, individual 100 may select a number of sessions of activity to participate in. As shown in 16F and 16G, in some embodiments, system 10 may recommend a range of values for levels or number of sessions. As shown in FIG. 16H, in some embodiments, individual may select times or locations to remind the individual 100 about discoveries they are enrolled in, or opt out of system 10 sending reminders. As shown in FIG. 17, in some embodiments, a discovery summary sub-module may be displayed, such that it reflects a summary of individual's selections related to the discovery. In some embodiments, discoveries may account for activity, location, and the like. For example, if individual 100 completes a particular activity at a particular location, a discovery may provide additional information related to that activity in the form of an insight or tip. As another example, if an individual 100 is enrolled in a healthy eating discovery, a discovery may automatically show individual 100 healthy options at restaurants near the individual's place of work. In some embodiments, individual 100 may share their discoveries, discovery sessions, tips, insights, etc. through social module 1122.

Additional discoveries may include activities such as breathing exercises, taking a daily walk, running instruction or exercises, nutritional encouragement such as eating a healthy breakfast, sleep sounds exercises, reminders to turn the lights out to go to bed at a particular time, additional athletic challenges, etc.

In some embodiments, discovery add module may display discoveries individual 100 is currently enrolled in. In some embodiments, the module may display available discoveries, featured discoveries, trending discoveries, or recommended discoveries based on insights related to individual 100. In some embodiments, discoveries may be organized by goal categories, or known goals of individual 100. In some embodiments, individual 100 may be able to manually mark a discovery session complete, end a discovery prior to completion, or share a discovery. In some embodiments, discoveries may include content downloads, such as images or videos, related to the experience. In some embodiments, content related to the discovery may be streamed from a network. In some embodiments, system 10 may query individual 100 as to categories of current state, desired state, readiness to change, etc. In this regard, system 10 may tailor discoveries suggested to narrow suggestions to attainable discoveries appropriate to self-assessed readiness, for example as it relates to individuals TTM state. In some embodiments, self-assessments may be repeated throughout a discovery session or discovery. In some embodiments, the discovery will include a query as to how individual is feeling after a discovery session, after a predetermined time, after a predetermined number of discovery sessions, etc. In this regard, the baseline may be compared against the progress individual 100 is making through the discovery or towards a goal. In some embodiments, if the queries indicate less than a target level of progress, the individual may be queried whether to start over, modify the discovery, leave discovery, contact a coach, etc.

In some embodiments there may be an educational section within one or more modules, including within discoveries or discovery sessions. In some embodiments this may include information general to health and fitness, or more specialized information, such as information about running or a particular athletic activity, or nutrition, mindset, or rest. In some embodiments, additional measurement visualizations may be included, that may display certain graphical information regarding the discovery. In one embodiment, this graphical information may include scientific information regarding the discovery. In some embodiments, modules and sub-modules may be available to the individual in real-time during completion of the discovery, or discovery session. In some embodiments, discoveries may link to other sources, e.g., to content partners such as celebrities, athletes, online retail stores, etc. In some embodiments, discoveries may link to suggested products, such as athletic wear or equipment, for example. In some embodiments, the system 10 may send an analysis results to the individual 100 or other interested party. In some embodiments, system 10 may include marketing or promotional material, such as special coupons to purchase online (e.g. 10% discount, free expedited shipping, or the like).

Figure 18:
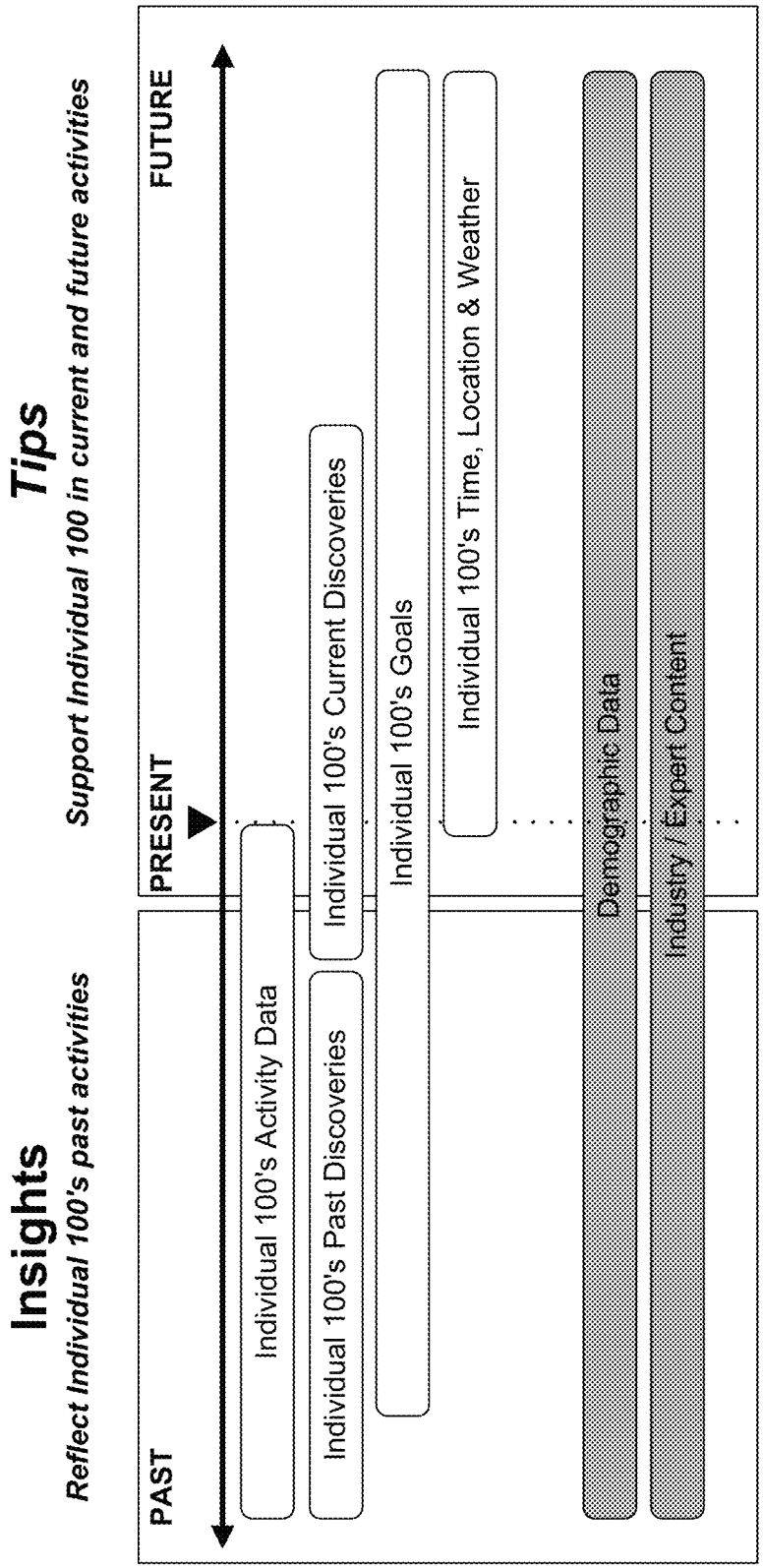
FIG. 18 shows a conceptual illustration of characteristics of tip sand insights, respectively, according to various embodiments.
Figure 19A:
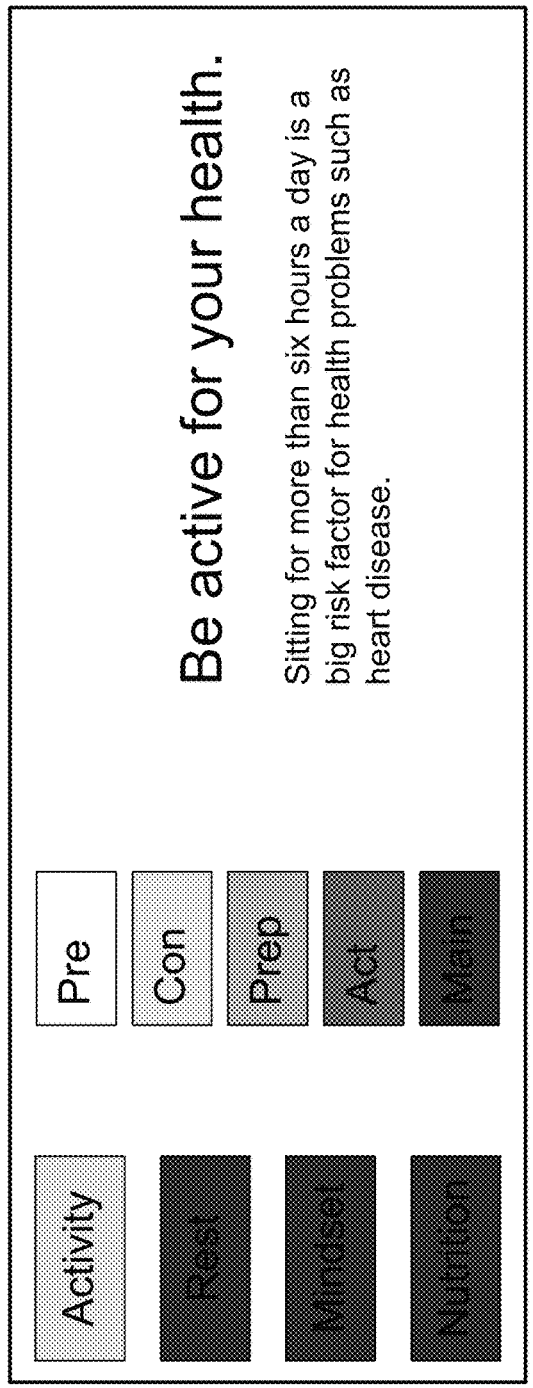
FIGS. 19A-22B show conceptual mapping of tips or insights mapped generally to domains and transtheoretical model states according to various embodiments.
Figure 19B:
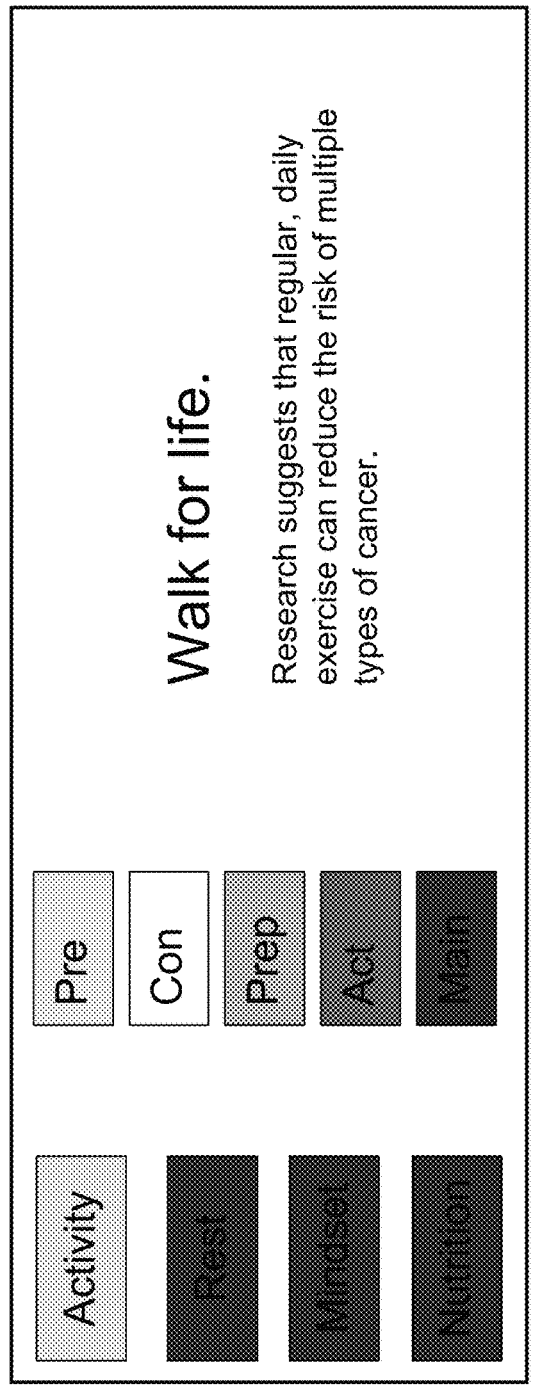
Figure 19C:
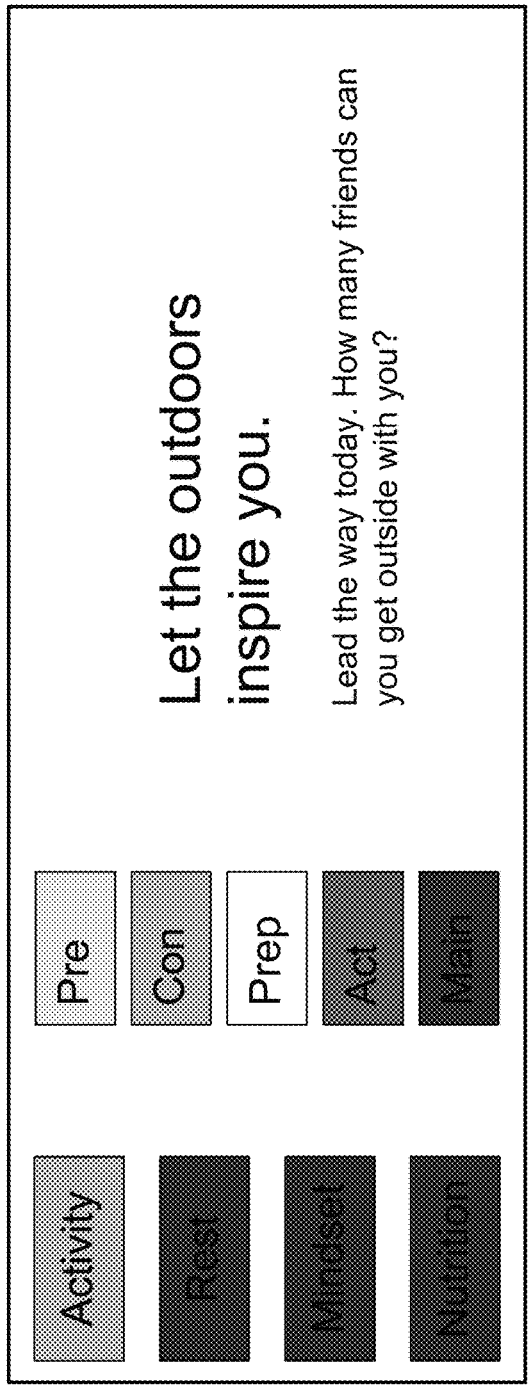
Figure 19D:
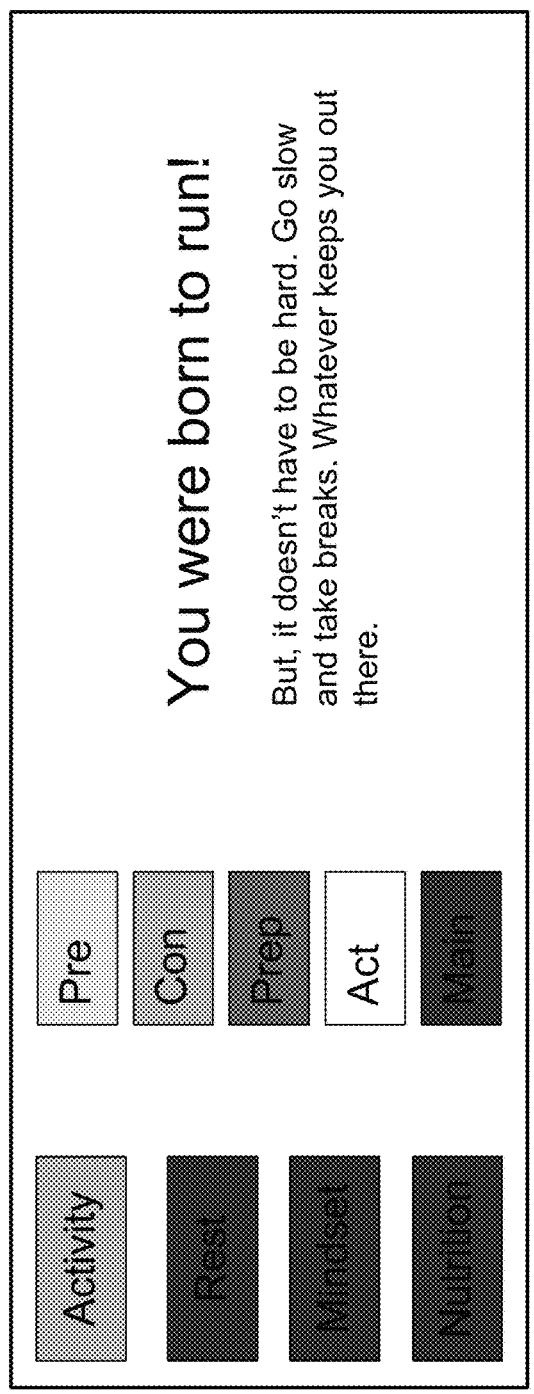
Figure 19E:
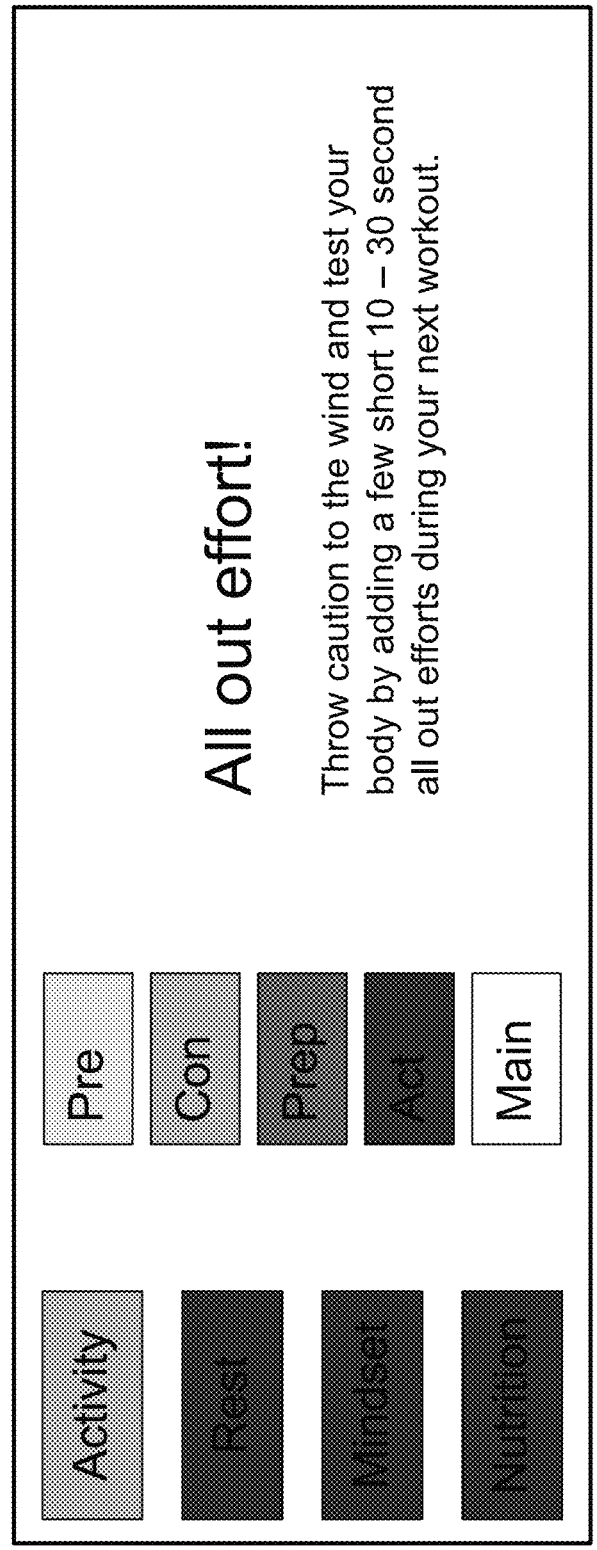
Figure 20A:
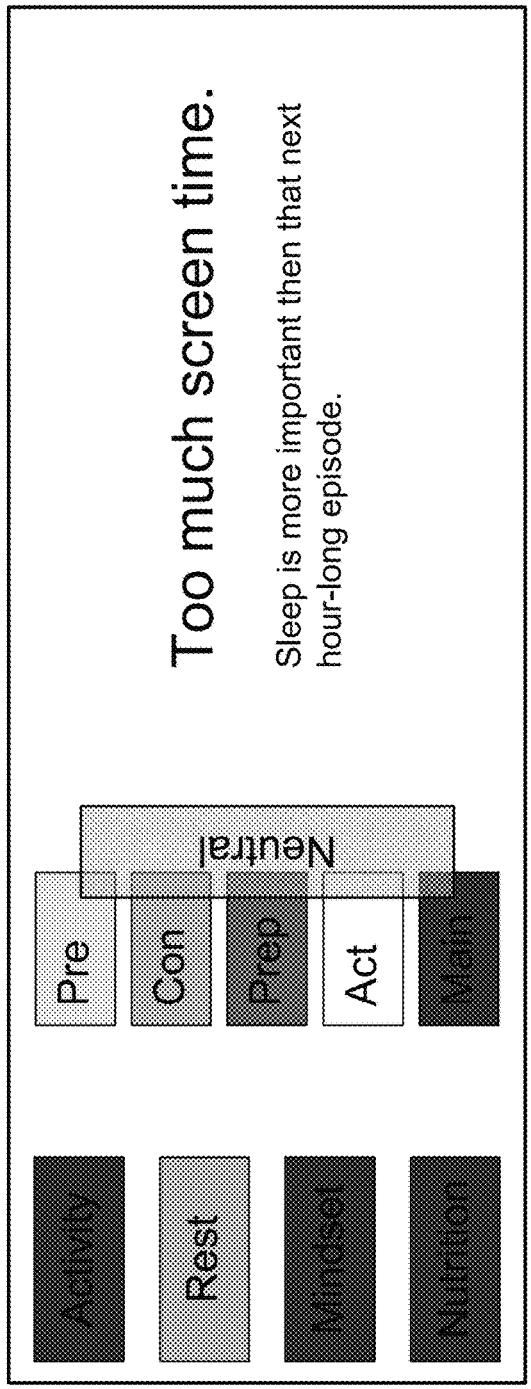
Figure 20B:
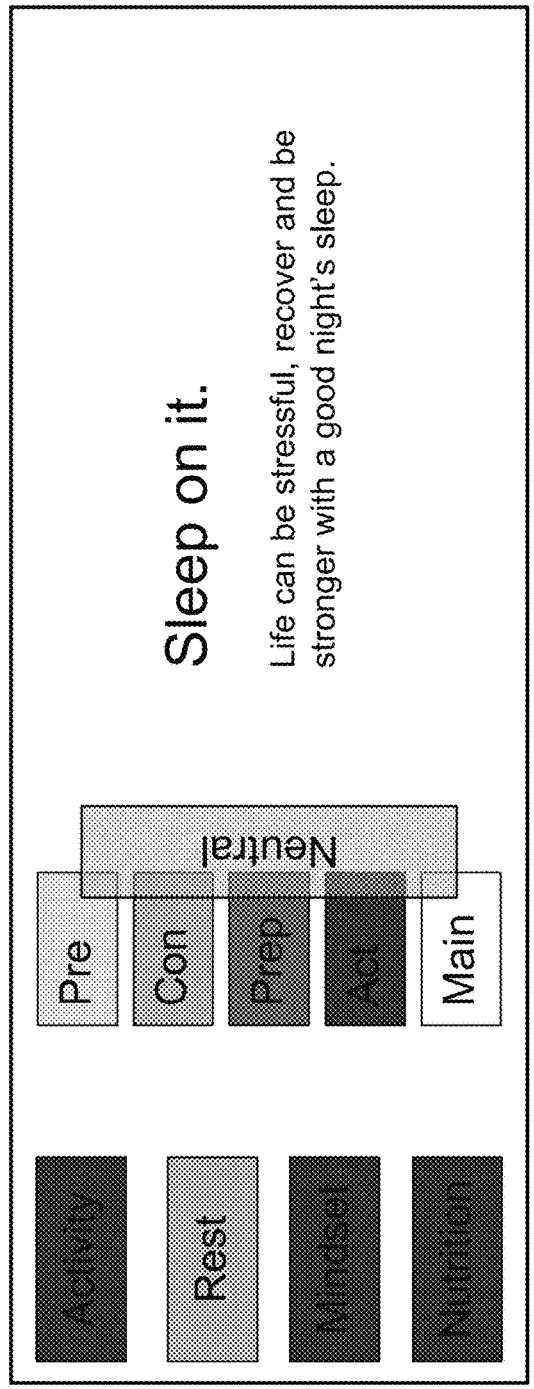
Figure 21A:
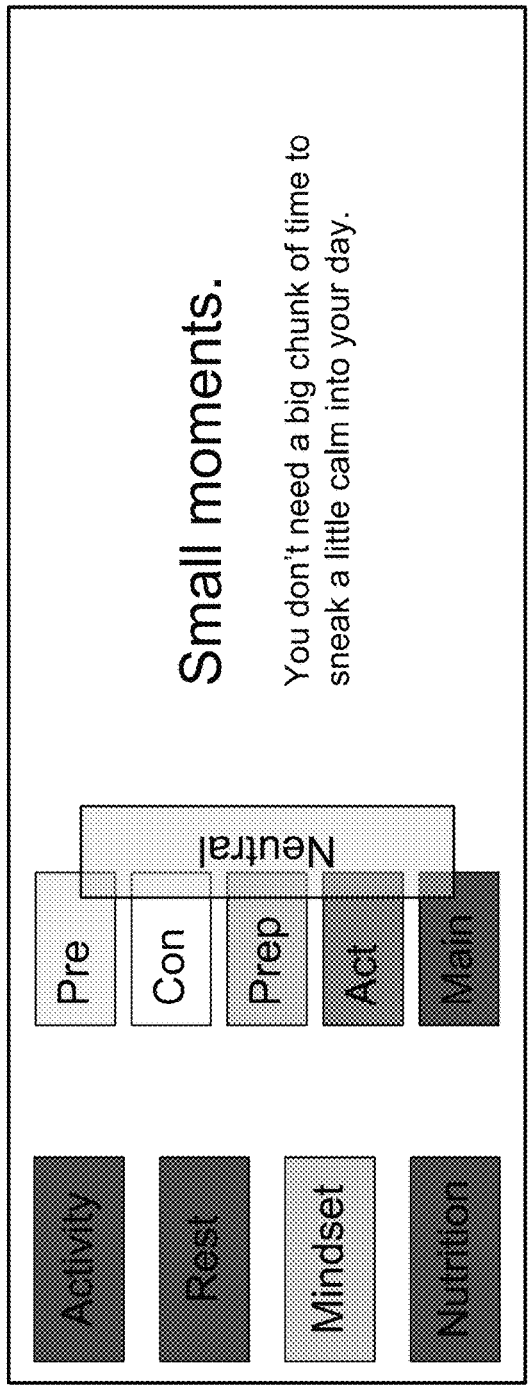
Figure 21B:
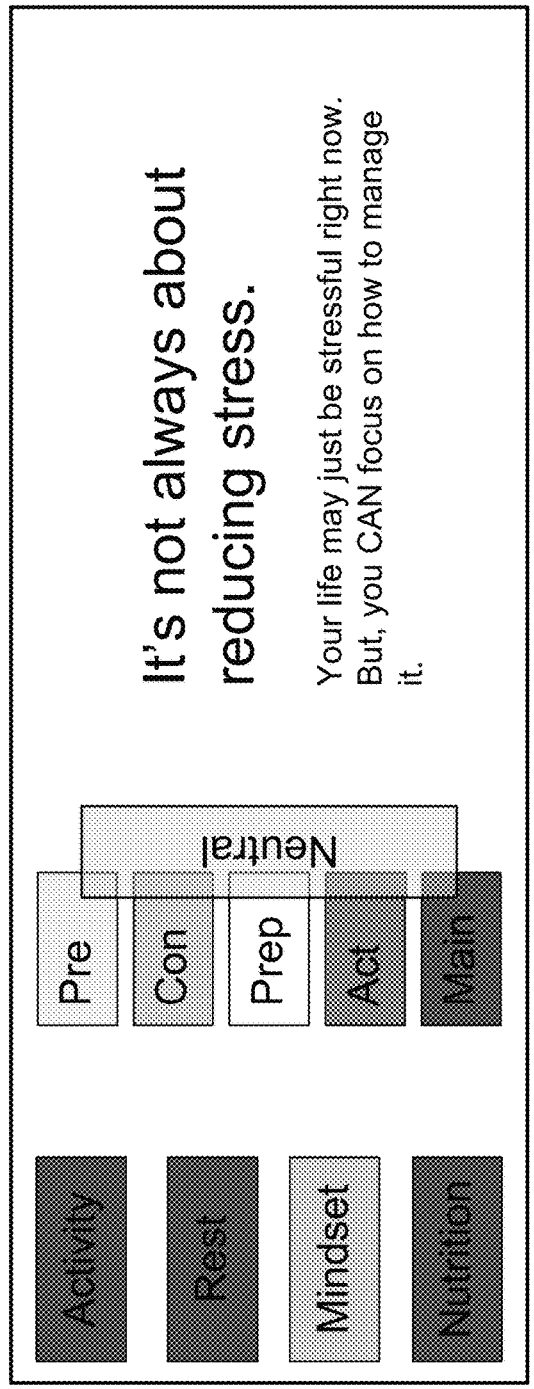
Figure 22A:
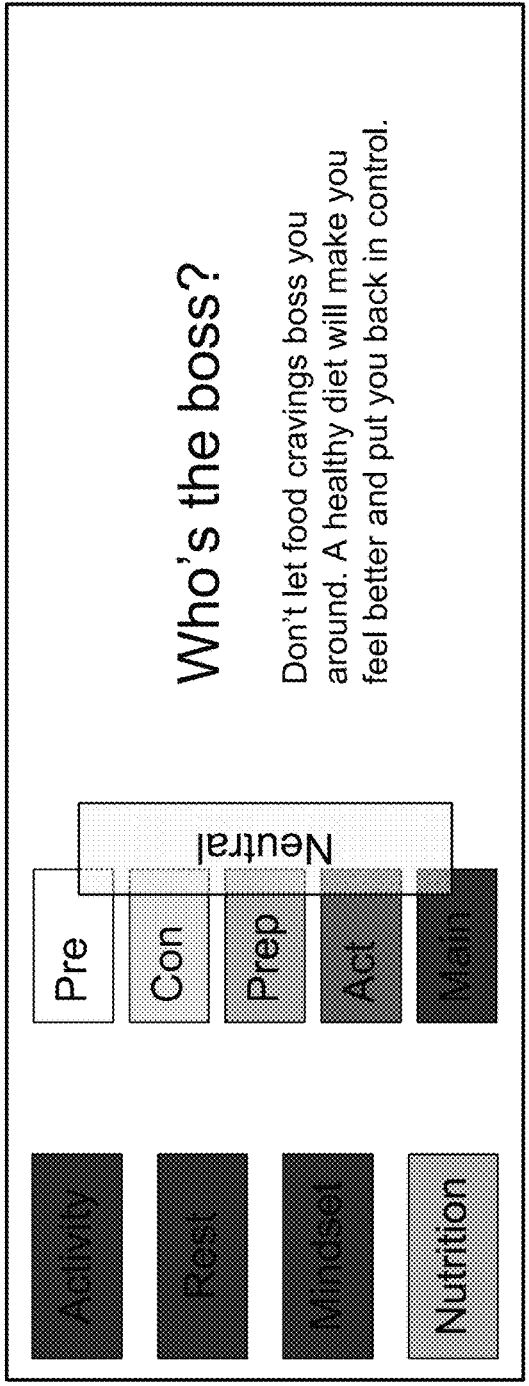
Figure 22B:
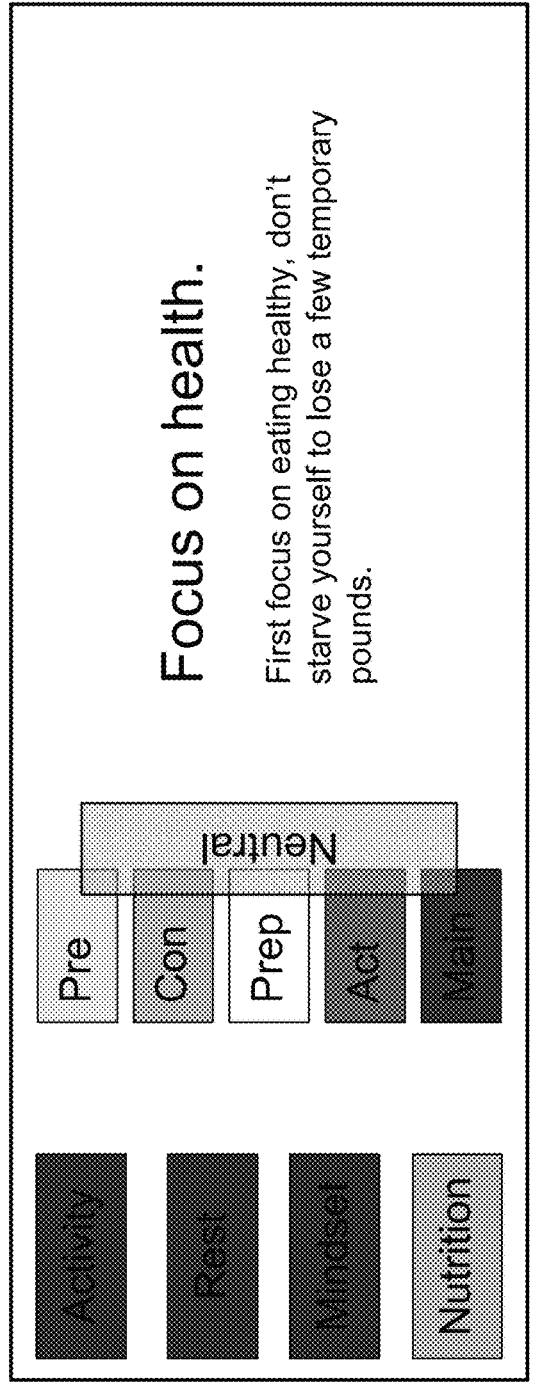

Advantageously, discoveries may feed data and information into system 10, such that additional tips and insights may be presented to individual 100. As used herein, system 10 may provide both "tips" and "insights." As illustrated in FIG. 18, tips may be content or messages that support a user in current and future activities, while insights may be content or messages that include and reflect an individual's past activities. In some embodiments, system 10 is configured to display tips on a particular schedule. In some embodiments, tips may be randomly displayed. In some embodiments, tips may be selected based on an individual's selection, such as a type of goal, discovery experience, or the like. In some embodiments, tips may be configured to correspond to a likely TTM state. In some embodiments, tips may help individual 100 gain more information regarding a certain goal. In some embodiments, tips may reinforce information individual 100 may already know. In some embodiments, tips are triggered based on how individual 100 uses system 10, e.g., frequency, types of goals, etc. In some embodiments, tips may be given outside of the application or system 10, e.g., a notification on an electronic device operating system, e.g., a mobile electronic device operating system. Examples of tips correlated with TTM states may be found on FIGS. 19A-22B. Figures that show a neutral bar along the TTM state indicate that the message or content is designed to be neutral with respect to the TTM state an individual may be in. For example, a tip related to activity to be given to an individual 100 in TTM pre-contemplation state may be "Be active for your health." In some embodiments, additional detail may be included, for example such as "Sitting for more than six hours a day is a bit risk factor for health problems such as heart disease." In some embodiments, the tone of content or message may be altered related to the TTM state. For example, the tip "Be active for your health," may be re-written as "Walk for life. Research suggests that regular, daily exercise can reduce the risk of multiple types of cancer." Such a message may be delivered to the same individual 100 related an activity goal if they are in a contemplative TTM state.

System 10 may also provide insights. As above, insights may be similar to tips, but insights may be content or messages that include and reflect an individual's past activities. In some embodiments, insights may highlight and reflect details about an individual's past data, such as a progress through a goal, or participation in a discovery experience. In some embodiments, insights may be displayed only when system 10 detects information that is relevant to individual 100. In some embodiments, insights may include a tip. In some embodiments, insights may be displayed in a separate module, and may be saved, similar to tip module 1114. Insights are further described in the context of discovery experiences elsewhere in this disclosure.

In some embodiments, system 10 may utilize several types of insights, such as core insights, discovery insights, goal insights, and the like. In some embodiments, core insights may include insights related to an individual's 100 current habits and activities. For example, core insights may analyze trends and relationships in activities participated in by individual 100 (e.g., trends, streaks, lulls, averages, records, correlations, etc.) In some embodiments, discovery insights may be utilized to provide insight into the new activities or tools individual is trying due to the enrollment in one or more discoveries. Advantageously, discovery insights may illuminate the effect a particular discovery is having on an individual's progress towards their goal. This provides immediate feedback, celebrates short term effects, and educates individual 100 on long term benefits they may not see yet. In some embodiments, system 10 will solicit feedback from user on the effect of new activity that will help track progress or guide to a new discovery. In some embodiments, goal insights may be provided such that an insight is tied to a particular goal of individual 100. System 10 may provide insights in manners similar to tips as described above. In some embodiments, when individual 100 completes a particular discovery, system 10 may display a change in a behavior correlated to an original baseline obtained from individual 100. In some embodiments, system 10 may "check-in" periodically with individual 100 relative to their status in a maintenance TTM state related to the discovery. In some embodiments, this may include re-engagement, e.g., suggesting to individual 100 the same discovery again but with altered intensity or length of time, suggest different discovery sharing similar goal category, etc.

Insights may depend on one or more variables. For example, a core insight may include one variable, such as recognizing a trend in variable "x." Examples of core insights related to trends include "You've increased the pace of individual your runs over the last month;" "you're averaging 10 minutes per mile, up from 10:30!" "you're building your endurance!" and the like.

Some insights may determine an average in variable "x". Examples of such an insight as applied to a rest goal or discovery could be "you average about 30 min of deep sleep per night, lower than most women your age;" or "deep sleep is great for energy the next day, and the minerals found in your smoothie challenge may promote deeper sleep."

Some insights may determine a streak in variable "x". An example of such an insight is "you rode your bike every day this month. Great job staying consistently active!"

Some insights may determine a lull in variable "x". An example of such an insight is "You haven't gone on a run in 2 weeks. How are you feeling?"

Some insights may determine a record in a variable "x". An example of such an insight is "you've run more miles this week than any previous week. Keep it up!"

In some embodiments, insights may include compound categories, such as a trend, and an average, such as "we've noticed your runs are getting longer—you're averaging 2.5 miles recently. You're building up your endurance! Your body and mind will thank you." In some embodiments, additional text may be tailored depending on a TTM state the individual 100 is experiencing. In this way, the messaging can be tailored to increase likelihood of behavior change and maintenance. In some embodiments, insights may include information related to a goal. For example, if an individual 100 has selected stress reduction as a goal, the previous insight may be presented as "We've noticed your runs are getting longer—you're averaging 2.5 miles recently. You're building up your endurance! Plus, your increased physical activity may help to reduce stress."

In some embodiments, insights may include a tip, such as "You get an average of 2 h 15 m of REM sleep per night. That's more than most women your age, who average 1 h 45 m. REM sleep stimulates the brain regions associated with learning and creativity." The added information regarding REM sleep stimulating brain regions with learning and creativity is information related to the insight, and is a tip that may relate to a rest or mindset domain to inform an individual of additional information.

In some embodiments, insights may be expressly tied to a discovery, as a discovery insight. For example, if an individual 100 is enrolled in a discovery where she has a smoothie for breakfast each morning, an insight related to activity may be presented, such as "maybe it's the smoothies, or maybe it's just you being awesome, but you've upped your activity since the beginning of this discovery—your active minutes are up 12%. Way to go!" In some embodiments, discovery insights may additionally reference a goal of individual 100. For example, for the same individual enrolled in a discovery where she has a smoothie for breakfast each morning and has selected a goal of reducing stress, the same insight may add "An added bonus: those fresh fruits and veggies provide an array of vitamins and minerals that are great for reducing stress. Have you noticed a reduction in stress since you started?"

In some embodiments, insights may identify multi-variable correlations. An example of such an insight is "You tend to have longer periods of deep sleep the night after you go on a run;" or "you tend to be less active during the day when you get more than 9 hours of sleep." In this regard, system 10 may aid individual 100 in identifying correlations between various behaviors, goals, domains, insights, discoveries, etc.

As described above, additional examples of tips, which may be included in insights, shown paired with TTM states and domains of activity, rest, mindset, and nutrition are shown in FIGS. 19A-22B.

Embodiments of the present invention may incorporate features of motion and performance monitoring systems. Exemplary motion monitoring and performance systems are disclosed in commonly owned U.S. patent application Ser. No. 13/077,494, filed Mar. 31, 2011 (which published as U.S. Patent App. Pub. No. 2012/0254934), and commonly owned U.S. patent application Ser. No. 13/797,361, filed Mar. 12, 2013 (which published as U.S. Patent App. Pub. No. 2014/0266160), the entirety of each being incorporated herein by reference thereto.

An overview of exemplary embodiments of components of the system 10 of the present invention, including exemplary sensor modules 102, has been provided above.

Figure 23:
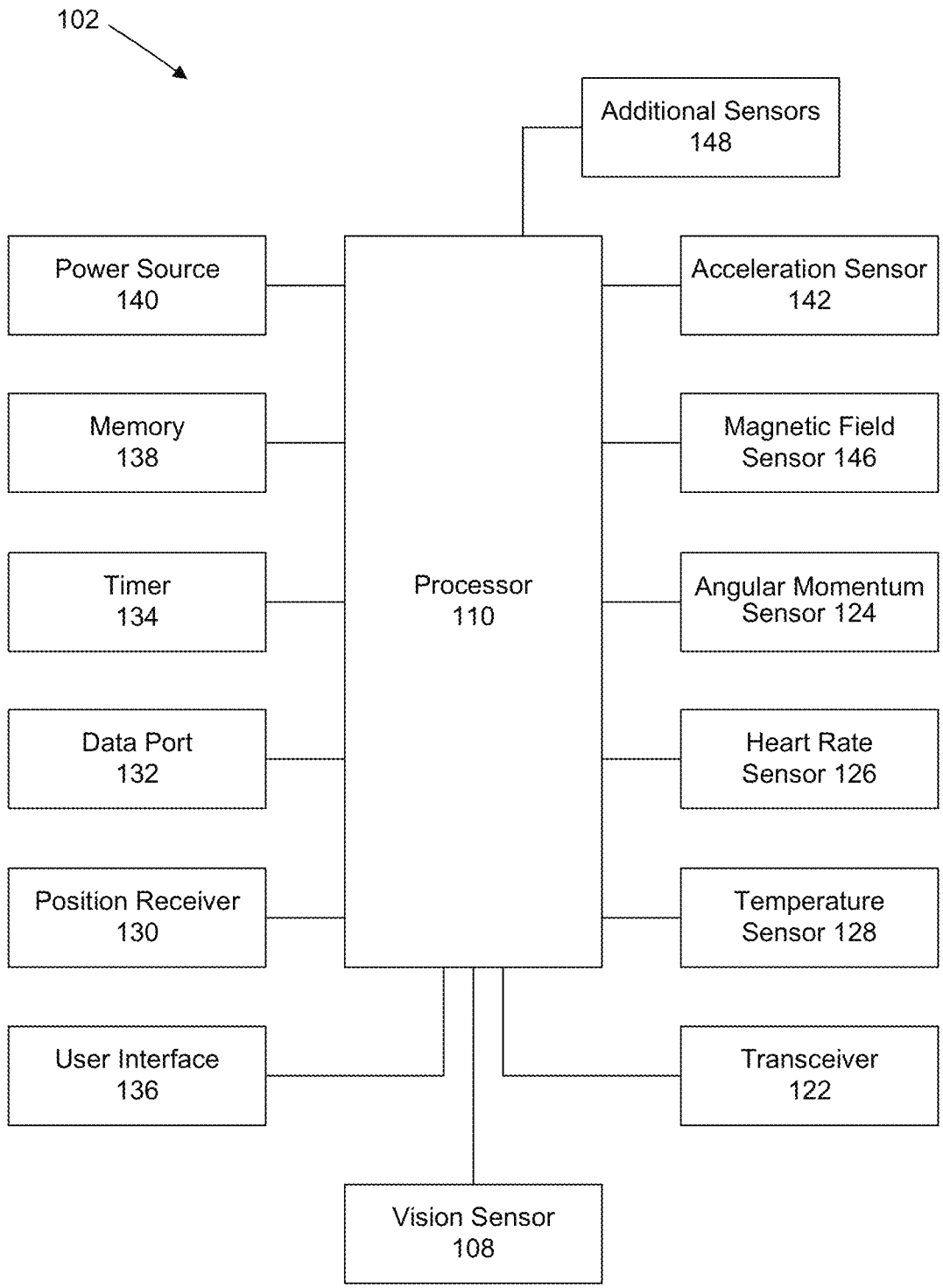
FIG. 23 is an example sensor module useful for implementing various embodiments.

Turning to FIG. 23, a block diagram of components of a sensor module 102 according to some embodiments of the present invention is shown. In the illustrated embodiment, the sensor module 102 may include processor 110 (processor 110 may also be a separate component). Sensor module 102 may include a power source 140, a memory 138, an acceleration sensor 142, a magnetic field sensor 146, and a transceiver 112 (transceiver 112 may be a separate component). These components are operatively connected to one another to carry out the functionality of the sensor module 102. In other embodiments, one or more of these sensor module 102 components may be omitted, or one or more additional components may be added. Processor 110 may be included in sensor module 102, or may be a separate component. Processor 110 may be adapted to implement application programs stored in the memory 138 of the sensor module 102. The processor 110 may also be capable of implementing analog or digital signal processing algorithms such as raw data reduction and filtering. For example, processor 110 may be configured to receive raw data from sensors and process such data at the sensor module 102. The processor 110 is operatively connected to the power source 140, the memory 138, the acceleration sensor 142, the magnetic field sensor 146, and the transceiver 112.

In an embodiment, calibration of sensor module 102 is performed using, for example, received GPS signals from a position receiver 130. The received GPS signals can be used, for example, to determine a distance that an individual runs or walks during a workout.

The power source 140 may be adapted to provide power to the sensor module 102. In one embodiment, the power source 140 may be a battery. The power source may be built into the sensor module 102 or removable from the sensor module 102, and may be rechargeable or non-rechargeable. In some embodiments, the power source 140 may be recharged by a cable attached to a charging source, such as a universal serial bus ("USB") FireWire, Ethernet, Thunderbolt, or headphone cable, attached to a personal computer. In another embodiment, the power source 140 may be recharged by inductive charging, wherein an electromagnetic field is used to transfer energy from an inductive charger to the power source 140 when the two are brought in close proximity, but need not be plugged into one another via a cable. In some embodiment, a docking station may be used to facilitate charging. In other embodiments, the sensor module 102 may be repowered by replacing one power source 140 with another power source 140.

The memory 138 may be adapted to store application program instructions and to store athletic activity data. In some embodiments, the memory 138 may store application programs used to implement aspects of the functionality of the system 10 described herein. In one embodiment, the memory 138 may store raw data, recorded data, and/or calculated data. In some embodiments, as explained in further detail below, the memory 138 may act as a data storage buffer. The memory 138 may include both read only memory and random access memory, and may further include memory cards or other removable storage devices.

In some embodiments of the present invention, the memory 138 may store raw data, recorded data, and/or calculated data permanently, while in other embodiments the memory 138 may only store all or some data temporarily, such as in a buffer. In one embodiment of the present invention, the memory 138, and/or a buffer related thereto, may store data in memory locations of predetermined size such that only a certain quantity of data may be saved for a particular application of the present invention.

The acceleration sensor 116 may be adapted to measure the acceleration of the sensor module 102. Accordingly, when the sensor module 102 is physically coupled to an object such as electronic device 400, for example, or individual 100, the acceleration sensor 116 may be capable of measuring the acceleration of the object, including the acceleration due to the earth's gravitational field. In one embodiment, the acceleration sensor 116 may include a tri-axial accelerometer that is capable of measuring acceleration in three orthogonal directions. In other embodiments one, two, three, or more separate accelerometers may be used.

The magnetic field sensor 146 may be adapted to measure the strength and direction of magnetic fields in the vicinity of the sensor module 102. Accordingly, sensor module 102, utilizing the magnetic field sensor 146, may be capable of measuring the strength and direction of magnetic fields in the vicinity of the individual 100, including the earth's magnetic field. In one embodiment, the magnetic field sensor 146 may be a vector magnetometer. In other embodiments, the magnetic field sensor 146 may be a tri-axial magnetometer that is capable of measuring the magnitude and direction of a resultant magnetic vector for the total local magnetic field in three dimensions. In other embodiments one, two, three, or more separate magnetometers may be used.

In one embodiment of the present invention, the acceleration sensor 116 and the magnetic field sensor 146 may be contained within a single accelerometer-magnetometer module bearing model number LSM303DLHC made by STMicroelectronics of Geneva, Switzerland. In other embodiments, the sensor module 102 may include only one of the acceleration sensor 116 and the magnetic field sensor 146, and may omit the other if desired.

The transceiver 122 depicted in FIG. 23 may enable the sensor module 102 to wirelessly communicate with other components of the system 10, such as those described in further detail below. In one embodiment, the sensor module 102 and the other local components of the system 10 may communicate over a personal area network or local area network using, for example, one or more of the following protocols: ANT, ANT+ by Dynastream Innovations, Bluetooth, Bluetooth Low Energy Technology, BlueRobin, or suitable wireless personal or local area network protocols. Other known communication protocols suitable for a system 10 may also be used. In one embodiment, the transceiver 122 is a low-power transceiver. In some embodiments, the transceiver 122 may be a two-way communication transceiver 122, while in other embodiments the transceiver 122 may be a one-way transmitter or a one-way receiver. Wireless communication between the sensor module 102 and other components of the system 10 is described in further detail below. In other embodiments, the sensor module 102 may be in wired communication with other components of the system 10 that does not rely on transceiver 122.

In some embodiments of the present invention, a sensor module 102 having components such as those depicted in FIG. 23 may be physically coupled to individual 100. Sensor module 102 may further monitor changes in the spatial orientation of the individual's 100 body or a piece of the individual's athletic equipment or article of footwear, or to determine a correlation between body or equipment movement data and a characteristic such as gait characteristic. In some embodiments, additional sensors not coupled to individual 100 (e.g., other acceleration sensors, physiological sensors, etc.) may be responsible for collecting the data necessary to carry out the various monitoring calculations.

In some other embodiments, however, it may be desirable to have additional sensors 148 (for example, such as speed sensors, etc.) included within the sensor module 102, or operatively connected to sensor module 102, or to have additional sensors in communication with the sensor module 102. In some embodiments, an additional sensor module 102 may be integrated within an existing piece of athletic activity monitoring equipment possibly having additional or different sensors such as, for example, a heart rate monitoring device, a pedometer, and accelerometer-based monitoring device, or other fitness monitoring device.

In one embodiment, sensor modules 102 according to the present invention are used to detect changes in an individual's direction of motion. Sensor modules 102 according to the present invention can also be worn by individuals and used to detect and/or track other motions such as, for example, motions associated with push-ups, pull-ups, weightlifting, diving, gymnastics, et cetera.

In addition to the acceleration sensor 116 and the magnetic field sensor 118, other sensors that may be part of the sensor module 102 or separate from but in communication with the sensor module 102 and may include sensors capable of measuring a variety of athletic performance parameters. The term "performance parameters" may include physical parameters and/or physiological parameters associated with the individual's 100 athletic activity. Physical parameters measured may include, but are not limited to, time, distance, speed, pace, pedal count, wheel rotation count, rotation generally, stride count, stride length, airtime, stride rate, altitude, strain, impact force, jump force, force generally, and jump height. Physiological parameters measured may include, but are not limited to, heart rate, respiration rate, blood oxygen level, blood lactate level, blood flow, hydration level, calories burned, or body temperature.

While various embodiments of the present invention are described in the context of the general health and wellness in terms of activity, nutrition, mindset, and rest, the present invention is not so limited and may be applied in a variety of different sports or athletic activities including, for example, running, sports of soccer (i.e., football), basketball baseball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto. In some embodiments, the system may make recommendations regarding articles of apparel or other sports equipment in addition to, or in substitution of articles of footwear.

As shown in FIG. 23, in some embodiments, sensor module 102 may incorporate other additional components. In some embodiments, sensor module 102 may incorporate an angular momentum sensor 124, a heart rate sensor 126, a temperature sensor 128, a position receiver 130, a data port 132, a timer 134, and a vision sensor 108 operatively connected to one another to carry out the functionality of the sensor module 102. In other embodiments, one or more of these sensor module 102 components may be omitted, or one or more additional components may be added.

In view of the above discussion, it is apparent that various processing steps or other calculations recited herein may be capable of being performed by various embodiments of the system 10 disclosed herein, and are not necessarily limited to being performed by the sensor module 102, depending on the configuration of a particular embodiment of the present invention. For example, any of the processing steps or other calculations recited herein may be performed, in various embodiments, by the sensor module 102, by a server computer 604, by an electronic device 400, and/or any other network component, or by more than one component.

Embodiments of the present invention may involve the use of so-called "cloud computing." Cloud computing may include the delivery of computing as a service rather than a product, whereby shared resources, software, and information are provided to computers and other devices as a utility over a network (typically the Internet). Cloud computing may entrust services (typically centralized) with an individual's 100 data, software and computation on a published application programming interface over a network. End users may access cloud-based applications through a web browser or a light weight desktop or mobile app while the business software and data are stored on servers at a remote location. Cloud application providers often strive to give the same or better service and performance than if the software programs were installed locally on end-user computers.

In some embodiments, the transceiver 122 may be a two-way communication transceiver 122, while in other embodiments the transceiver 122 may be a one-way transmitter or a one-way receiver.

The user interface 136 of the sensor module 102 may be used by the individual 100 to interact with the sensor module 102. In some embodiments, the user interface 136 may include one or more input buttons, switches, or keys, including virtual buttons, switches, or keys of a graphical user interface touch screen surface. The function of each of these buttons, switches, or keys may be determined based on an operating mode of the sensor module 102. In one embodiment, the user interface 136 may include a touch pad, scroll pad and/or touch screen. In another embodiment, the user interface 136 may include capacitance switches. In a further embodiment, the user interface 136 may include voice-activated controls.

In some embodiments, however, the sensor module 102 may not include a user interface 136. In these embodiments, the sensor module 102 may be capable of communicating with other components of the system 10 which may themselves include user interfaces, for example, electronic device 400.

The angular momentum sensor 124, which may be, for example, a gyroscope, may be adapted to measure the angular momentum or orientation of the sensor module 102. Accordingly, when the sensor module 102 is physically coupled to user 100, the angular momentum sensor 124 may be capable of measuring the angular momentum or orientation of the user. In one embodiment, the angular momentum sensor 124 may be a tri-axial gyroscope that is capable of measuring angular rotation about three orthogonal axes. In other embodiments one, two, three, or more separate gyroscopes may be used. In some embodiments, the angular momentum sensor 124 may be used to calibrate measurements made by one or more of the acceleration sensor 116 and the magnetic field sensor 146.

The heart rate sensor 126 may be adapted to measure an individual's 100 heart rate. The heart rate sensor 126 may be placed in contact with the individual's 100 skin, such as the skin of the individual's chest, and secured with a strap. The heart rate sensor 126 may be capable of reading the electrical activity the individual's 100 heart.

The temperature sensor 128 may be, for example, a thermometer, a thermistor, or a thermocouple that measures changes in the temperature. In some embodiments, the temperature sensor 128 may primarily be used for calibration other sensors of the system 10, for example, the acceleration sensor 116 and the magnetic field sensor 146.

In one embodiment, the position receiver 130 may be an electronic satellite position receiver that is capable of determining its location (i.e., longitude, latitude, and altitude) using time signals transmitted along a line-of-sight by radio from satellite position system satellites. Known satellite position systems include the GPS system, the Galileo system, the BeiDou system, and the GLONASS system. In another embodiment, the position receiver 130 may be an antenna that is capable of communicating with local or remote base stations or radio transmission transceivers such that the location of the sensor module 102 may be determined using radio signal triangulation or other similar principles. In some embodiments, position receiver 130 data may allow the sensor module 102 to detect information that may be used to measure and/or calculate position waypoints, time, location, distance traveled, speed, pace, or altitude.

The data port 132 may facilitate information transfer to and from the sensor module 102 and may be, for example, a USB port. In some exemplary embodiments, data port 132 can additionally or alternatively facilitate power transfer to a power source, in order to a charge power source.

The timer 134 may be a clock that is capable of tracking absolute time and/or determining elapsed time. In some embodiments, the timer 134 may be used to timestamp certain data records, such that the time that certain data was measured or recorded may be determined and various timestamps of various pieces of data may be correlated with one another.

In some embodiments, the sensor module 102 may also include a button and/or a display. The button may serve as the user interface of the sensor module 102. The button may be capable of turning the sensor module 102 on and off, toggling through various display options, or serving a variety of other functions. Alternatively, multiple buttons or no buttons may be provided. In one embodiment, the display may be a relatively simple LED display that is capable of conveying the status or battery life of the sensor module 102 to an individual 100 with different color combinations or flashing patterns, for example. In another embodiment, the display may be a more advanced display that is capable of displaying performance parameter information, feedback, or other information to the individual 100, such as a segmented LCD display. Alternatively, no button or display may be provided.

In other embodiments, the sensor module 102 may include audio controls such as a speaker and/or microphone for audio communication with an individual 100. These components may serve as the user interface of the sensor module 102, and may be included an audio input system. These audio controls may be capable of turning the sensor module 102 on and off, toggling through various display options, or serving a variety of other functions. In one embodiment, the audio controls may be capable of conveying the status or battery life of the sensor module 102 to an individual 100. In another embodiment, the audio controls may be capable of outputting or receiving performance parameter information, feedback, or other information to and from the individual 100. In one embodiment, the audio controls may be capable of accepting voice commands form the individual 100. In another embodiment, the sensor module 102 may be capable of relaying audio information to an individual wirelessly via another device, such as a pair of headphones. Alternatively, audio controls may be provided.

Data obtained by the sensor module 102 may be processed in a variety of ways to yield useful information about the motion of an object of interest during the activity, e.g., individual 100. In some embodiments, sensor module 102 data may be processed to monitor changes in the spatial orientation of the individual's 100 body or a piece of the individual's 100 athletic equipment. In other embodiment, sensor module 102 data may be processed to by reference to a predetermined correlation between movement data and a characteristic stored in a data structure.

In some embodiments, sensor modules 102 are used to detect changes in an individual's direction of motion. Sensor modules 102 according to the present invention can also be worn by individuals and used to detect and/or track other motions such as, for example, motions associated with push-ups, pull-ups, weightlifting, diving, gymnastics, et cetera.

Figure 24:
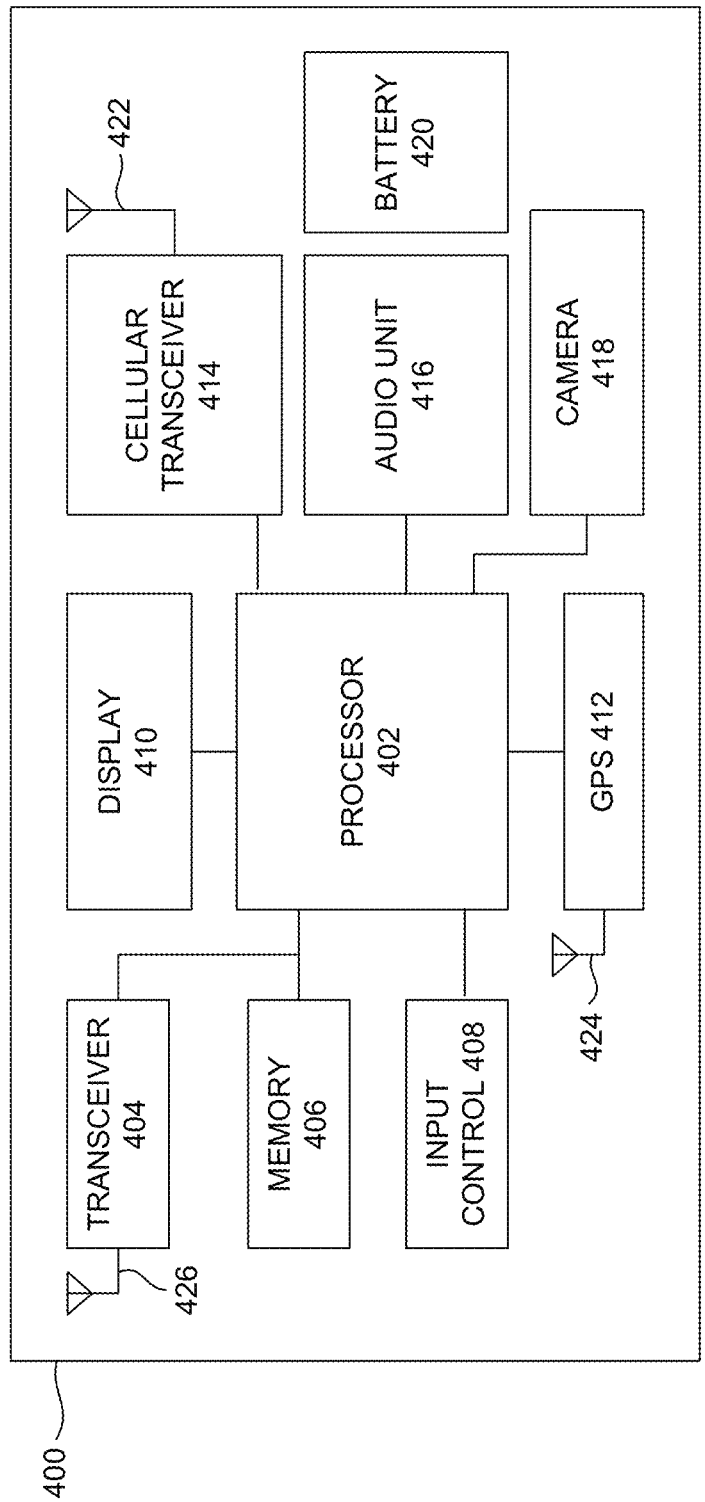
FIG. 24 is an example electronic device useful for implementing various embodiments.

Turning to FIG. 24, a block diagram of electronic device 400 according to an embodiment of the present invention is shown. In an embodiment, electronic device 400 corresponds to a mobile computing device, mobile phone, desktop computer, tablet computer, dedicated electronic device, or the like. As shown in FIG. 24, electronic device 400 may include a processor 402, memory 406, a user input control 408, a display 410, an audio unit 416, a transceiver 404, a cellular transceiver 414, an optional satellite-based positioning system receiver 412, a camera 418, and a battery 420.

Processor 402 is a processor capable of implementing application programs or software platforms 1000 stored in memory 406. Processor 402 is also capable of implementing digital signal processing algorithms. Processor 402 is coupled to memory 304, user input control 408, display 410, audio unit 416, transceiver 404, and may include a cellular transceiver 414.

Memory 406 is used to store application program instructions (e.g., software platform 1000) and data. In an embodiment, memory 406 stores programs, for example, used to implement all of the functionality of a typical electronic device. In an embodiment, memory 406 includes both read only memory and random access memory.

User input control 408 is used by an individual to interact with electronic device 400. In an embodiment, user input control 408 includes a variety of input buttons and/or keys. The function of each of these buttons and/or keys is typically determined based on an operating mode of electronic device 400. In one embodiment, user input control 408 includes a touch pad or scroll pad and/or touch screen buttons.

Display 410 is used to display information to an individual. In an embodiment, display 410 is a liquid crystal display.

Camera 418 is a small digital camera used to take digital photos or video. In one embodiment, camera 418 is a CCD camera. In another embodiment, camera 418 is a CMOS camera.

Audio unit 416 is used to process audio signals. In an embodiment, voice signals picked up using a microphone are converted to digital signals so that they can be operated upon, for example, by processor 402. Audio unit 416 also converts, for example, digital audio signals into amplified analog audio signals that can be used to drive one or more speakers. In an embodiment, audio unit 416 implements signal processing algorithms such as those available from Dolby Laboratories, Inc., which enhance the quality of music.

Transceiver 404 is a low-power transceiver used to communicate with other components of system 10. In an embodiment, transceiver 404 operates in an unlicensed frequency band such as 2.4 GHz. Transceiver 404 is coupled to an antenna 314. As used herein, the term transceiver means a combination of a transmitter and a receiver. In an embodiment, the transmitter and the receiver are integrated and form, for example, a part of an intergraded circuit.

Cellular transceiver 414 may be used to send and receive, for example, voice cellular telephone signals. Transceiver 414 can also be used to exchange information with a computer network such as, for example, the Internet. Cellular transceiver 414 is coupled to an antenna 422. As used herein, the term cellular transceiver means a combination of a cellular transmitter and a cellular receiver. In an embodiment, the transmitter and the receiver are integrated together into a single device.

In one embodiment, cellular transceiver 414 is used to send data described herein to a location where it is analyzed, for example, by a professional trainer. The professional trainer can call or text message the individual and provide the individual substantially real-time feedback based on the data. If the individual wants to call the professional trainer, for example, during a workout, the individual can place a call to the professional trainer, for example, by tapping electronic device 400 to place a call to a stored telephone number. In one embodiment, tapping electronic device 400 sends a text message to the professional trainer requesting that the professional trainer call the individual. These functions may also be included in sensor module 102.

Battery 420 is used to provide power to operate the various components of electronic device 400. In an embodiment, battery 420 is recharged periodically using a power adapter that plugs into a typical household power outlet. Battery 420 can also be a non-rechargeable battery.

In an embodiment, electronic device 400 also includes an optional satellite-based positioning system (e.g., global positioning system (GPS) or Galileo system) receiver 412. This enables the electronic device to determine its location anywhere on the earth. The satellite-based positioning system (e.g., GPS) receiver 412 is coupled to an antenna 424. In an embodiment, GPS receiver 412 enables the electronic device 400, for example, to provide navigational instructions to a runner using the device. The directions for a running route can be downloaded to the electronic device prior to a run and stored in memory 406. In addition to navigational instructions, attributes about the running route such as, for example, whether the route has sidewalks, is on a trail, is located within a safe neighborhood, et cetera, can also be downloaded and viewed. GPS receiver 412 can be used, in an embodiment, to track a route run by a runner. The route can be saved in memory 304 and viewed by the runner after the run. The route can also be shared with other runners, for example, by posting the route on a computer/web server for downloading by other runners.

In an embodiment, GPS receiver 412 and information stored in the memory of electronic device 400 (or information received, e.g., from the internet using cellular transceiver 414) are used to provide navigational instructions, for example, to a runner. In an embodiment, the runner can enter into electronic device 400 that he or she would like to run five kilometers, for example, and the electronic device will automatically select/map-out an appropriate route and provide navigation instructions to the runner during the run. In an embodiment, the runner can specify both a start point and a stop point for the run. In an embodiment, only one point is specified, which serves as both the start point and the stop point. In an embodiment, the start and stop points are the point at which the runner is standing (e.g., as determined by GPS receiver 412) when the runner enters, for example, that he or she would like to run five kilometers.

In an embodiment, electronic device 400 includes a radio. The radio can be an AM only radio, an FM only radio, or both an AM and FM radio. In an embodiment, the radio is controlled using soft keys presented to an individual on display 410.

In one embodiment, electronic device 400 includes optional sensors (not shown) for detecting selected weather related data such as, for example, temperature, humidity, ultra-violet radiation and/or barometric pressure. This data can be used, for example, to determine how an individual's performance is effected by environmental factors.

In one embodiment, an electronic device according to the present invention does not include a display. In this embodiment, information such as, for example, performance and/or feedback information is provided to an individual audibly during a workout, e.g., through sensor module 102, or other audio feedback. The information can be display to the individual, for example, after the workout using a computer display once the information has been transferred to the computer. In an embodiment, the information can be transferred to a second processing device such as, for example, a sports watch during the workout and displayed to the individual during the workout on the display of the second processing device.

In embodiments, an electronic device 400 according to the present invention can be formed, for example, by attaching a dongle (e.g., a small hardware device that protects software) to a conventional phone, a music file player, a personal digital assistant, et cetera. The dongle includes, for example, downloadable software that implements some or all of the sport functions described herein. In an embodiment, the software includes a sport user interface written in the Java programming language. In an embodiment, the software includes drivers, for example, that enable the software to be used with any ultra low power Bluetooth communications protocol compatible device. Other embodiments are compatible with other communications protocol compatible devices.

In an embodiment of the present invention, a electronic device according to the present invention is a dedicated device (rather than a device such as, for example, a phone, a music file player, or a personal digital assistant) that implements the functions as detailed herein.

In some embodiments, the sensor module 102 may then determine that the movement of an individual 100 indicates the occurrence of a movement to track. In one embodiment, the determination that the movement of the individual 100 indicates the occurrence of a movement to track occurs when a threshold data value is met for a predetermined period of time. For example, the sensor module 102 may determine that a movement of the individual has resulted in a threshold acceleration occurring for a predetermined period of time.

In some embodiments, remote processing may be used to augment the processing discussed herein. The remote processing may enable a sensor module 102 to wirelessly transmit data to a remote computer for processing. Wireless communication with other elements of the system 10 is generally described above. In this way, the processing capabilities of the system 10 may be enhanced by shifting certain processing and analytical tasks to a remotely located computer, such as a server computer, with greater computational abilities and, in some embodiments, access to additional data or other resources.

In some embodiments, the data received may be transmitted to the remote computer during the athletic activity. In another embodiment, the data received may be transmitted to the remote computer after the athletic activity has been completed.

In some embodiments, the physiological data received may be compared to data associated with the individual 100 for the present athletic activity and data associated with the individual 100 from a previous athletic activity. In some embodiments, the data may be compared to data received during a different individual's 100 athletic activity.

By using the system 10 including the sensor module 102 described above, embodiments of the present invention may advantageously enable the individual 100 (or their coach, teammate, a spectator, friends, competitors, etc.) to obtain this or other information about the motion of the individual's 100 body, or other information related to the health, nutrition, wellness, mindset, etc. of the individual 100 during or after the course of the athletic activity.

For running, sensor module 102 embodiments such as those described above may enable an individual 100, to determine, for example, characteristics of a runner's motion. For example, a sensor module 102 could be used to determine the speed, pace, distance traversed, locations traversed, or to discriminate between different surfaces (e.g., grass, street, or trail) and inclinations (e.g., uphill, flat, or downhill). In some embodiments the sensor module 102 may be mounted, for example, on a runner's torso, arm, hand, leg, foot, or head, or on or in their article of footwear, or integrated into electronic device 400.

In some embodiments of the present invention, the sensor module 102 may be capable of compensating for inherent deficiencies that may be present for various types of sensor contained within or in communication with the sensor module 102. Most real world sensors have limitations. For example, accelerometers, magnetometers, and gyroscopes may have accuracy issues, particularly when used at speeds of motion of the individual 100 or under other conditions that differ from their initial calibration conditions.

In some embodiments of the present invention, the sensor module 102 may communicate with other components of the system 10 via wired or wireless technologies. Communication between the sensor module 102 and other components of the system 10 may be desirable for a variety of reasons. For example, to the extent that the sensor module 102 records and stores athletic activity information, it may be useful to transmit this information to another electronic device for additional data processing, data visualization, sharing with others, comparison to previously recorded athletic activity information, or a variety of other purposes. As a further example, to the extent that the sensor module 102 has insufficient processing power, wide area network transmission capabilities, sensor capabilities, or other capabilities, these capabilities can be provided by other components of the system 10. With this in mind, possible communications means are described briefly below.

Figure 25:
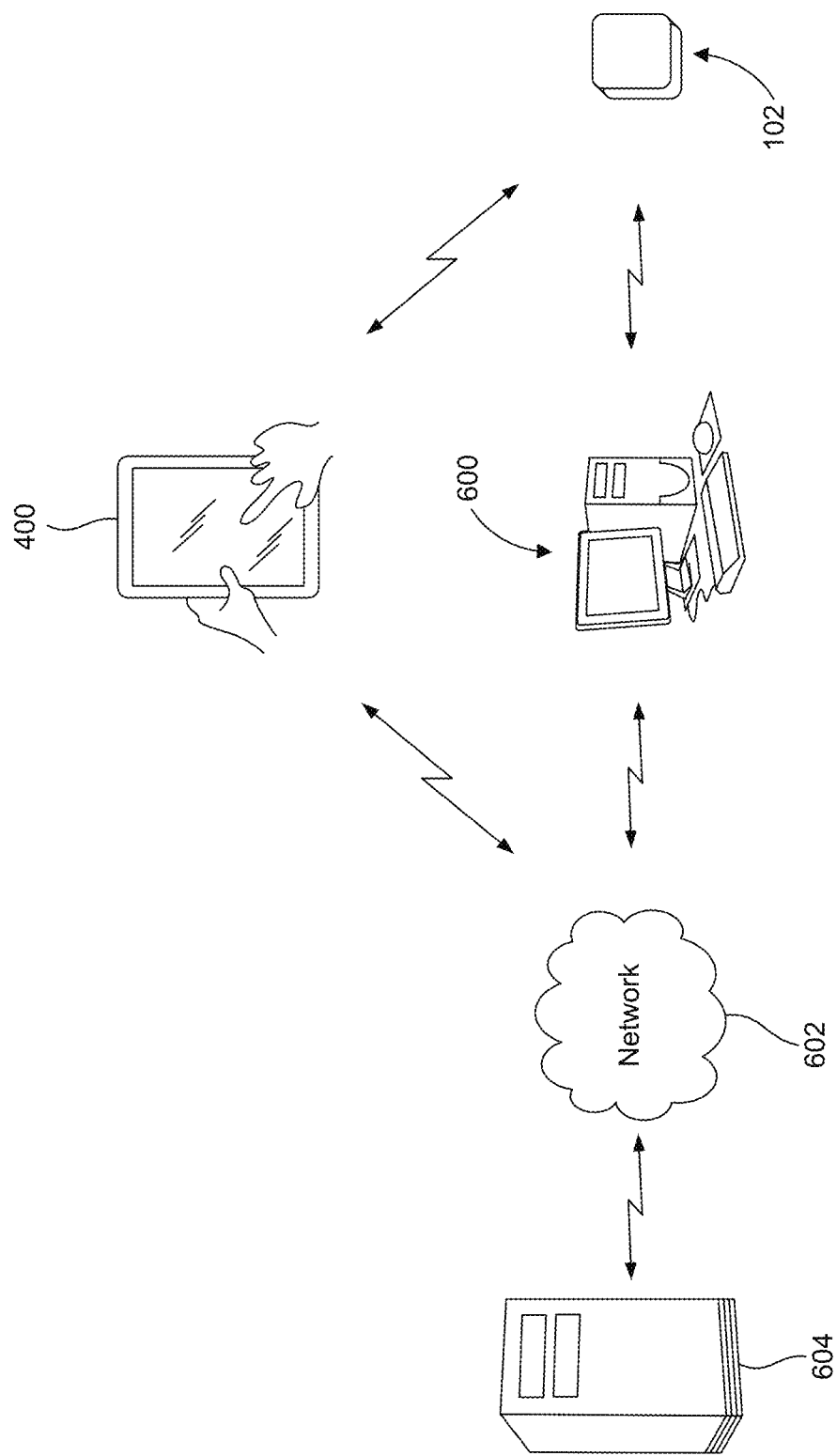
FIG. 25 shows a representative communication system useful for implementing various embodiments.

FIG. 25 is a diagram of a sensor module interacting with one of an electronic device, a standalone device, a network, and a server according to an embodiment of the present invention.

Transceiver 112 may allow sensor module 102 to communicate, for example, with other locally or remotely located individuals 100, or other standalone devices 600, via network 602, or server 604, for example, as shown in FIG. 25. Communication between these components may be one way communication or two way communication.

Communication may also occur between the sensors, electronic device, and/or a remote server 604 via a network 602, for example, as shown in FIG. 25. In some embodiments, the network is the Internet. The Internet is a worldwide collection of servers, routers, switches and transmission lines that employ the Internet Protocol (TCP/IP) to communicate data. The network may also be employed for communication between any two or more of the sensors, the electronic device, the server, etc. In some embodiments of the present invention, information is directly communicated between the sensors or processor and the server via the network, thus bypassing the electronic device.

A variety of information may be communicated between any of the components that may transmit or receive data or information. Such information may include, for example, performance parameter data, device settings (including sensor settings), software, and firmware.

Communication among the various elements of the present invention may occur after a workout/athletic activity, or other experience has been completed or in substantially real-time during the workout/athletic activity, or other experience.

The electronic device 400 may serve a variety of purposes including, for example, providing additional data processing, providing instructions to individual 100; providing additional data storage, providing data visualization, providing additional sensor capabilities, relaying information to a network 602, providing for the playback of music or videos, or the like.

The electronic device 400 illustrated in the figures may not be a dedicated electronic monitoring device; the electronic device 400 illustrated in the figures may be a mobile phone, dedicated fitness monitor, smart watch, tablet computer, etc. In alternate embodiments, it may be possible for the sensor module 102 itself to be embodied by a mobile phone, or for the electronic device 400 to be a mobile phone. Including an electronic device 400 in the system 10, such as a mobile phone, may be desirable as mobile phones are commonly carried by individuals 400, even when engaging in athletic activities, and they are capable of providing significant additional computing and communication power at no additional cost to the individual 100.

Wired communication between the sensor module 102 and an electronic device 400 may be achieved, for example, by placing the sensor module 102—or a piece of athletic equipment or electronic device 400 including the sensor module 102—in a docking unit that is attached to the electronic device 400 using a communications wire plugged into a communications port of the electronic device 400. In another embodiment, wired communication between the sensor module 102 and the electronic device 400 may be achieved, for example, by connecting a cable between the sensor module 102—or a piece of athletic equipment or electronic device 400 including the sensor module 102—and the computer or standalone device 600. The data port 132 of the sensor module 102 and a communications port of the computer 600 may include USB ports. The cable connecting the sensor module 102 and the computer 600 may be a USB cable with suitable USB plugs including, but not limited to, USB-A or USB-B regular, mini, or micro plugs, or other suitable cable such as, for example, a FireWire, Ethernet or Thunderbolt cable. As previously explained above, in some embodiments, such cables could be used to facilitate power transfer to a power source of the sensor module 102, in order to charge the power source. Alternatively, the power source may be recharged by inductive charging, or by using a docking station with a charging base.

Wired connection to an electronic device 400 may be useful, for example, to upload athletic activity information from the sensor module 102 to the electronic device 400, or to download application software updates or settings from the electronic device 400 to the sensor module 102.

Wireless communication between the sensor module 102—or a piece of athletic equipment or electronic device 400 including the sensor module 102—and the electronic device 400 may be achieved, for example, by way of a wireless wide area network (such as, for example, the Internet), a wireless local area network, or a wireless personal area network. As is well known to those skilled in the art, there are a number of known standard and proprietary protocols that are suitable for implementing wireless area networks (e.g., TCP/IP, IEEE 802.16, Bluetooth, Bluetooth low energy, ANT, ANT+ by Dynastream Innovations, or BlueRobin). Accordingly, embodiments of the present invention are not limited to using any particular protocol to communicate between the sensor module 102 and the various elements of the system 10 of the present invention.

In one embodiment, the sensor module 102—or a piece of athletic equipment or electronic device 400 including the sensor module 102—may communicate with a wireless wide area network communications system such as that employed by mobile telephones. For example, a wireless wide area network communication system may include a plurality of geographically distributed communication towers and base station systems. Communication towers may include one or more antennae supporting long-range two-way radio frequency communication wireless devices, such as sensor module 102. The radio frequency communication between antennae and the sensor module 102 may utilize radio frequency signals conforming to any known or future developed wireless protocol, for example, CDMA, GSM, EDGE, 3G, 4G, IEEE 802.x (e.g., IEEE 802.16 (WiMAX)), etc. The information transmitted over-the-air by the base station systems and the cellular communication towers to the sensor module 102 may be further transmitted to or received from one or more additional circuit-switched or packet-switched communication networks, including, for example, the Internet.

As previously noted, in some embodiments of the present invention, sensor module 102 may communicate with an electronic device, such as a smart phone, that is also carried by the individual 100 during the athletic activity or experience.

In some embodiments of the present invention, for example, as shown in FIG. 24, the electronic device 400 may take the form of a mobile phone and may include at least a processor, a memory, user input controls, a positioning system receiver, a wireless wide area network (WWAN) transceiver, a visual display, and an audio unit. A visual display in the form of a LCD screen, and user input controls in the form of a physical keyboard and a scroll ball may be present.

The memory of the electronic device 400 may be adapted to store application programs, software platforms or modules, used to implement aspects of the functionality of the system 10 described herein. Alternatively, those of skill in the art will understand that all or part of the software may be stored on the server 604 and accessed over the network 602 and run remotely as a mobile web application, or stored locally in electronic device 400, having a memory.

Those skilled in the art will appreciate that alternative or additional software modules and sub-modules may be implemented in order to provide or extend the described or additional functionalities to the individual 100 using the electronic device 400. For example, the software configuration of software stored on an electronic device 400 may include a device operating system, which may be one of the commercially available mobile phone operating systems such as, for example, BlackBerry OS, iPhone OS, Windows Mobile, Symbian, LINUX, WebOS, or Android. The device operating system may also have an associated application programming interface through which middleware and application programs may access the services of the operating system.

The various modules of the system 10 of the present invention may support GUIs through which an individual 100 can interact with the system 10 using the electronic device 400 just prior to and/or during an activity. As will be appreciated by those of skill in the art, in one embodiment the GUIs may be supported by a mobile device application being run on the electronic device 400. In another embodiment, the GUIs may appear as web pages provided by the server 604 via a website that may be accessible to the individual 100 over the network 602 using a web browser on their electronic device 400. The GUIs may be considered to be part of the methods or systems of the present invention.

In some embodiments, the system 10 may be sold as a package, including an electronic device 400, sensor modules 102 for multiple individuals 100, and a charger.

System 10 may recognize and record repeat usage of the system 10 over time, number of times various individuals store their data into a profile and update that data. The system 10 may also be able to integrate with various social media platforms, allowing individuals to share with their social network data regarding their gait characteristics, their usage of the system 10.

Figure 26:
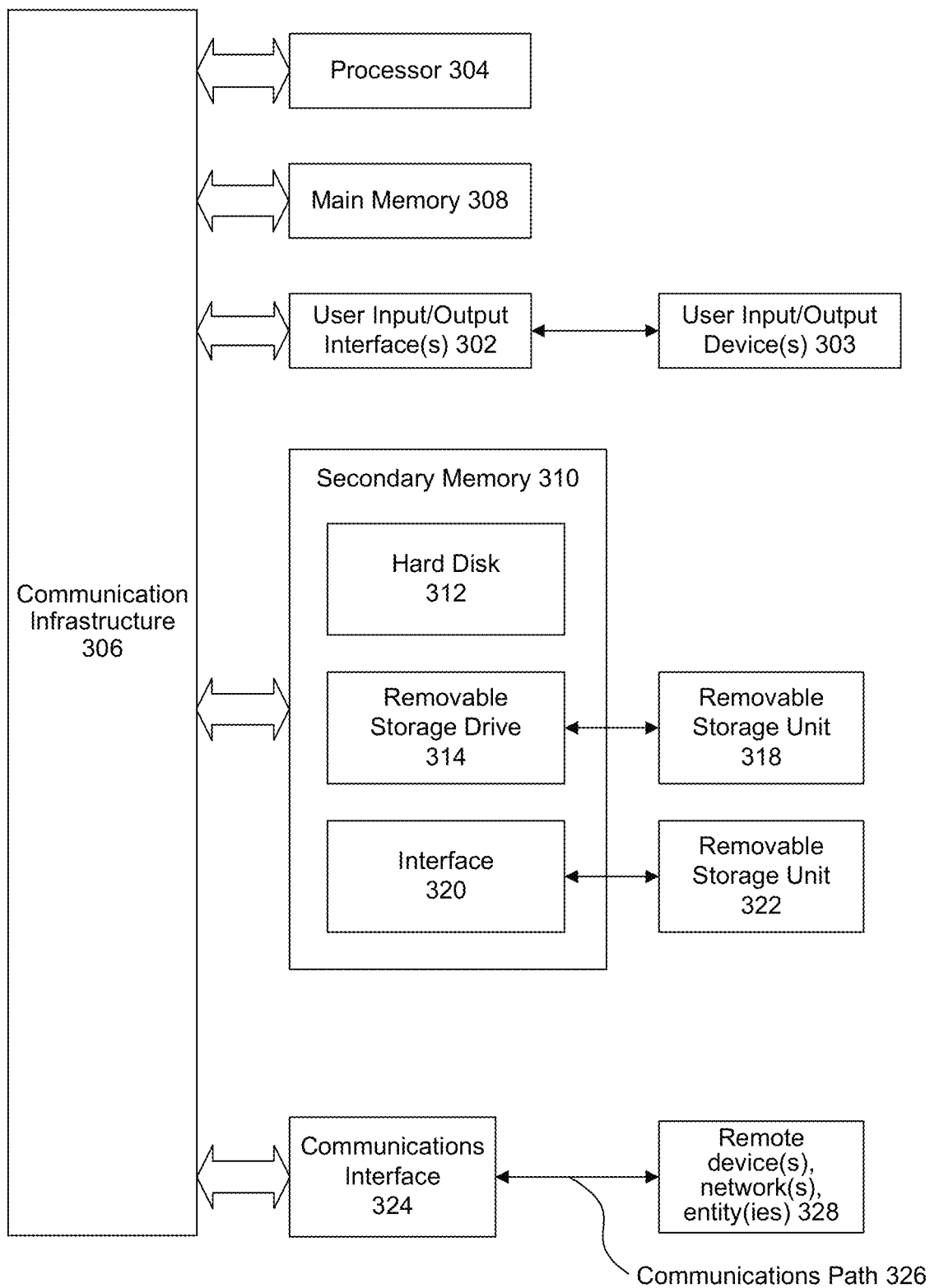
FIG. 26 is an example computer system useful for implementing various embodiments.

Embodiments can be implemented, for example, using one or more well-known computer systems or one or more components included in computer system 3100 shown in FIG. 26. Computer system 3100 can be any well-known computer capable of performing the functions described herein, including electronic device 400.

Computer system 3100 includes one or more processors (also called central processing units, or CPUs), such as a processor 3104. Processor 3104 is connected to a communication infrastructure or bus 3106.

One or more processors 3104 may each be a graphics processing unit (GPU). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 3100 also includes user input/output device(s) 3103, such as monitors, keyboards, pointing devices, etc., that communicate with communication infrastructure 3106 through user input/output interface(s) 3102.

Computer system 3100 also includes a main or primary memory 3108, such as random access memory (RAM). Main memory 3108 may include one or more levels of cache. Main memory 3108 has stored therein control logic (i.e., computer software) and/or data.

Computer system 3100 may also include one or more secondary storage devices or memory 3110. Secondary memory 3110 may include, for example, a hard disk drive 3112 and/or a removable storage device or drive 3114. Removable storage drive 3114 may be a floppy disk drive, a magnetic tape drive, a compact disk drive, an optical storage device, tape backup device, and/or any other storage device/drive.

Removable storage drive 3114 may interact with a removable storage unit 3118. Removable storage unit 3118 includes a computer usable or readable storage device having stored thereon computer software (control logic) and/or data. Removable storage unit 3118 may be a floppy disk, magnetic tape, compact disk, DVD, SD-Card, optical storage disk, and/or any other computer data storage device. Removable storage drive 3114 reads from and/or writes to removable storage unit 3118 in a well-known manner.

According to an exemplary embodiment, secondary memory 3110 may include other means, instrumentalities or other approaches for allowing computer programs and/or other instructions and/or data to be accessed by computer system 3100. Such means, instrumentalities or other approaches may include, for example, a removable storage unit 3122 and an interface 3120. Examples of the removable storage unit 3122 and the interface 3120 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 3100 may further include a communication or network interface 3124. Communication interface 3124 enables computer system 3100 to communicate and interact with any combination of remote devices, remote networks, remote entities, etc. (individually and collectively referenced by reference number 3128). For example, communication interface 3124 may allow computer system 3100 to communicate with remote devices 3128 over communications path 3126, which may be wired and/or wireless, and which may include any combination of LANs, WANs, the Internet, etc. Control logic and/or data may be transmitted to and from computer system 3100 via communication path 3126.

In an embodiment, a tangible apparatus or article of manufacture comprising a tangible computer useable or readable medium having control logic (software) stored thereon is also referred to herein as a computer program product or program storage device. This includes, but is not limited to, computer system 3100, main memory 3108, secondary memory 3110, and removable storage units 3118 and 3122, as well as tangible articles of manufacture embodying any combination of the foregoing. Such control logic, when executed by one or more data processing devices (such as computer system 3100), causes such data processing devices to operate as described herein.

In some embodiments, the movement of the bodies of a plurality of individuals engaged in an athletic activity or experience and/or the movement of a plurality of pieces of athletic equipment used by the individuals during the athletic activity or experience may be monitored. In some embodiments, real-time monitoring and/or feedback may be provided, while in other embodiments post-activity feedback may be provided.

Figure 29:
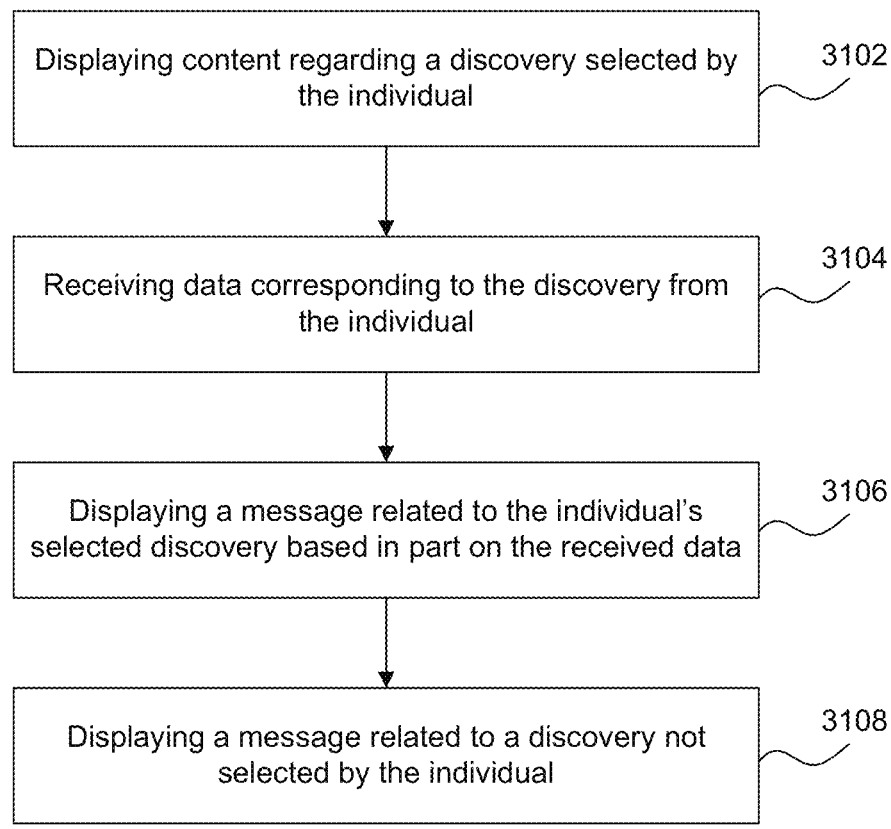
FIG. 29 is a flowchart illustrating a method for providing feedback to an individual related to a discovery according to an embodiment.

FIG. 29 is a flowchart illustrating a method 3100 for providing feedback to an individual related to a discovery according to an embodiment. At step 3102, the method may include displaying content regarding a discovery selected by the individual. Then, at step 3104, the method may include receiving data corresponding to the discovery from the individual. At step 3106, the method may include displaying a message related to the individual's selected discovery based in part on the received data. At step 3106, the method may include displaying a message related to a discovery not selected by the individual. In some embodiments, the discovery is related to a domain selected from movement, nutrition, mindset, and rest. In some embodiments, the method includes querying the individual regarding a baseline level of performance related to the selected domain. In some embodiments, the message related to the individual's selected discovery is dependent upon the individual's progress through the discovery. In some embodiments, the message related to the individual's selected discovery is independent upon the individual's progress through the discovery. In some embodiments, the data received includes motion data of the individual. In some embodiments, the method includes querying the individual regarding their perception of the discovery, and displaying content regarding the discovery depending on the perception of the discovery. In some embodiments, the method includes displaying a message related to the discovery based on the individual's location. In some embodiments, the method includes querying the individual regarding their perception of the discovery, determining, based on the query, a likely state of the individual corresponding to their readiness to change, and adjusting the tone of the message based on the likely state of the individual. In some embodiments, the likely state of the individual is categorized based on the transtheoretical model.

Exemplary methods 3100, 3200, and 3300 may include each of the steps shown in the other methods, as well as steps described but not shown in the figures. Further, the methods may include the system 10, including, for example, electronic device 400.

Figure 30:
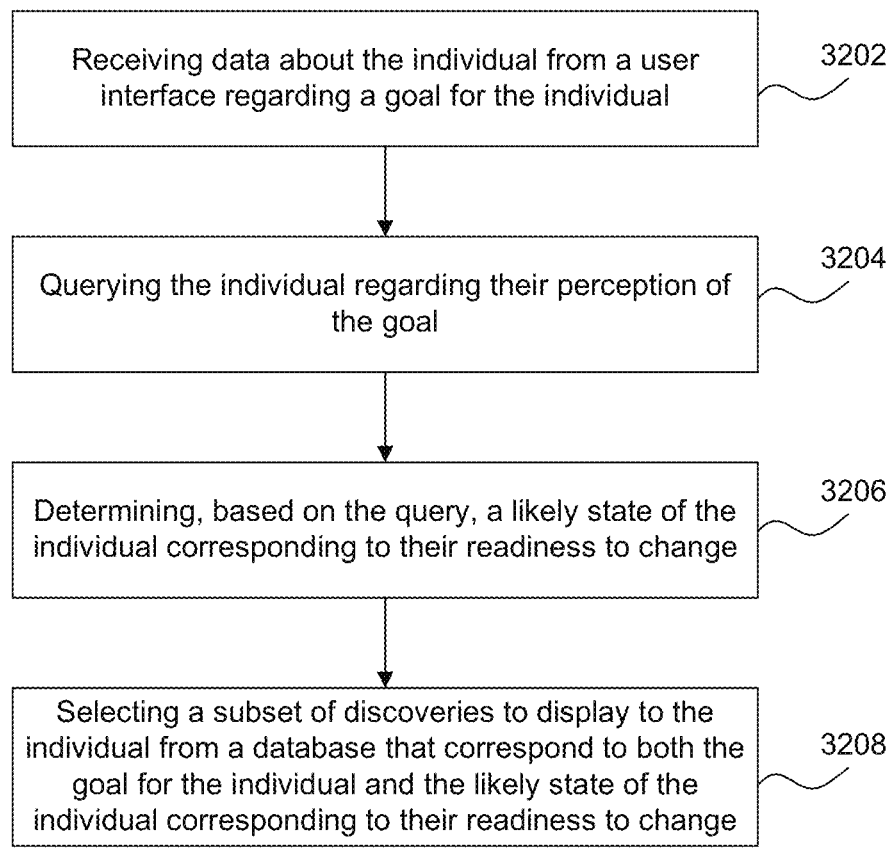
FIG. 30 is a flowchart illustrating a method for suggesting a discovery to an individual according to an embodiment.

FIG. 30 is a flowchart illustrating a method 3200 for suggesting a discovery to an individual according to an embodiment. In some embodiments, at step 3202, method 3200 includes receiving data about the individual from a user interface regarding a goal for the individual. At step 3204, the method may include querying the individual regarding their perception of the goal. Next, at step 3206, the method may include determining, based on the query, a likely state of the individual corresponding to their readiness to change. At step 3206, the method may include selecting a subset of discoveries to display to the individual from a database that correspond to both the goal for the individual and the likely state of the individual corresponding to their readiness to change. In some embodiments, a likely state of the individual is categorized based on the transtheoretical model. In some embodiments, the goal corresponds to a domain selected from movement, nutrition, mindset, and rest. In some embodiments, the method includes querying the individual regarding their progress through a previously selected discovery, and updating the selection of a subset of discoveries to display to the individual based on the query. In some embodiments, the querying the individual regarding their perception of the goal includes querying the individual regarding a baseline selected from movement, nutrition, mindset, and rest. In some embodiments, the method includes adjusting the content of a subset of discoveries based on the likely state of the individual corresponding to their readiness to change.

Figure 31:
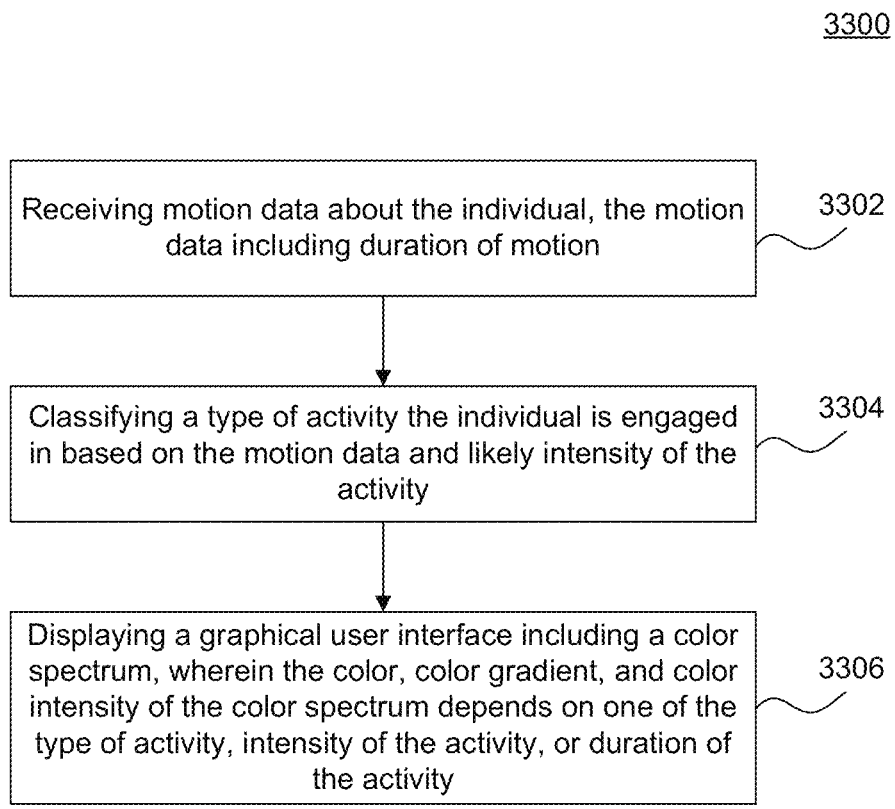
FIG. 31 is a flowchart illustrating a method for displaying information to an individual according to an embodiment.
Figure 32:
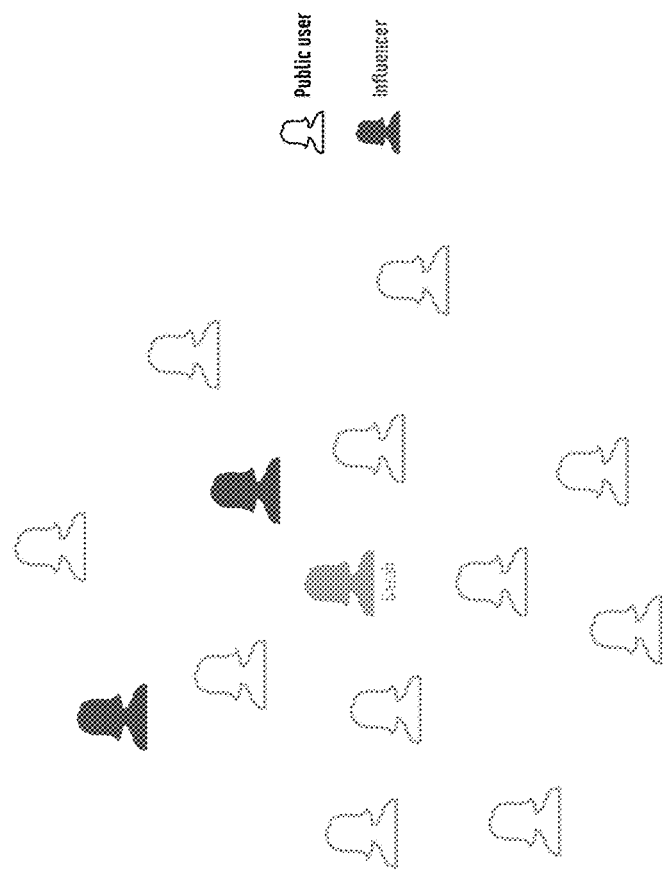
Figure 35:
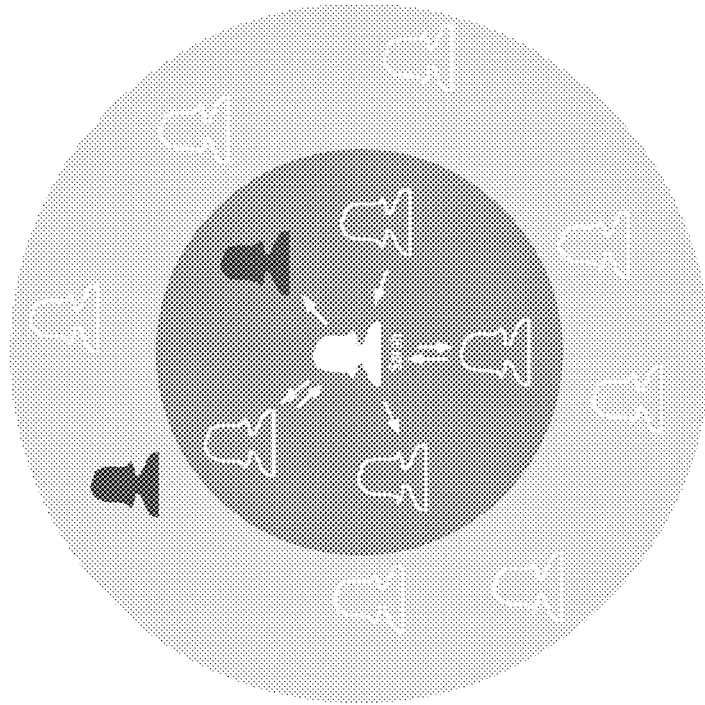
Figure 36:
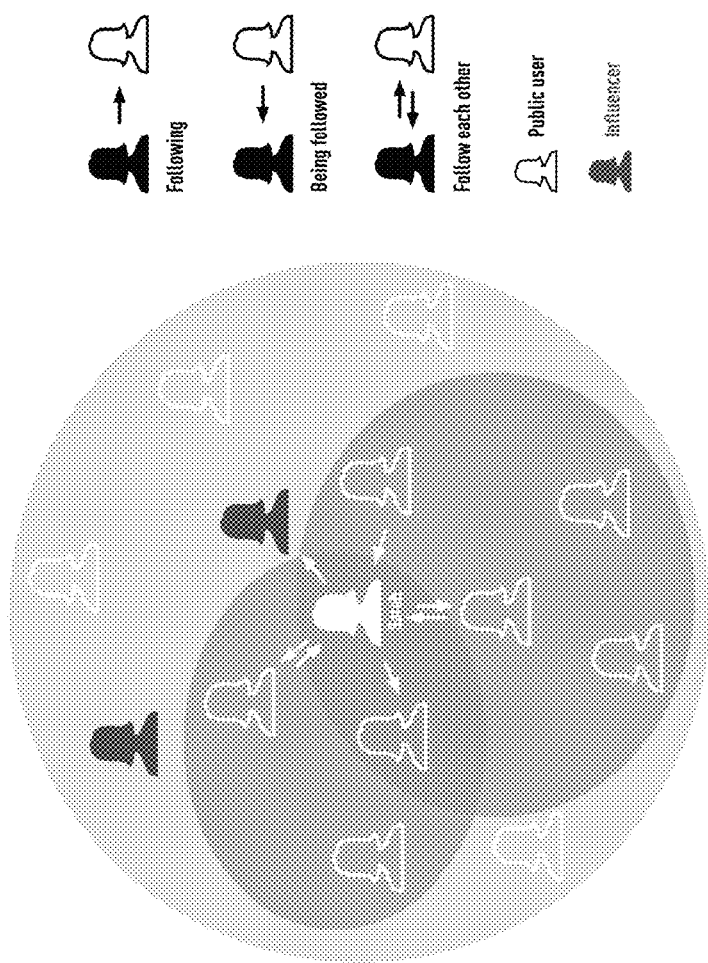

FIG. 31 is a flowchart illustrating a method 3300 for displaying information to an individual according to an embodiment. In some embodiments, starting at step 3302, the method may include receiving motion data about the individual, the motion data including duration of motion. At step 3304, the method may include classifying a type of activity the individual is engaged in based on the motion data and likely intensity of the activity. In some embodiments, the method may include step 3306, including displaying a graphical user interface including a color spectrum, wherein the color, color gradient, and color intensity of the color spectrum depends on one of the type of activity, intensity of the activity, or duration of the activity. In some embodiments, the method includes receiving a second motion data about the individual, the second motion data including duration of motion, classifying a type of second activity the individual is engaged in based on the second motion data and likely intensity of the activity, adding the duration of the first and second activity, wherein the color, color gradient, and color intensity of the color spectrum depends on one of the type of first or second activity, intensity of the activities, or sum of the duration of the activities. In some embodiments, the method includes receiving data manually input from the individual regarding an activity, and adding the duration of the manually input activity to the previous total. In some embodiments, the method includes altering the color spectrum is further dependent upon an additional non-motion data source. These color properties may be included in color region 2104, for example.

Various aspects of the present invention, or any parts or functions thereof, may be implemented using hardware, software, firmware, tangible non-transitory computer readable or computer usable storage media having instructions stored thereon, or a combination thereof and may be implemented in one or more computer systems or other processing systems.

Program products, methods, and systems of the present invention can include any software application executed by one or more electronic devices 400. An electronic device 400 can be any type of computing device having one or more processors. For example, the electronic device 400 can be a workstation, mobile device (e.g., a mobile phone, personal digital assistant, tablet computer, or laptop), computer, server, compute cluster, server farm, game console, set-top box, kiosk, embedded system, a gym machine, a retail system or retail enhancement system or other device having at least one processor and memory. Embodiments of the present invention may be software executed by a processor, firmware, hardware or any combination thereof in a computing device.

In this document, terms such as "computer program medium" and "computer-usable medium" may be used to generally refer to media such as a removable storage unit or a hard disk installed in hard disk drive. Computer program medium and computer-usable medium may also refer to memories, such as a main memory or a secondary memory, which can be memory semiconductors (e.g., DRAMs, etc.). These computer program products provide software to computer systems of the present invention.

Computer programs (also called computer control logic) may be stored on main memory and/or secondary memory. Computer programs may also be received via a communications interface. Such computer programs, when executed, may enable computer systems of the present invention to implement embodiments described herein. Where embodiments are implemented using software, the software can be stored on a computer program product and loaded into a computer system using, for example, a removable storage drive, an interface, a hard drive, and/or communications interface.

Based on the description herein, a person skilled in the relevant art will recognize that the computer programs, when executed, can enable one or more processors to implement processes described above, such as the steps in the methods illustrated by the figures. In some embodiments, the one or more processors can be part of a computing device incorporated in a clustered computing environment or server farm. Further, in some embodiments, the computing process performed by the clustered computing environment may be carried out across multiple processors located at the same or different locations.

Software of the present invention may be stored on any computer-usable medium. Such software, when executed in one or more data processing device, causes the data processing device to operate as described herein. Embodiments of the invention employ any computer-usable or -readable medium, known now or in the future. Examples of computer-usable mediums include, but are not limited to, primary storage devices (e.g., any type of random access or read only memory), secondary storage devices (e.g., hard drives, floppy disks, CD ROMS, ZIP disks, tapes, magnetic storage devices, optical storage devices, MEMS, nanotechnological storage devices, memory cards or other removable storage devices, etc.), and communication mediums (e.g., wired and wireless communications networks, local area networks, wide area networks, intranets, etc.).

The systems and methods described herein contemplate physical alteration of code or components, and transforming code or components such that the system or method is physically altered (e.g., creating a new data file, for example). The solutions provided herein may be rooted in technology, e.g., computer technology, and overcome problems related to physiological monitoring for example, that are unique to technological realms such as networking or software related issues with data processing. The systems and methods described herein additionally may contemplate additional elements beyond data relationships, such that the solutions tie process advantages to a particular device and increase performance of such a device (e.g., increasing processing efficiency, resolution for location based features, etc.).

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments of the system described with reference to the figures will so fully reveal the general nature of the invention that others can, by applying knowledge within the skill of the art, readily modify and/or adapt for various applications such specific embodiments, without undue experimentation, without departing from the general concept of the present invention.

While various embodiments of the present invention have been described above, they have been presented by way of example only, and not limitation. It should be apparent that adaptations and modifications are intended to be within the meaning and range of equivalents of the disclosed embodiments, based on the teaching and guidance presented herein. It therefore will be apparent to one skilled in the art that various changes in form and detail can be made to the embodiments disclosed herein without departing from the spirit and scope of the present invention. The elements of the embodiments presented above are not necessarily mutually exclusive, but may be interchanged to meet various needs as would be appreciated by one of skill in the art.

It is to be understood that the phraseology or terminology used herein is for the purpose of description and not of limitation. The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

The file of this patent contains at least one drawing/photograph executed in color. Copies of this patent with color drawing(s)/photograph(s) will be provided by the Office upon request and payment of the necessary fee.

What is claimed is:

1. A health and fitness monitoring system for suggesting discoveries to
an individual, comprising:
a database comprising:
the discoveries, wherein the discoveries are content related to time bound experiences, and wherein the discoveries are mapped to goals for the individual and to domains;
an electronic device comprising:
a user interface configured to interface with the individual regarding the goals;
a processor configured to interface with the database; and
a non-transitory computer readable medium having stored thereon a software platform; and
at least one sensor configured to automatically detect performance parameters associated with the individual during an activity;
wherein when executed by the processor the software platform is configured to cause the processor to:
query the individual, using the user interface, regarding their perception of a goal of the goals, and automatically determine based on the query, a likely state of the individual corresponding to their readiness to change,
interface with the database to select a subset of the discoveries to display to the individual on the user interface, the subset of the discoveries corresponding to both the goal for the individual and the likely state of the individual corresponding to their readiness to change,
automatically adjust the subset of the discoveries based on the likely state of the individual corresponding to their readiness to change,
compare the detected performance parameters to performance parameters associated with the individual during a previous activity,
provide insights, via the user interface, identifying correlations between the discoveries, the goals, and the domains to help the individual correlate the discoveries, the goals, and the domains, and
recommend discoveries based on the insights and based on the comparison of the detected performance parameters to performance parameters associated with the individual during the previous activity.

2. The health and fitness monitoring system of claim 1, wherein when executed by the processor the software platform is further configured to cause the processor to categorize the likely state of the individual based on a transtheoretical model.

3. The health and fitness monitoring system of claim 1, wherein the domains include at least one of movement, nutrition, mindset, and rest.

4. The health and fitness monitoring system of claim 1, wherein when executed by the processor the software platform is further configured to cause the processor to:
query the individual regarding their progress through a previously selected discovery; and
update the selection of the subset of the discoveries to display to the individual based on the query.

5. The health and fitness monitoring system of claim 1, wherein the querying the individual regarding their perception of the goal comprises:
querying the individual regarding a baseline selected from movement, nutrition, mindset, and rest.

6. The health and fitness monitoring system of claim 1, further comprising at least one sensor configured to automatically detect physical or physiological data regarding the individual,
wherein when executed by the processor the software platform is configured to cause the processor to automatically adjust the subset of the discoveries based also on the physical or physiological data automatically detected by the at least one sensor, and
wherein the physical or physiological data detected by the sensor comprises at least one of motion data, heart rate data, breathing data, step count data, distance data, location data, and weight data.

7. The health and fitness monitoring system of claim 1, wherein the goals comprise at least one of look good, feel good, emotional wellbeing, athletic performance, eat healthier, increase focus, manage stress, improve mood, sleep better, maintain physical activity, be more active, increase energy, lose weight, and gain weight.

8. The method of claim 1, wherein when executed by the processor the software platform is further configured to compare the detected performance parameters to performance parameters associated with an activity of a second individual.

9. A method for suggesting discoveries to an individual comprising:
mapping the discoveries, within a database, to goals for the individual and to domains, wherein the discoveries are content related to time bound experiences;
receiving data electronically about the individual from a user interface regarding a goal of the goals for the individual;
querying, via a processor and the user interface, the individual regarding their perception of the goal;
determining, via the processor and based on the query, a likely state of the individual corresponding to their readiness to change;
selecting, via the processor, a subset of the discoveries to display to the individual from the database that correspond to both the goal for the individual and the likely state of the individual corresponding to their readiness to change;
adjusting, automatically via the processor, the subset of the discoveries based on the likely state of the individual corresponding to their readiness to change;
detecting performance parameters associated with the individual during an activity;
comparing the detected performance parameters to performance parameters associated with the individual during a previous activity; and
providing insights, via the user interface, identifying correlations between the discoveries, the goals, and the domains to help the individual correlate the discoveries, the goals, and the domains; and
recommending discoveries based on the insights and based on the comparison of the detected performance parameters to performance parameters associated with the individual during the previous activity.

10. The method of claim 9, wherein the likely state of the individual is categorized based on a transtheoretical model.

11. The method of claim 9, wherein the domains include at least one of movement, nutrition, mindset, and rest.

12. The method of claim 9, further comprising:
querying the individual regarding their progress through a previously selected discovery; and
updating the selection of the subset of discoveries to display to the individual based on the query.

13. The method of claim 9, wherein the querying the individual regarding their perception of the goal comprises:
querying the individual regarding a baseline selected from movement, nutrition, mindset, and rest.

14. The method of claim 9, further comprising detecting via at least one sensor, physical or physiological data regarding the individual,
wherein the adjusting the subset of the discoveries is also based on the physical or physiological data, and
wherein the physical or physiological data detected by the sensor comprises at least one of motion data, heart rate data, breathing data, step count data, distance data, location data, and weight data.

15. The method of claim 9, wherein the goals comprise at least one of look good, feel good, emotional wellbeing, athletic performance, eat healthier, increase focus, manage stress, improve mood, sleep better, maintain physical activity, be more active, increase energy, lose weight, and gain weight.

* * * * *

UNITED STATES PATENT AND TRADEMARK OFFICE
CERTIFICATE OF CORRECTION

| | |
|---|---|
| PATENT NO. | : 11,529,074 B2 |
| APPLICATION NO. | : 15/456272 |
| DATED | : December 20, 2022 |
| INVENTOR(S) | : Amy Jones Vaterlaus |

It is certified that error appears in the above-identified patent and that said Letters Patent is hereby corrected as shown below:

In the Claims

In Column 50, Claim 1, Line 26, replace "discoveries to" with --discoveries to an individual, comprising:--;
In Column 50, Claim 1, Line 27, delete "an individual, comprising:".
In Column 51, Claim 8, Line 43, replace "method" with --health and fitness monitoring system--.

Signed and Sealed this
Twenty-first Day of March, 2023

*Katherine Kelly Vidal*

Katherine Kelly Vidal
*Director of the United States Patent and Trademark Office*